United States Patent [19]

McDonald et al.

[11] Patent Number: 5,010,200
[45] Date of Patent: Apr. 23, 1991

[54] PYRIMIDINE DERIVATIVES

[75] Inventors: Edward McDonald, Marlow; Roger Salmon, Bracknell; Alan J. Whittle, Twyford; Michael G. Hutchings, Manchester, all of Great Britain

[73] Assignee: Imperial Chemical Industries PLC, London, England

[21] Appl. No.: 485,083

[22] Filed: Feb. 16, 1990

Related U.S. Application Data

[60] Division of Ser. No. 206,097, Jun. 13, 1988, Pat. No. 4,962,109, which is a continuation-in-part of Ser. No. 942,436, Dec. 16, 1986, Pat. No. 4,762,835.

[30] Foreign Application Priority Data

Dec. 23, 1985 [GB] United Kingdom ............... 8531637
Jun. 17, 1987 [GB] United Kingdom ............... 8714233

[51] Int. Cl.$^5$ ................. C07D 295/06; C07D 295/10; C07D 229/00
[52] U.S. Cl. .................................. 546/245; 544/318; 544/322; 544/334; 544/335; 548/573; 548/572; 560/155; 560/172; 560/173; 560/177; 514/256; 546/248
[58] Field of Search .................. 546/245; 548/573; 560/155, 177, 172, 173; 260/502.5 R

[56] References Cited

U.S. PATENT DOCUMENTS 4,661,488 4/1987 McDonald ................. 514/256
4,762,835 8/1988 Whittle et al. ............. 514/256

Primary Examiner—Cecilia Shen
Attorney, Agent, or Firm—Cushman, Darby and Cushman

[57] ABSTRACT

This invention provides novel insecticidally and acaricidally active pyrimidine derivatives of formula (I):

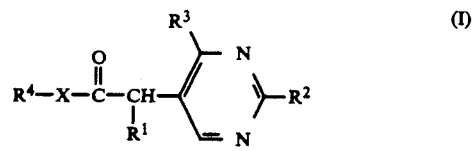

and stereoisomers thereof, wherein $R^1$ is selected from alkyl; alkenyl; alkynyl; haloalkyl; haloalkenyl; and cycloalkyl optionally substituted by alkyl or halogen;

$R^2$ is selected from alkyl; haloalkyl; alkoxy; alkylamino; dialkylamino; halogen; cycloalkyl optionally substituted by halogen or alkyl; and phenyl optionally substituted by alkyl, haloalkyl, halogen or alkoxy;

$R^3$ is selected from hydrogen and halogen;

$R^4$ is the residue of an alcohol of formula $R^4$-OH which forms an insecticidal ester when combined with chrysanthemic acid, permethrin acid or cyhalothrin acid; and X is selected from oxygen and sulphur.

1 Claim, No Drawings

PYRIMIDINE DERIVATIVES

This is a division of application Ser. No. 07/206,097, filed June 13, 1988, now U.S. Pat No. 4,962,109 which is a continuation-in-part of Ser. No. 942,436, filed Dec. 16, 1982, now U.S. Pat. No. 4,762,835.

This invention relates to novel insecticidally and acaricidally active esters and compositions comprising them, and to novel acids and derivatives thereof useful in their preparation. The invention also relates to processes for preparing the novel esters, acids and derivatives and to novel compounds useful in such processes.

In a first aspect the invention provides novel compounds of formula (I):

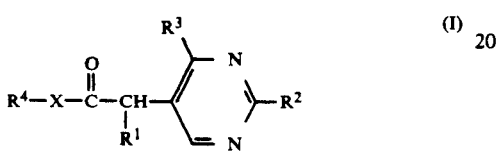

and stereoisomers thereof, wherein:

$R^1$ is selected from alkyl containing 1 to 6 carbon atoms; alkenyl containing 2 to 8 carbon atoms; alkynyl containing 2 to 6 carbon atoms; haloalkyl containing 1 to 4 carbon atoms; haloalkenyl containing 2 to 8 carbon atoms; and cycloalkyl containing 3 to 6 carbon atoms optionally substituted by one or more substituents selected from alkyl containing 1 to 4 carbon atoms and halogen;

$R^2$ is selected from alkyl containing 1 to 8 carbon atoms; haloalkyl containing 1 to 4 carbon atoms; alkoxy containing 1 to 6 carbon atoms; alkylamino containing 1 to 4 carbon atoms; dialkylamino containing a total of 2 to 8 carbon atoms; halogen; cycloalkyl containing 3 to 6 carbon atoms optionally substituted by one or more substituents selected from halogen and alkyl containing 1 to 4 carbon atoms; and phenyl optionally substituted with one or more substituents selected from alkyl containing 1 to 4 carbon atoms, haloalkyl containing 1 to 4 carbon atoms, halogen and alkoxy containing 1 to 4 carbon atoms;

$R^3$ is selected from hydrogen and halogen;

$R^4$ is the residue of an alcohol of formula $R^4$—OH which forms an insecticidal ester when combined with chrysanthemic acid, permethrin acid or cyhalotrin acid; and X is selected from oxygen and sulphur;

Chrysanthmic acid is 3-(2-methylprop-1-en-1-yl)-2,2-dimethylcyclopropanecarboxylic acid, permethrin acid is 3-(2,2-dichloroethenyl)-2,2-dimethylcyclopropanecarboxylic acid and cyhalothrin acid is 3-(Z-2-chloro-3,3,3-trifluoroprop-1-en-1-yl)-2,2-dimethylcyclopropanecarboxylic acid.

Preferred compounds according to the invention are those according to formula (I) wherein $R^1$, $R^2$, $R^3$ and X have any of the meanings given hereinbefore, and $R^4$ is selected from:

(i) a group of formula:

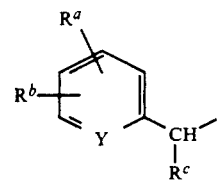

wherein Y represents nitrogen, or carbon substituted with either of a hydrogen atom or a methyl group, $R^a$ represents hydrogen, halogen or methyl, $R^b$ represents phenyl, phenoxy, halophenoxy, benzyl or halogen, and $R^c$ represents hydrogen, methyl, trifluoromethyl, cyano or ethynyl;

(ii) a group of formula:

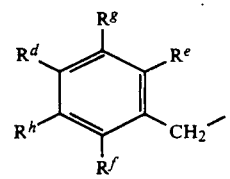

wherein:

$R^d$ is selected from halogen; alkyl containing 1 to 8 carbon atoms; alkenyl containing 1 to 8 carbon atoms; alkynyl containing 1 to 8 carbon atoms; haloalkyl containing 1 to 6 carbon atoms; haloalkenyl containing 1 to 6 carbon atoms; a group of formula —SiR$_3$; a group of formula —CO$_2$R; a group of formula —OR; a group of formula —SR; a group of formula —(CH$_2$)$_3$—R$^h$ where R$^h$ represents chlorine, hydroxy, cyano, a group of formula —BR$_2$, or a group of formula —SiR$_3$; and a group of formula —CH$_2$R$^i$ where R$^i$ represents hydroxy, halogen, a group of formula —OR, a group of formula —SR, alkenyloxy containing 2 to 4 carbon atoms, alkenylthio containing 2 to 4 carbon atoms, alkynyloxy containing 2 to 4 carbon atoms, alkynylthio containing 2 to 4 carbon atoms, phenyl optionally substituted with one or more halogen substituents, phenoxy optionally substituted with one or more halogen substituents, phenylthio optionally substituted with one or more halogen substituents, benzyloxy optionally substituted with one or more halogen substituents, a group of formula —OCOR, a group of formula —OCOOR, a group of formula —O—N=CR$_2$, a group of formula —NR$_2$, piperidin-1-yl, pyrollidin-1-yl, N-morpholino, or cyclopropyl optionally substituted with one or more halogen substituents, wherein R represents alkyl containing 1 to 4 carbon atoms;

$R^e$, $R^f$, $R^g$ and $R^h$ are independently selected from hydrogen, fluorine, chlorine, bromine, piperidin-1-yl, pyrollidin-1-yl, alkyl containing 1 to 4 carbon atoms, alkoxy containing 1 to 4 carbon atoms, alkylthio containing 1 to 4 carbon atoms, and a group of formula —NR$_2$ wherein R represents alkyl containing 1 to 4 carbon atoms;

(iii) a group of formula:

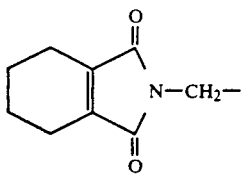

and
(iv) a group of formula:

wherein Z is selected from oxygen and sulphur, $R^j$ is selected from hydrogen, alkyl containing 1 to 6 carbon atoms, alkenyl containing 1 to 6 carbon atoms, alkynyl containing 1 to 6 carbon atoms, and benzyl, and $R^k$ is selected from alkyl containing 1 to 6 carbon atoms, alkenyl containing 1 to 6 carbon atoms, alkynyl containing 1 to 6 carbon atoms, and benzyl.

Preferred values of $R^1$ in the compounds of formula (I) according to the invention include ethyl, 1-methylethyl, 1,1-dimethylethyl, 1,1-dimethylpropyl, 1,1-dimethylprop-2-en-1-yl, trifluoromethyl, cyclopropyl, 1-methylcyclopropyl, 2-methylprop-2-en-1-yl, 2-fluoro-1,1-dimethylethyl, 2,2-difluoro-1,1-dimethylethyl, prop-1-en-2-yl, and prop-2-en-1-yl.

Preferred values of $R^2$ include methyl, ethyl, 1-methylethyl, 1,1-dimethylethyl, 1,1-dimethylpropyl, trifluoromethyl, 2-fluoro-1,1-dimethylethyl, 2,2-difluoro-1,1-dimethylethyl, trichloromethyl, cyclopropyl, 1-methylcyclopropyl, cyclohexyl, 1-methylcyclohexyl, phenyl, 2-chlorophenyl, dimethylamino and chloro.

Preferred values of $R^3$ include hydrogen, chlorine and fluorine.

Preferred values of R4 include either (i) a group of formula:

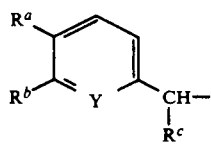

wherein $R^a$ is selected from hydrogen and fluorine; $R^b$ is selected from benzyl, phenoxy, 4-chlorophenoxy, 4-bromophenoxy and 4-fluorophenoxy; $R^c$ is selected from hydrogen, methyl, trifluoromethyl, ethynyl and cyano; and Y represents nitrogen or carbon substituted with either of a hydrogen atom or a methyl group; or (ii) the group of formula:

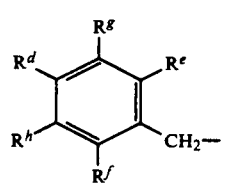

wherein $R^d$ has any of the meanings given hereinbefore; $R^e$ is selected from fluorine, chlorine, bromine, methyl, ethyl, methoxy, ethoxy, methylthio, ethylthio and dimethylamino; $R^f$ is selected from hydrogen and fluorine; and $R^g$ and $R^h$ are independently selected from fluorine, chlorine, bromine, methoxy, ethoxy, methyl and ethyl.

Particularly preferred esters of formula (I) according to the invention are those derived from the following acids or simple derivatives thereof by the processes described hereinafter:

2-[2-(1,1-dimethylethyl)pyrimidin-5-yl]-3,3-dimethylbutanoic acid and stereoisomers thereof, 2-[2-(1-methylethyl)pyrimidin-5-yl]-3,3-dimethylbutanoic acid and stereoisomers thereof, 2-[2-(1-methylcyclopropyl)pyrimidin-5-yl]-3,3-dimethylbutanoic acid and stereoisomers thereof, 2-[2-(1,1-dimethylpropyl)pyrimidin-5-yl]-3,3-dimethylbutanoic acid and stereoisomers thereof, 2-[2-(trifluoromethyl)pyrimidin-5-yl]-3,3-dimethylbutanoic acid and stereoisomers thereof, 2-[2-(1,1-dimethylethyl)pyrimidin-5-yl]-3,3-dimethylpent-4-enoic acid and stereoisomers thereof, 2-[2-(1,1-dimethylethyl)pyrimidin-5-yl]butanoic acid and stereoisomers thereof, 2-[2-(dimethylamino)pyrimidin-5-yl]-3,3-dimethylbutanoic acid and stereoisomers thereof, 2-[2-(cyclopropyl)pyrimidin-5-yl]-3,3-dimethylbutanoic acid and stereoisomers thereof, 2-[2-phenylpyrimidin-5-yl]-3,3-dimethylbutanoic acid and stereoisomers thereof, 2-[2-(4-methoxyphenyl)pyrimidin-5-yl]-3,3-dimethylbutanoic acid and stereoisomers thereof, 2-[2-(1,1-dimethylethyl)pyrimidin-5-yl]-3-methylbut-3-enoic acid and stereoisomers thereof, 2-[2-methylpyrimidin-5-yl]-3,3-dimethylbutanoic acid and stereoisomers thereof, 2-[2-(1-methylcyclohexyl)pyrimidin-5-yl]-3,3-dimethylbutanoic acid and stereoisomers thereof, 2-[2-(2-chlorophenyl)pyrimidin-5-yl]-3,3-dimethylbutanoic acid and stereoisomers thereof, 2-[2-(1,1-dimethylethyl)pyrimidin-5-yl]-3,3-dimethylpentanoic acid and stereoisomers thereof, 2-[2-(1,1-dimethylethyl)pyrimidin-5-yl]pent-4-enoic acid and stereoisomers thereof, 2-[2-(1,1-dimethylethyl)pyrimidin-5-yl]-3,3,3-trifluoropropanoic acid and stereoisomers thereof, 2-[2-(1,1-dimethylethyl)pyrimidin-5-yl]-2-cyclopropylacetic acid and stereoisomers thereof, 2-[2-phenylpyrimidin-5-yl]-3-methylbutanoic acid and stereoisomers thereof, 2-[2-(trifluoromethyl)pyrimidin-5-yl]-3-methylbutanoic acid and stereoisomers thereof, 2-[2-(dimethylamino)pyrimidin-5-yl]-3-methylbutanoic acid and stereoisomers thereof, 2-[2-(trichloromethyl)pyrimidin-5-yl]-3-methylbutanoic acid and stereoisomers thereof, 2-[2-chloropyrimidin-5-yl]-3-methylbutanoic acid and stereoisomers thereof, 2-[2-methylpyrimidin-5-yl]-2-methylbutanoic acid and stereoisomers thereof, 2-[2-(trifluoromethyl)pyrimidin-5-yl]-2-(1-methylcyclopropyl)acetic acid and stereoisomers thereof, 2-[2-(1,1-dimethylethyl)pyrimidin-5-yl]-2-(1-methylcyclopropyl)acetic acid and stereoisomers thereof, 2-[2-(trifluoromethyl)pyrimidin-5-yl]-3,3-dimethylpentanoic acid and stereoisomers thereof, 2-[2-(trichloromethyl)pyrimidin-5-yl]-3,3-dimethylbutanoic acid and stereoisomers thereof, 2-[2-chloropyrimidin-5-yl]-3,3-dimethylbutanoic acid and stereoisomers thereof, and 2-[2-(1,1-dimethylethyl)pyrimidin-5-yl]-3,3-dimethylbutanethioic acid and stereoisomers thereof.

It will be appreciated that the compounds of formula I are capable of existing in different isomeric forms exhibiting differing levels of insecticidal and acaricidal activity, and as mixtures of such isomers. Thus optical isomerism arises from the presence of one or more chiral centres leading to the possibility of stereoisomers or diastereoisomers. In addition the possibility of geometrical isomerism arises where a compound according to the invention contains one or more substituted alkenyl groups. All such individual isomeric forms and mixtures thereof, including racemic mixtures are within the scope of the invention.

Particular examples of compounds according to the invention useful as acaricides and insecticides are those set out in Table I below and stereoisomers thereof. The compounds correspond to the formula (I) and the meanings of $R^1$, $R^2$, $R^3$, $R^4$ and X are given for each compound. In Table I, $R^4$ is defined as a group E-01 to E-32, the meanings of which are set out as follows:

E-01 = 3-phenoxybenzyl
E-02 = 1-cyano-1-(3-phenoxyphenyl)methyl
E-03 = 2-methyl-3-phenylbenzyl
E-04 = 4-methyl-2,3,5,6-tetrafluorobenzyl
E-05 = 4-(prop-2-en-1-yl)-2,3,5,6-tetrafluorobenzyl
E-06 = N-3,4,5,6-tetrahydrophthalimidomethyl
E-07 = 1-ethynyl-1-(3-phenoxyphenyl)methyl
E-08 = 5-benzylfur-3-ylmethyl
E-09 = 6-phenoxypyrid-2-ylmethyl
E-10 = 1-cyano-1-(6-phenoxypyrid-2-yl)methyl
E-11 = 1-(6-phenoxypyrid-2-yl)ethyl
E-12 = 4-(prop-2-yn-1-yl)-2,3,5,6-tetrafluorobenzyl
E-13 = 4-(but-2-yn-1-yl)-2,3,5,6-tetrafluorobenzyl
E-14 = 4-(3-chloroprop-2-en-1-yl)-2,3,5,6-tetrafluorobenzyl
E-15 = 4-(methoxymethyl)-2,3,5,6-tetrafluorobenzyl
E-16 = 2-methoxy-4-(methoxymethyl)-3,5,6-trifluorobenzyl
E-17 = 4-benzyl-2,3,5,6-tetrafluorobenzyl
E-18 = 3-benzyl-4-fluorobenzyl
E-19 = 4-[3-(trimethylsilyl)prop-2-yn-1-yl]-2,3,5,6-tetrafluorobenzyl
E-20 = 4-(2-methylprop-2-en-1-yl)-2,3,5,6-tetrafluorobenzyl
E-21 = 4-ethoxy-2,3,5,6-tetrafluorobenzyl
E-22 = 4-trimethylsilyl-2,3,5,6-tetrafluorobenzyl
E-23 = 4-(but-2-en-1-yl)-2,3,5,6-tetrafluorobenzyl
E-24 = 4-(2-chloroprop-2-en-1-yl)-2,3,5,6-tetrafluorobenzyl
E-25 = 4-fluoro-3-phenoxybenzyl
E-26 = 2-chloro-6-fluorobenzyl
E-27 = 1-cyano-1-(3-benzyl-4-fluorophenyl)methyl
E-28 = 3-phenylaminobenzyl
E-29 = 4-(2,3-dichloroprop-2-en-1-yl)-2,3,5,6-tetrafluorobenzyl
E-30 = pentafluorobenzyl
E-31 = 1-cyano-1-(4-fluoro-2-phenoxyphenyl)methyl
E-32 = 2,2,2-trifluoro-1-(6-phenoxypyrid-2-yl)ethyl
E-33 = 2,3,5,6-tetrafluoro-4-[4-chlorobenzyloxy)methyl]benzyl
E-34 = 2,3,5,6-tetrafluoro-4-(hydroxymethyl)benzyl
E-35 = 2,3,5,6-tetrafluoro-4-[((1,1-dimethylethyl)oxycarbonyl)methoxymethyl]benzyl
E-36 = 2,3,5,6-tetrafluoro-4-(acetyloxymethyl)benzyl
E-37 = 2,3,5,6-tetrafluoro-4-(chloromethyl)benzyl
E-38 = 2,3,5,6-tetrafluoro-4-(n-propyl)benzyl
E-39 = 2,3,5,6-tetrafluoro-4-(methythiomethyl)benzyl
E-40 = 2,3,5,6-tetrafluoro-4-(ethoxycarbonyl)benzyl
E-41 = 2,3,5,6-tetrafluoro-4-[(1-methylethyl)oxycarbonyl]benzyl
E-42 = 2,3,5,6-tetrafluoro-4-[(2,2-dimethylpropanoyl)oxymethyl]benzyl
E-43 = 2,3,5,6-tetrafluoro-4-[(2-methylpropanoyl)oxymethyl]benzyl
E-44 = 2,3,5,6-tetrafluoro-4-[(1-methylethyl)thiomethyl]benzyl
E-45 = 2,3,5,6-tetrafluoro-4-[(1,1-dimethylethyl)thiomethyl]benzyl
E-46 = 2,3,5,6-tetrafluoro-4-(N,N-diethylaminomethyl)benzyl
E-47 = 2,3,5,6-tetrafluoro-4-[(piperidin-1-yl)methyl]benzyl
E-48 = 2,3,5,6-tetrafluoro-4-[(N-prop-2-ylideneamino)oxymethyl]benzyl
E-49 = 2,3,5,6-tetrafluoro-4-(cyclopropylmethyl)benzyl
E-50 = 3-(4-chlorophenoxy)benzyl
E-51 = 1-[3-(4-chlorophenoxy)pyrid-2-yl]ethyl
E-52 = 3,5-difluoro-4-methyl-2-(methylthio)benzyl
E-53 = 2,3,5,6-tetrafluoro-4-(methylthio)benzyl
E-54 = 2,3,5,6-tetrafluoro-4-(ethylthio)benzyl
E-55 = 2-ethoxy-4-(methoxymethyl)-3,5,6-trifluorobenzyl
E-56 = 2,3,5,6-tetrafluoro-4-(ethoxymethyl)benzyl
E-57 = 2-methoxy-4-(ethoxymethyl)-3,5,6-trifluorobenzyl
E-58 = 2-ethoxy-4-(ethoxymethyl)-3,5,6-trifluorobenzyl
E-59 = 2,3,5,6-tetrafluoro-[1-methylethyl)oxymethyl]benzyl
E-60 = 2-methoxy-4-[(1-methylethyl)oxymethyl]-3,5,6-trifluorobenzyl
E-61 = 2-ethoxy-4-[(1-methylethyl)oxymethyl]-3,5,6-trifluorobenzyl
E-62 = 2,3,5,6-tetrafluoro-4-(phenoxymethyl)benzyl
E-63 = 2-methoxy-4-(phenoxymethyl)-3,5,6-trifluorobenzyl
E-64 = 2-ethoxy-4-(phenoxymethyl)-3,5,6-trifluorobenzyl
E-65 = 2,3,5,6-tetrafluoro-4-[(2,2-dichlorocyclopropyl)methyl]benzyl
E-66 = 2,5,6-trifluoro-3-methoxy-4-(methoxymethyl)benzyl
E-67 = 2,3,5,6-tetrafluoro-4-[3-(triethylsilyl)prop-1-yl]benzyl
E-68 = 2-methyl-3,4,5,6-tetrafluorobenzyl
E-69 = 2,3,5,6-tetrafluoro-4-[(prop-2-yn-1-yl)thiomethyl]benzyl

TABLE I

| COMPOUND NO | $R^1$ | $R^2$ | $R^3$ | X | $R^4$ |
| --- | --- | --- | --- | --- | --- |
| 1 | $(CH_3)_3C$ | $(CH_3)_3C$ | H | 0 | E-01 |
| 2 | $(CH_3)_3C$ | $(CH_3)_3C$ | H | 0 | E-02 |
| 3 | $(CH_3)_3C$ | $(CH_3)_3C$ | H | 0 | E-03 |
| 4 | $(CH_3)_3C$ | $(CH_3)_3C$ | H | 0 | E-04 |
| 5 | $(CH_3)_3C$ | $(CH_3)_3C$ | H | 0 | E-05 |

TABLE I-continued

| COMPOUND NO | R¹ | R² | R³ | X | R⁴ |
|---|---|---|---|---|---|
| 6 | (CH₃)₃C | (CH₃)₃C | H | 0 | E-06 |
| 7 | (CH₃)₃C | (CH₃)₃C | H | 0 | E-07 |
| 8 | (CH₃)₃C | (CH₃)₃C | H | 0 | E-08 |
| 9 | (CH₃)₃C | (CH₃)₃C | H | 0 | E-09 |
| 10 | (CH₃)₃C | (CH₃)₃C | H | 0 | E-10 |
| 11 | (CH₃)₃C | (CH₃)₃C | H | 0 | E-11 |
| 12 | (CH₃)₃C | (CH₃)₃C | H | 0 | E-12 |
| 13 | (CH₃)₃C | (CH₃)₃C | H | 0 | E-13 |
| 14 | (CH₃)₃C | (CH₃)₃C | H | 0 | E-14 |
| 15 | (CH₃)₃C | (CH₃)₃C | H | 0 | E-15 |
| 16 | (CH₃)₃C | (CH₃)₃C | H | 0 | E-16 |
| 17 | (CH₃)₃C | (CH₃)₃C | H | 0 | E-17 |
| 18 | (CH₃)₃C | (CH₃)₃C | H | 0 | E-18 |
| 19 | (CH₃)₃C | (CH₃)₃C | H | 0 | E-19 |
| 20 | (CH₃)₃C | (CH₃)₃C | H | 0 | E-20 |
| 21 | (CH₃)₃C | (CH₃)₃C | H | 0 | E-21 |
| 22 | (CH₃)₃C | (CH₃)₃C | H | 0 | E-22 |
| 23 | (CH₃)₃C | (CH₃)₃C | H | 0 | E-23 |
| 24 | (CH₃)₃C | (CH₃)₃C | H | 0 | E-24 |
| 25 | (CH₃)₃C | (CH₃)₃C | H | 0 | E-25 |
| 26 | (CH₃)₃C | (CH₃)₃C | H | 0 | E-26 |
| 27 | (CH₃)₃C | (CH₃)₃C | H | 0 | E-27 |
| 28 | (CH₃)₃C | (CH₃)₃C | H | 0 | E-28 |
| 29 | (CH₃)₃C | (CH₃)₃C | H | 0 | E-29 |
| 30 | (CH₃)₃C | (CH₃)₃C | H | 0 | E-30 |
| 31 | (CH₃)₃C | (CH₃)₃C | H | 0 | E-31 |
| 32 | (CH₃)₃C | (CH₃)₃C | H | 0 | E-32 |
| 33 | (CH₃)₃C | CF₃ | H | 0 | E-04 |
| 34 | (CH₃)₃C | CF₃ | H | 0 | E-05 |
| 35 | (CH₃)₃C | CF₃ | H | 0 | E-09 |
| 36 | (CH₃)₃C | CF₃ | H | 0 | E-10 |
| 37 | (CH₃)₃C | CF₃ | H | 0 | E-11 |
| 38 | (CH₃)₃C | CF₃ | H | 0 | E-12 |
| 39 | (CH₃)₃C | CF₃ | H | 0 | E-13 |
| 40 | (CH₃)₃C | CF₃ | H | 0 | E-14 |
| 41 | (CH₃)₃C | CF₃ | H | 0 | E-15 |
| 42 | (CH₃)₃C | CF₃ | H | 0 | E-16 |
| 43 | (CH₃)₃C | CF₃ | H | 0 | E-17 |
| 44 | (CH₃)₃C | CF₃ | H | 0 | E-18 |
| 45 | (CH₃)₃C | CF₃ | H | 0 | E-20 |
| 46 | (CH₃)₃C | CF₃ | H | 0 | E-23 |
| 47 | (CH₃)₃C | CF₃ | H | 0 | E-24 |
| 48 | (CH₃)₃C | CF₃ | H | 0 | E-25 |
| 49 | (CH₃)₃C | CF₃ | H | 0 | E-26 |
| 50 | (CH₃)₃C | CF₃ | H | 0 | E-29 |
| 51 | (CH₃)₃C | CF₃ | H | 0 | E-30 |
| 52 | (CH₃)₃C | CF₃ | H | 0 | E-31 |
| 53 | (CH₃)₃C | CH₃CH₂(CH₃)₂C | H | 0 | E-04 |
| 54 | (CH₃)₃C | CH₃CH₂(CH₃)₂C | H | 0 | E-05 |
| 55 | (CH₃)₃C | CH₃CH₂(CH₃)₂C | H | 0 | E-09 |
| 56 | (CH₃)₃C | CH₃CH₂(CH₃)₂C | H | 0 | E-10 |
| 57 | (CH₃)₃C | CH₃CH₂(CH₃)₂C | H | 0 | E-11 |
| 58 | (CH₃)₃C | CH₃CH₂(CH₃)₂C | H | 0 | E-12 |
| 59 | (CH₃)₃C | CH₃CH₂(CH₃)₂C | H | 0 | E-13 |
| 60 | (CH₃)₃C | CH₃CH₂(CH₃)₂C | H | 0 | E-14 |
| 61 | (CH₃)₃C | CH₃CH₂(CH₃)₂C | H | 0 | E-15 |
| 62 | (CH₃)₃C | CH₃CH₂(CH₃)₂C | H | 0 | E-16 |
| 63 | (CH₃)₃C | CH₃CH₂(CH₃)₂C | H | 0 | E-17 |
| 64 | (CH₃)₃C | CH₃CH₂(CH₃)₂C | H | 0 | E-18 |
| 65 | (CH₃)₃C | CH₃CH₂(CH₃)₂C | H | 0 | E-20 |
| 66 | (CH₃)₃C | CH₃CH₂(CH₃)₂C | H | 0 | E-23 |
| 67 | (CH₃)₃C | CH₃CH₂(CH₃)₂C | H | 0 | E-24 |
| 68 | (CH₃)₃C | CH₃CH₂(CH₃)₂C | H | 0 | E-25 |
| 69 | (CH₃)₃C | CH₃CH₂(CH₃)₂C | H | 0 | E-26 |
| 70 | (CH₃)₃C | CH₃CH₂(CH₃)₂C | H | 0 | E-29 |
| 71 | (CH₃)₃C | CH₃CH₂(CH₃)₂C | H | 0 | E-30 |
| 72 | (CH₃)₃C | CH₃CH₂(CH₃)₂C | H | 0 | E-31 |
| 73 | (CH₃)₃C | (CH₃)₂CH | H | 0 | E-02 |
| 74 | (CH₃)₃C | (CH₃)₂CH | H | 0 | E-11 |
| 75 | (CH₃)₃C | (CH₃)₂CH | H | 0 | E-12 |
| 76 | (CH₃)₃C | (CH₃)₂CH | H | 0 | E-16 |
| 77 | (CH₃)₃C | cyclopropyl | H | 0 | E-02 |
| 78 | (CH₃)₃C | cyclopropyl | H | 0 | E-11 |
| 79 | (CH₃)₃C | cyclopropyl | H | 0 | E-12 |
| 80 | (CH₃)₃C | cyclopropyl | H | 0 | E-16 |
| 81 | (CH₃)₃C | phenyl | H | 0 | E-02 |
| 82 | (CH₃)₃C | phenyl | H | 0 | E-11 |
| 83 | (CH₃)₃C | phenyl | H | 0 | E-12 |
| 84 | (CH₃)₃C | phenyl | H | 0 | E-16 |
| 85 | (CH₃)₂CH | CF₃ | H | 0 | E-02 |

TABLE I-continued

| COMPOUND NO | R¹ | R² | R³ | X | R⁴ |
|---|---|---|---|---|---|
| 86 | $(CH_3)_2CH$ | $CF_3$ | H | 0 | E-11 |
| 87 | $(CH_3)_2CH$ | $CF_3$ | H | 0 | E-12 |
| 88 | $(CH_3)_2CH$ | $CF_3$ | H | 0 | E-16 |
| 89 | cyclopropyl | $(CH_3)_3C$ | H | 0 | E-02 |
| 90 | cyclopropyl | $(CH_3)_3C$ | H | 0 | E-11 |
| 91 | cyclopropyl | $(CH_3)_3C$ | H | 0 | E-12 |
| 92 | cyclopropyl | $(CH_3)_3C$ | H | 0 | E-16 |
| 93 | cyclopropyl | $CF_3$ | H | 0 | E-02 |
| 94 | cyclopropyl | $CF_3$ | H | 0 | E-11 |
| 95 | cyclopropyl | $CF_3$ | H | 0 | E-12 |
| 96 | cyclopropyl | $CF_3$ | H | 0 | E-16 |
| 97 | 1-methylcyclopropyl | $(CH_3)_3C$ | H | 0 | E-02 |
| 98 | 1-methylcyclopropyl | $(CH_3)_3C$ | H | 0 | E-11 |
| 99 | 1-methylcyclopropyl | $(CH_3)_3C$ | H | 0 | E-12 |
| 100 | 1-methylcyclopropyl | $(CH_3)_3C$ | H | 0 | E-16 |
| 101 | 1-methylcyclopropyl | $CF_3$ | H | 0 | E-02 |
| 102 | 1-methylcyclopropyl | $CF_3$ | H | 0 | E-11 |
| 103 | 1-methylcyclopropyl | $CF_3$ | H | 0 | E-12 |
| 104 | 1-methylcyclopropyl | $CF_3$ | H | 0 | E-16 |
| 105 | $CH_3CH_2(CH_3)_2C$ | $(CH_3)_3C$ | H | 0 | E-02 |
| 106 | $CH_3CH_2(CH_3)_2C$ | $(CH_3)_3C$ | H | 0 | E-11 |
| 107 | $CH_3CH_2(CH_3)_2C$ | $(CH_3)_3C$ | H | 0 | E-12 |
| 108 | $CH_3CH_2(CH_3)_2C$ | $(CH_3)_3C$ | H | 0 | E-16 |
| 109 | $CH_3CH_2(CH_3)_2C$ | $CF_3$ | H | 0 | E-02 |
| 110 | $CH_3CH_2(CH_3)_2C$ | $CF_3$ | H | 0 | E-11 |
| 111 | $CH_3CH_2(CH_3)_2C$ | $CF_3$ | H | 0 | E-12 |
| 112 | $CH_3CH_2(CH_3)_2C$ | $CF_3$ | H | 0 | E-16 |
| 113 | $(CH_3)_2CH$ | phenyl | H | 0 | E-05 |
| 114 | $(CH_3)_2CH$ | $CF_3$ | H | 0 | E-05 |
| 115 | $(CH_3)_2CH$ | $(CH_3)_2N$ | H | 0 | E-05 |
| 116 | $(CH_3)_2CH$ | $CF_3$ | H | 0 | E-15 |
| 117 | $(CH_3)_2CH$ | $CCl_3$ | H | 0 | E-05 |
| 118 | $(CH_3)_2CH$ | Cl | H | 0 | E-15 |
| 119 | $(CH_3)_2CH$ | $CH_3$ | H | 0 | E-05 |
| 120 | $(CH_3)_3C$ | $CH_3$ | H | 0 | E-15 |
| 121 | $C_2H_5$ | $(CH_3)_3C$ | H | 0 | E-31 |
| 122 | $C_2H_5$ | $(CH_3)_3C$ | H | 0 | E-04 |
| 123 | $C_2H_5$ | $(CH_3)_3C$ | H | 0 | E-05 |
| 124 | cyclopropyl | $(CH_3)_3C$ | H | 0 | E-05 |
| 125 | cyclopropyl | $(CH_3)_3C$ | H | 0 | E-25 |
| 126 | $(CH_3)_3C$ | $CH_3$ | H | 0 | E-04 |
| 127 | $(CH_3)_3C$ | $CH_3$ | H | 0 | E-05 |
| 128 | $(CH_3)_3C$ | $CH_3$ | H | 0 | E-30 |
| 129 | $(CH_3)_3C$ | $(CH_3)_2CH$ | H | 0 | E-04 |
| 130 | $(CH_3)_3C$ | $(CH_3)_2CH$ | H | 0 | E-05 |
| 131 | $(CH_3)_3C$ | $(CH_3)_2CH$ | H | 0 | E-15 |
| 132 | $(CH_3)_3C$ | $(CH_3)_2CH$ | H | 0 | E-30 |
| 133 | $(CH_3)_3C$ | cyclopropyl | H | 0 | E-04 |
| 134 | $(CH_3)_3C$ | cyclopropyl | H | 0 | E-05 |
| 135 | $(CH_3)_3C$ | cyclopropyl | H | 0 | E-15 |
| 136 | $(CH_3)_3C$ | cyclopropyl | H | 0 | E-30 |
| 137 | $(CH_3)_3C$ | 1-methylcyclopropyl | H | 0 | E-04 |
| 138 | $(CH_3)_3C$ | 1-methylcyclopropyl | H | 0 | E-05 |
| 139 | $(CH_3)_3C$ | 1-methylcyclopropyl | H | 0 | E-15 |
| 140 | $(CH_3)_3C$ | 1-methylcyclopropyl | H | 0 | E-30 |
| 141 | $(CH_3)_3C$ | $CH_3CH_2(CH_3)_2C$ | H | 0 | E-01 |
| 142 | $(CH_3)_3C$ | $CH_3CH_2(CH_3)_2C$ | H | 0 | E-21 |
| 143 | $(CH_3)_3C$ | $CH_3CH_2(CH_3)_2C$ | H | 0 | E-22 |
| 144 | $(CH_3)_3C$ | $CH_3CH_2(CH_3)_2C$ | H | 0 | E-27 |
| 145 | $(CH_3)_3C$ | $CCl_3$ | H | 0 | E-02 |
| 146 | $(CH_3)_3C$ | $CCl_3$ | H | 0 | E-04 |
| 147 | $(CH_3)_3C$ | $CCl_3$ | H | 0 | E-05 |
| 148 | $(CH_3)_3C$ | $CCl_3$ | H | 0 | E-11 |
| 149 | $(CH_3)_3C$ | $CCl_3$ | H | 0 | E-12 |
| 150 | $(CH_3)_3C$ | $CCl_3$ | H | 0 | E-15 |
| 151 | $(CH_3)_3C$ | $CCl_3$ | H | 0 | E-16 |
| 152 | $(CH_3)_3C$ | Cl | H | 0 | E-02 |
| 153 | $(CH_3)_3C$ | Cl | H | 0 | E-04 |
| 154 | $(CH_3)_3C$ | Cl | H | 0 | E-05 |
| 155 | $(CH_3)_3C$ | Cl | H | 0 | E-11 |
| 156 | $(CH_3)_3C$ | Cl | H | 0 | E-15 |
| 157 | $(CH_3)_3C$ | Cl | H | 0 | E-16 |
| 158 | $(CH_3)_3C$ | Cl | H | 0 | E-30 |
| 159 | $(CH_3)_3C$ | phenyl | H | 0 | E-04 |
| 160 | $(CH_3)_3C$ | phenyl | H | 0 | E-05 |
| 161 | $(CH_3)_3C$ | phenyl | H | 0 | E-15 |
| 162 | $(CH_3)_3C$ | phenyl | H | 0 | E-30 |
| 163 | $(CH_3)_3C$ | $(CH_3)_3C$ | H | 0 | E-33 |
| 164 | $(CH_3)_3C$ | $(CH_3)_3C$ | H | 0 | E-34 |
| 165 | $(CH_3)_3C$ | $(CH_3)_3)$ | H | 0 | E-35 |

TABLE I-continued

| COMPOUND NO | R¹ | R² | R³ | X | R⁴ |
|---|---|---|---|---|---|
| 166 | (CH₃)₃C | (CH₃)₃) | H | 0 | E-36 |
| 167 | (CH₃)₃C | (CH₃)₃) | H | 0 | E-37 |
| 168 | (CH₃)₃C | (CH₃)₃) | H | 0 | E-38 |
| 169 | (CH₃)₃C | (CH₃)₃) | H | 0 | E-39 |
| 170 | (CH₃)₃C | (CH₃)₃) | H | 0 | E-40 |
| 171 | (CH₃)₃C | (CH₃)₃) | H | 0 | E-41 |
| 172 | (CH₃)₃C | (CH₃)₃) | H | 0 | E-42 |
| 173 | (CH₃)₃C | (CH₃)₃) | H | 0 | E-43 |
| 174 | (CH₃)₃C | (CH₃)₃) | H | 0 | E-44 |
| 175 | (CH₃)₃C | (CH₃)₃) | H | 0 | E-45 |
| 176 | (CH₃)₃C | (CH₃)₃) | H | 0 | E-46 |
| 177 | (CH₃)₃C | (CH₃)₃) | H | 0 | E-47 |
| 178 | (CH₃)₃C | (CH₃)₃) | H | 0 | E-48 |
| 179 | (CH₃)₃C | (CH₃)₃C | H | 0 | E-49 |
| 180 | (CH₃)₃C | (CH₃)₃C | H | 0 | E-50 |
| 181 | (CH₃)₃C | (CH₃)₃C | H | 0 | E-51 |
| 182 | (CH₃)₃C | (CH₃)₃C | H | 0 | E-52 |
| 183 | (CH₃)₃C | (CH₃)₃C | H | 0 | E-53 |
| 184 | (CH₃)₃C | (CH₃)₃C | H | 0 | E-54 |
| 185 | (CH₃)₃C | (CH₃)₃C | H | 0 | E-55 |
| 186 | (CH₃)₃C | (CH₃)₃C | H | 0 | E-56 |
| 187 | (CH₃)₃C | (CH₃)₃C | H | 0 | E-57 |
| 188 | (CH₃)₃C | (CH₃)₃C | H | 0 | E-58 |
| 189 | (CH₃)₃C | (CH₃)₃C | H | 0 | E-59 |
| 190 | (CH₃)₃C | (CH₃)₃C | H | 0 | E-60 |
| 191 | (CH₃)₃C | (CH₃)₃C | H | 0 | E-61 |
| 192 | (CH₃)₃C | (CH₃)₃C | H | 0 | E-62 |
| 193 | (CH₃)₃C | (CH₃)₃C | H | 0 | E-63 |
| 194 | (CH₃)₃C | (CH₃)₃C | H | 0 | E-64 |
| 195 | (CH₃)₃C | (CH₃)₃C | H | 0 | E-15 |
| 196 | (CH₃)₃C | (CH₃)₃C | H | 0 | E-34 |
| 197 | (CH₃)₃C | (CH₃)₂CH | H | 0 | E-25 |
| 198 | (CH₃)₃C | (CH₃)₂N | H | 0 | E-11 |
| 199 | (CH₃)₃C | (CH₃)₂N | H | 0 | E-15 |
| 200 | (CH₃)₃C | (CH₃)₂N | H | 0 | E-25 |
| 201 | (CH₃)₃C | cyclopropyl | H | 0 | E-25 |
| 202 | prop-1-en-2-yl | (CH₃)₃C | H | 0 | E-15 |
| 203 | (CH₃)₃C | 1-methylcyclopropyl | H | 0 | E-11 |
| 204 | (CH₃)₃C | 1-methylcyclopropyl | H | 0 | E-25 |
| 205 | (CH₃)₃C | CH₃ | H | 0 | E-11 |
| 206 | (CH₃)₃C | CH₃ | H | 0 | E-25 |
| 207 | (CH₃)₃C | 1-methylcyclohexyl | H | 0 | E-15 |
| 208 | (CH₃)₃C | 2-chlorophenyl | H | 0 | E-15 |
| 209 | (CH₃)₃C | 2-chlorophenyl | H | 0 | E-25 |
| 210 | CH₃CH₂(CH₃)₂C | (CH₃)₃C | H | 0 | E-15 |
| 211 | (CH₂=CH)(CH₃)₂C | (CH₃)₃C | H | 0 | E-15 |
| 212 | CH₂=CHCH₂ | (CH₃)₃C | H | 0 | E-15 |
| 213 | CF₃ | (CH₃)₃C | H | 0 | E-15 |
| 214 | (CH₃)₂CH | CH₃ | H | 0 | E-15 |
| 216 | (CH₃)₃C | (CH₃)₃C | H | 0 | E-65 |
| 217 | (CH₃)₃C | (CH₃)₃C | H | 0 | E-66 |
| 218 | (CH₃)₃C | (CH₃)₃C | H | 0 | E-67 |
| 219 | (CH₃)₃C | (CH₃)₃C | H | 0 | E-68 |
| 220 | (CH₃)₃C | (CH₃)₃C | H | 0 | E-69 |
| 221 | (CH₃)₃C | (CH₃)₃C | H | 0 | E-11 |
| 222 | (CH₃)₃C | (CH₃)₃C | H | 0 | E-32 |
| 223 | (CH₃)₃C | (CH₃)₃C | H | 0 | E-51 |
| 224 | (CH₃)₃C | (CH₃)₂CH | H | 0 | E-56 |
| 225 | (CH₃)₃C | (CH₃)₂CH | H | 0 | E-57 |
| 226 | (CH₃)₃C | (CH₃)₂CH | H | 0 | E-58 |
| 227 | prop-1-en-2-yl | (CH₃)₃C | H | 0 | E-04 |
| 228 | prop-1-en-2-yl | (CH₃)₃C | H | 0 | E-05 |
| 229 | prop-1-en-2-yl | (CH₃)₃C | H | 0 | E-12 |
| 230 | prop-1-en-2-yl | (CH₃)₃C | H | 0 | E-16 |
| 231 | prop-1-en-2-yl | (CH₃)₃C | H | 0 | E-56 |
| 232 | prop-1-en-2-yl | (CH₃)₃C | H | 0 | E-57 |
| 233 | prop-1-en-2-yl | (CH₃)₃C | H | 0 | E-58 |
| 234 | (CH₃)₃C | 1-methylcyclopropyl | H | 0 | E-12 |
| 235 | (CH₃)₃C | 1-methylcyclopropyl | H | 0 | E-16 |
| 236 | (CH₃)₃C | 1-methylcyclopropyl | H | 0 | E-56 |
| 237 | (CH₃)₃C | 1-methylcyclopropyl | H | 0 | E-57 |
| 238 | (CH₃)₃C | 1-methylcyclopropyl | H | 0 | E-58 |
| 239 | (CH₃)₃C | CH₃ | H | 0 | E-12 |
| 240 | (CH₃)₃C | CH₃CH₂(CH₃)₂C | H | 0 | E-56 |
| 241 | (CH₃)₃C | CH₃CH₂(CH₃)₂C | H | 0 | E-57 |
| 242 | (CH₃)₃C | CH₃CH₂(CH₃)₂C | H | 0 | E-58 |
| 243 | (CH₃)₃C | CF₃ | H | 0 | E-39 |
| 244 | (CH₃)₃C | CF₃ | H | 0 | E-56 |
| 245 | (CH₃)₃C | CF₃ | H | 0 | E-57 |
| 246 | (CH₃)₃C | CF₃ | H | 0 | E-58 |

TABLE I-continued

| COMPOUND NO | $R^1$ | $R^2$ | $R^3$ | X | $R^4$ |
| --- | --- | --- | --- | --- | --- |
| 247 | $(CH_3)_3C$ | 1-methylcyclohexyl | H | 0 | E-05 |
| 248 | $(CH_3)_3C$ | 1-methylcyclohexyl | H | 0 | E-11 |
| 249 | $(CH_3)_3C$ | 1-methylcyclohexyl | H | 0 | E-12 |
| 250 | $(CH_3)_3C$ | 1-methylcyclohexyl | H | 0 | E-16 |
| 251 | $(CH_3)_3C$ | 1-methylcyclohexyl | H | 0 | E-27 |
| 252 | $(CH_3)_3C$ | 1-methylcyclohexyl | H | 0 | E-31 |
| 253 | $(CH_3)_3C$ | 1-methylcyclohexyl | H | 0 | E-56 |
| 254 | $(CH_3)_3C$ | 1-methylcyclohexyl | H | 0 | E-57 |
| 255 | $(CH_3)_3C$ | 1-methylcyclohexyl | H | 0 | E-58 |
| 256 | $CH_3CH_2(CH_3)_2C$ | $(CH_3)_3C$ | H | 0 | E-05 |
| 257 | $CH_3CH_2(CH_3)_2C$ | $(CH_3)_3C$ | H | 0 | E-11 |
| 258 | $CH_3CH_2(CH_3)_2C$ | $(CH_3)_3C$ | H | 0 | E-55 |
| 259 | $CH_3CH_2(CH_3)_2C$ | $(CH_3)_3C$ | H | 0 | E-56 |
| 260 | $CH_3CH_2(CH_3)_2C$ | $(CH_3)_3C$ | H | 0 | E-57 |
| 261 | $(CH_2=CH)(CH_3)_2C$ | $(CH_3)_3C$ | H | 0 | E-04 |
| 262 | $(CH_2=CH)(CH_3)_2C$ | $(CH_3)_3C$ | H | 0 | E-05 |
| 263 | $(CH_2=CH)(CH_3)_2C$ | $(CH_3)_3C$ | H | 0 | E-11 |
| 264 | $(CH_2=CH)(CH_3)_2C$ | $(CH_3)_3C$ | H | 0 | E-12 |
| 265 | $(CH_2=CH)(CH_3)_2C$ | $(CH_3)_3C$ | H | 0 | E-14 |
| 266 | $(CH_2=CH)(CH_3)_2C$ | $(CH_3)_3C$ | H | 0 | E-16 |
| 267 | $(CH_2=CH)(CH_3)_2C$ | $(CH_3)_3C$ | H | 0 | E-22 |
| 268 | $(CH_2=CH)(CH_3)_2C$ | $(CH_3)_3C$ | H | 0 | E-23 |
| 269 | $(CH_2=CH)(CH_3)_2C$ | $(CH_3)_3C$ | H | 0 | E-30 |
| 270 | $(CH_2=CH)(CH_3)_2C$ | $(CH_3)_3C$ | H | 0 | E-32 |
| 271 | $(CH_2=CH)(CH_3)_2C$ | $(CH_3)_3C$ | H | 0 | E-34 |
| 272 | $(CH_2=CH)(CH_3)_2C$ | $(CH_3)_3C$ | H | 0 | E-39 |
| 273 | $(CH_2=CH)(CH_3)_2C$ | $(CH_3)_3C$ | H | 0 | E-49 |
| 274 | $(CH_2=CH)(CH_3)_2C$ | $(CH_3)_3C$ | H | 0 | E-55 |
| 275 | $(CH_2=CH)(CH_3)_2C$ | $(CH_3)_3C$ | H | 0 | E-56 |
| 276 | $(CH_2=CH)(CH_3)_2C$ | $(CH_3)_3C$ | H | 0 | E-58 |
| 277 | 1-methylcyclopropyl | $(CH_3)_3C$ | H | 0 | E-15 |
| 278 | $(CH_2F)(CH_3)_2C$ | $(CH_3)_3C$ | H | 0 | E-04 |
| 279 | $(CH_2F)(CH_3)_2C$ | $(CH_3)_3C$ | H | 0 | E-05 |
| 280 | $(CH_2F)(CH_3)_2C$ | $(CH_3)_3C$ | H | 0 | E-14 |
| 281 | $(CH_2F)(CH_3)_2C$ | $(CH_3)_3C$ | H | 0 | E-15 |
| 282 | $(CH_2F)(CH_3)_2C$ | $(CH_3)_3C$ | H | 0 | E-16 |
| 283 | $(CH_2F)(CH_3)_2C$ | $(CH_3)_3C$ | H | 0 | E-11 |
| 284 | $(CH_2F)(CH_3)_2C$ | $(CH_3)_3C$ | H | 0 | E-12 |
| 285 | $(CH_3)_3C$ | $(CH_2F)(CH_3)_2C$ | H | 0 | E-04 |
| 286 | $(CH_3)_3C$ | $(CH_2F)(CH_3)_2C$ | H | 0 | E-05 |
| 287 | $(CH_3)_3C$ | $(CH_2F)(CH_3)_2C$ | H | 0 | E-14 |
| 288 | $(CH_3)_3C$ | $(CH_2F)(CH_3)_2C$ | H | 0 | E-15 |
| 289 | $(CH_3)_3C$ | $(CH_2F)(CH_3)_2C$ | H | 0 | E-16 |
| 290 | $(CH_3)_3C$ | $(CH_2F)(CH_3)_2C$ | H | 0 | E-11 |
| 291 | $(CH_3)_3C$ | $(CH_2F)(CH_3)_2C$ | H | 0 | E-12 |

The insecticidally and acaricidally active compounds of the invention according to formula (I) wherein X is oxygen are esters, and may be prepared from the corresponding alkyl esters, acids and acid chlorides by conventional esterification processes, such as those described in (a) to (d) below, by way of example.

(a) An acid of formula (II):

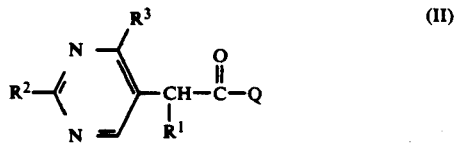

(II)

where Q represents the hydroxy group and $R^1$, $R^2$ and $R^3$ have any of the meanings given hereinabove, may be reacted directly with an alcohol of formula $R^4$—OH (III) where $R^4$ has any of the meanings given hereinabove, the reaction preferably taking place in the presence of an acid catalyst, for example, dry hydrogen chloride, or a dehydrating agent, such as for example, dicyclohexylcarbodiimide or N-ethyl-N-(3-dimethylaminopropyl)carbodiimide, the latter being particularly suitable in those cases where $R^1$ represents t-butyl;

(b) An acid halide of formula (II) where Q represents a halogen atom, preferably a chlorine atom, and $R^1$, $R^2$ and $R^3$ have any of the meanings given hereinabove, may be reacted with an alcohol of formula (III), the reaction preferably taking place in the presence of a base, for example, pyridine, alkali metal hydroxide or carbonate, or alkali metal alkoxide.

(c) An acid of formula (II) where Q represents the hydroxy group or, preferably, an alkali metal salt thereof, may be reacted with either (i) a halide of formula $Q'$—$R^4$ (IV) wherein $Q'$ represents a halogen atom, preferably the chlorine atom, or with a quaternary ammonium salt derived by reaction of such a halide with a tertiary amine, for example pyridine or trialkylamines such as triethylamine, or (ii) with a compound of formula $Q'$—$R^4$ wherein $Q'$ represents the mesylate or tosylate group, and $R^4$ has any of the meanings given hereinabove.

(d) A lower alkyl ester of formula (II) where Q represents a lower alkoxy group containing up to six carbon atoms, preferably the methoxy or ethoxy group, and $R^1$, $R^2$ and $R^3$ have any of the meanings given hereinabove, is heated with an alcohol of formula (III) to effect a transesterification reaction. Preferably the process is performed in the presence of a suitable catalyst, for example, an alkali metal alkoxide, such as sodium methoxide, or an alkylated titanium derivative, such as tetramethyl titanate or tetraethyl titanate.

All of these conventional processes for the preparation of esters may be carried out using solvents and diluents for the various reactants where appropriate, and may be accelerated or lead to higher yields of product when performed at elevated temperatures or in the presence of appropriate catalysts, for example phase-transfer catalysts.

Similarly the interconversion of the acid, acid chloride and lower alkyl esters of Formula II may be performed using conventional chemical procedures for chlorination, esterification and hydrolysis.

The compounds of formula (I) wherein X is sulphur are thioesters and may be prepared by conventional thioesterification processes. Preferred methods include processes analogous to those described for esterification in (a) and (b) above, wherein a thioalcohol of formula $R^4$—SH is used in place of the alcohol of formula $R^4$—OH.

A number of the preferred compounds according to the invention are derivatives of esters of the formula (IA);

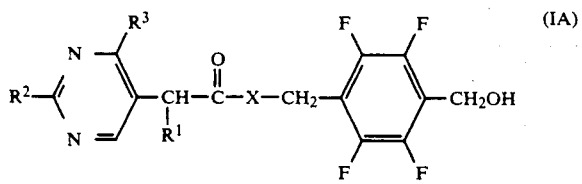

wherein $R^1$, $R^2$, $R^3$ and X have any of the meanings given hereinbefore, and may be conveniently prepared therefrom by conventional alkylation, acylation and halogenation processes, rather than by initial preparation of the fully derivatised alcohol. Further details of such processes are described in the Examples given hereinafter. The compounds of formula (IA) are therefore useful both as insecticidal and acaricidal compounds according to the invention and as intermediates for the synthesis of other compounds according to the invention.

Many of the alcohols of formula $R^4$—OH and thioalcohols of formula $R^4$—SH are well known in the literature and may be prepared by methods described therein; many others may be prepared by closely analogous procedures.

Thus, for example, the preparation of alkyl-tetrafluorobenzyl alcohols, alkenyl-tetrafluorobenzyl alcohols, benzyl-tetrafluorobenzyl alcohols, alkoxy-tetrafluorobenzyl alcohols, alkylthio-tetrafluorobenzyl alcohols and analogues thereof is described in European Patent Application No 31199; the preparation of 4-halomethyl-tetrafluorobenzyl alcohols is described in UK Patent No 2153819; the preparation of alkynyl-tetrafluorobenzyl alcohols is described in European Patent Application No 196156; the preparation of phenoxyalkyl-tetrafluorobenzyl alcohols, alkoxyalkyl-tetrafluorobenzyl alcohols, and dialkylaminoalkyl-tetrafluorobenzyl alcohols is described in European Patent Application No 54360; the preparation of alkoxy-alkoxyalkyl-trifluorobenzyl alcohols is described in UK Patent Application No 2197317; the preparation of 2,6-dihalobenzyl alcohols is described in European Patent Application No 57795; the preparation of 4-fluoro-3-benzylbenzyl alcohols is described in UK Patent Application No 2193959; the preparation of 2,2,2-trifluoro-1-(6-phenoxypyrid-2-yl)ethanol is described in European Patent Application No 223,521; the preparation of other fluorinated benzylalcohols is described in UK Patent Application No 8726875; the preparation of (6-phenoxypyrid-2-yl)methanols and substituted derivatives is described in U.S. Pat. No. 4,256,893 and European Patent Application Nos 112,293, 145,661 and 145,179.

Further examples of the preparation of alcohols useful as intermediates in the preparation of the compounds of formula (I) are given in the Examples hereinafter.

The preparation of individual isomers of the compounds of formula (I) may be carried out in the same manner as described above but commencing from the corresponding individual isomers of compounds of formula II. These may be obtained by conventional isomer separation techniques from mixtures of isomers. Thus the various optically active species may be obtained by fractional crystallisation of salts of the acids with optically active amines, for example (+)- or (−)-alpha-methylbenzylamine, followed by regeneration of the optically pure acid. The optically pure isomeric form of the acid (or its equivalent acid chloride or ester) may then be reacted with the appropriate alcohol to produce a compound of formula (I) in the form of an individually pure isomer thereof. Where one specific isomer is required, there exists the possibility that the residual isomer or isomer mixture may be epimerised and recycled for further isolation of the required form, thereby improving the overall yield of the required isomer.

Where the compounds of Formula (I) are formed as mixtures of diastereoisomers, racemic isomer pairs can be separated by e.g., h.p.l.c. techniques, or, where the physical properties of the compounds are suitable, by selective crystallisation.

The acids, acid halides and esters of formula (II) may themselves be prepared by a number of alternative process. The choice of process depends on the stability of individual substituents under the various reaction conditions employed in the process.

A first process, suitable for the preparation of intermediates of formula (II) wherein Q represents a lower alkoxy group of formula —OR containing up to 6 carbon atoms and $R^1$ represents a primary or secondary alkyl group, provides the compounds of formula II by alkylation of a compound of formula (V)

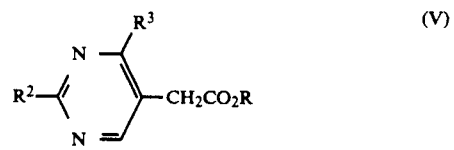

wherein R represents a lower alkyl group containing from 1 to 6 carbon atoms for example using a primary or secondary alkyl halide of formula $R^1$-Hal, wherein Hal represents a halogen atom, in the presence of a base such as lithium hexamethyldisilylazide. The compounds of formula (V) wherein $R^3$ represents a halogen atom may be prepared by reaction of the appropriate amidine or guanidine with a dialkyl ester of 1-formylsuccinic acid, followed by conversion of the 4-hydroxy substituent on the pyrimidine ring to halogen by standard halogenation methods, for example using phosphorus oxychloride or phosphorous oxybromide. The compounds of formula (V) where $R^3$ represents hydrogen or fluorine may be prepared from the corresponding compounds wherein $R^3$ represents chlorine by reduction or reaction with a fluorinating agent, such as potassium fluoride. Examples of these processes are summarised in Schemes I and II

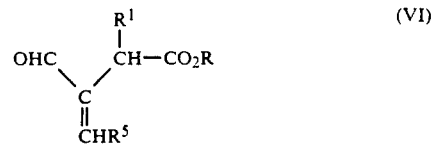

(VI)

SCHEME I

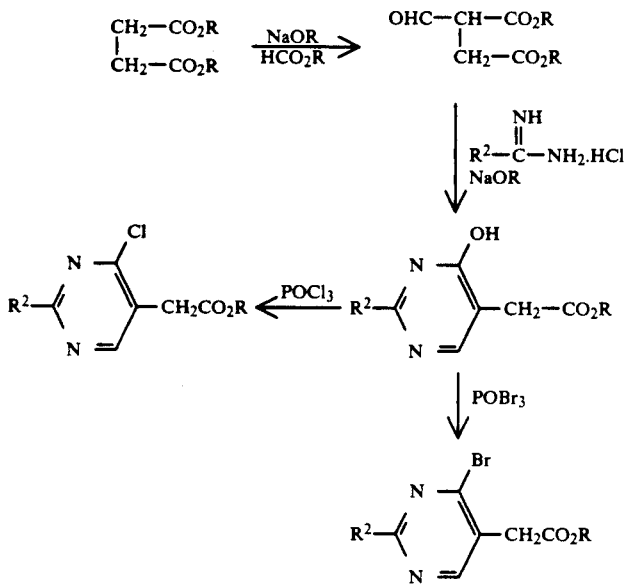

SCHEME II

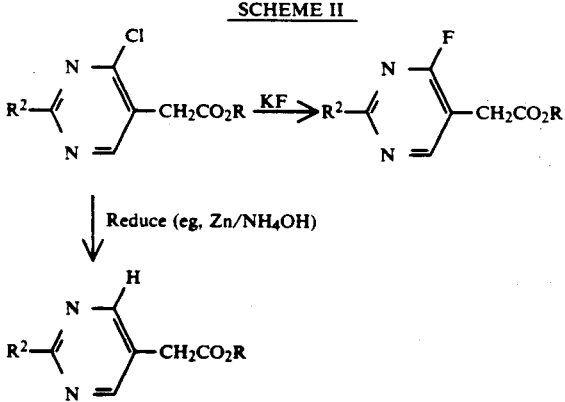

A second process suitable for the preparation of intermediates of formula (II), where Q represents a lower alkoxy group of formula —OR containing up to 6 carbon atoms and $R^3$ represents hydrogen, is of general applicability with reference to the groups $R^1$ and $R^2$. In this process on acetal of formula $(R'O)_2CH$—$CH_2$—$CH(R^1)$—$CO_2R$, (X) wherein R' and R both represent lower alkyl containing up to 6 carbon atoms, is reacted with phosphorus oxychloride and a formamide selected from a dialkyl formamide wherein each alkyl group contains from 1 to 4 carbon atoms (for example dimethylformamide), N-formylpiperidine and N-formylpyrollidine to give either a 4-alkoxy or a 4-dialkylamino substituted 3-formylbut-3-enoic ester of formula (VI) or a mixture thereof, depending on the reaction conditions:

where $R^5$ represents alkoxy containing 1 to 6 carbon atoms, dialkylamino wherein each alkyl group contains 1 to 4 carbon atoms, piperidin-1-yl or pyrollidin-1-yl, and $R^1$ and R are as described hereinbefore. Reaction of the compounds of formula (VI) with a compound of formula $R^2$—$C(NH_2)$=NH, or a salt thereof, wherein $R^2$ has any of the meanings given hereinbefore, optionally in the presence of a base, produces the intermediates of formula (II) wherein $R^3$ is hydrogen and Q represents a lower alkoxy group of formula —OR containing up to 6 carbon atoms. These processes, and a general process for the derivative of the acetals of formula (X) are illustrated by way of example in Scheme III. An alternative process for the preparation of appropriately substituted acetals of formula (X) wherein $R^1$ may have any of the meanings described before other than alkenyl, alkynyl and haloalkenyl is described in Scheme IIIA for the particular case where $R^1$ is t-butyl. This process gives higher yields than that described in Scheme III when $R^1$ represents a tertiary alkyl substituent, for example t-butyl or t-pentyl.

SCHEME III

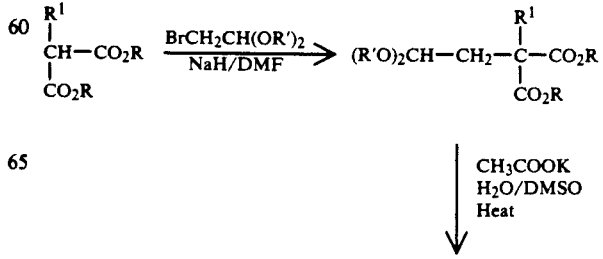

SCHEME IIIA
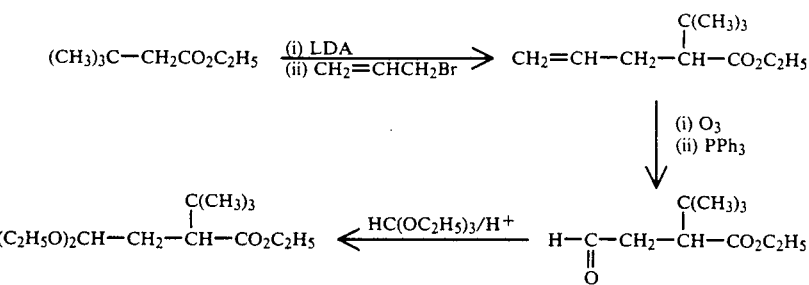
Key: LDA = Lithium di-isopropylamide
Two further processes for preparing alkyl esters and acids of formula II where $R^3$ is hydrogen and $R^2$ is a tertiary alkyl group are illustrated by way of example only in Scheme IV and V, for the case where both $R^1$ and $R^2$ represent t-butyl.
SCHEME IV
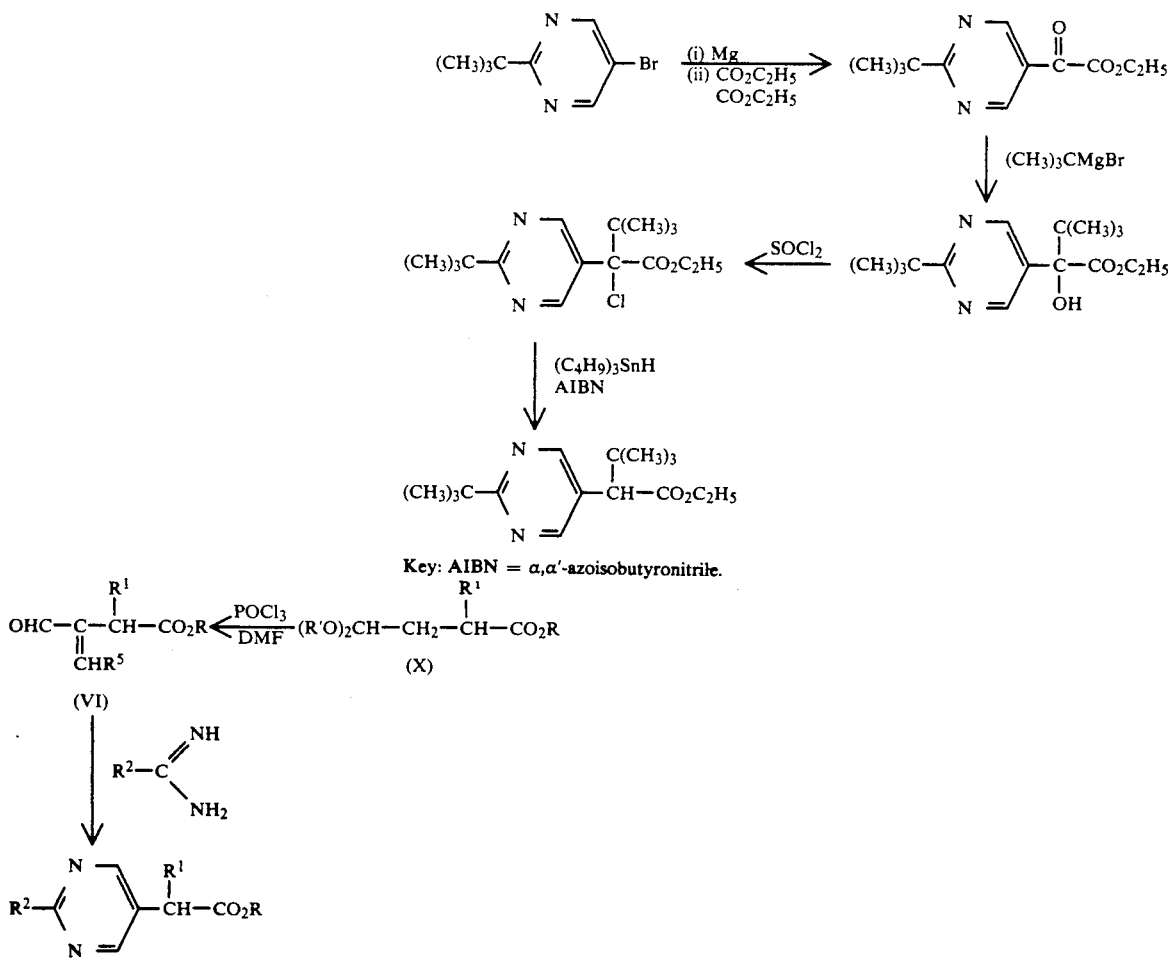
Key: AIBN = α,α'-azoisobutyronitrile.
SCHEME V
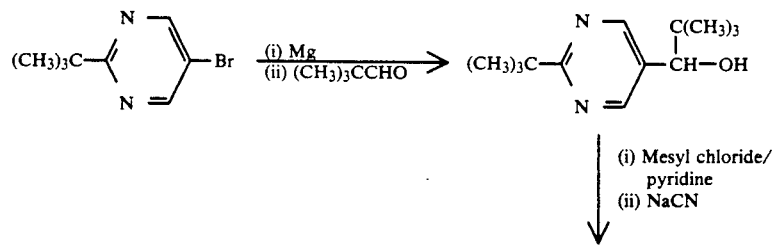

SCHEME V

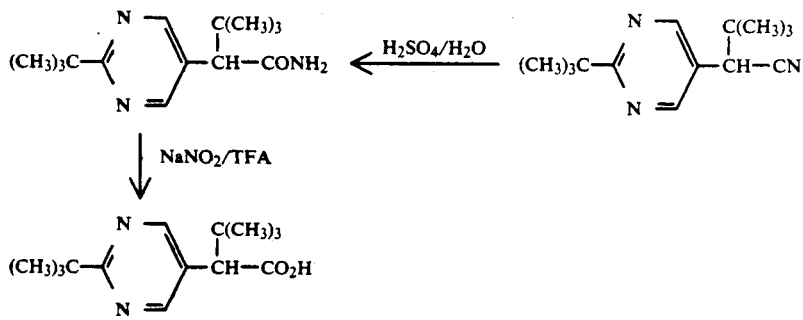

Key: Mesyl chloride = CH$_3$SO$_2$Cl
TFA = Trifluoroacetic acid

The intermediates of formula (II) where Q represents a lower alkoxy group of formula OR, R$^3$ represents hydrogen and R$^1$ represents a haloalkyl group may not be readily accessible by the processes described hereinbefore owing to competing reactions at the haloalkyl group under certain of the reaction conditions employed. A process by which these compounds may be obtained is illustrated in Scheme VI, by way of example, for the case where R$^1$ is trifluoromethyl.

SCHEME VI

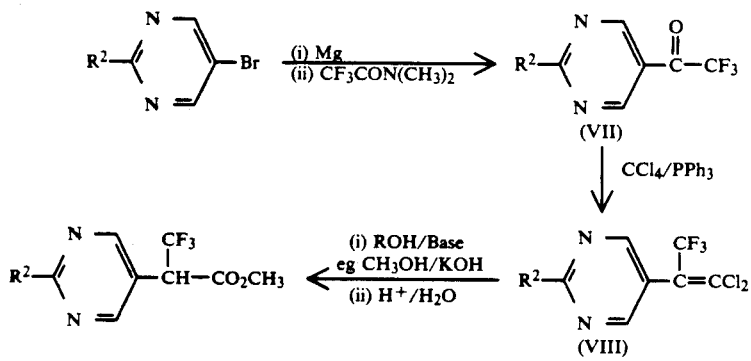

Key: ROH represents a lower alkanol containing from 1 to 4 carbon atoms

The choice of synthetic route used for the preparation of the intermediates of formula (II) wherein Q represents alkoxy or hydroxy will depend on the particular values of R$^1$, R$^2$ and R$^3$ in the desired product.

The processes illustrated in Schemes I and VI provide a range of methods for which a choice may be made by one with normal skill in the art having regard to the nature and reactivity of the substituents concerned. In some specific cases, variation of the conditions or reagents, or selection of a specifically appropriate synthetic route may be required to suit particular circumstances.

One such case is illustrated in Scheme VII, wherein R$^1$ represents 1,1-dimethylprop-2-en-1-yl, a sterically hindered alkenyl group unsuitable for introduction by the methods described hereinbefore. A second case is illustrated in Scheme VIII for the preparation of compounds of formula (I) wherein R$^1$ represents prop-1-en-2-yl.

SCHEME VII

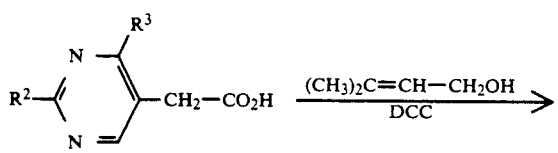

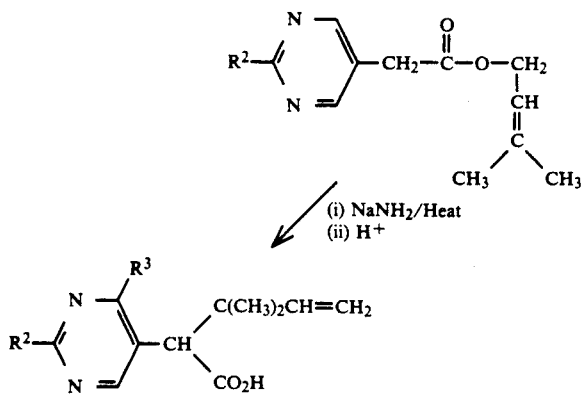

Key: DCC = dicyclohexyl carbodiimide

SCHEME VIII

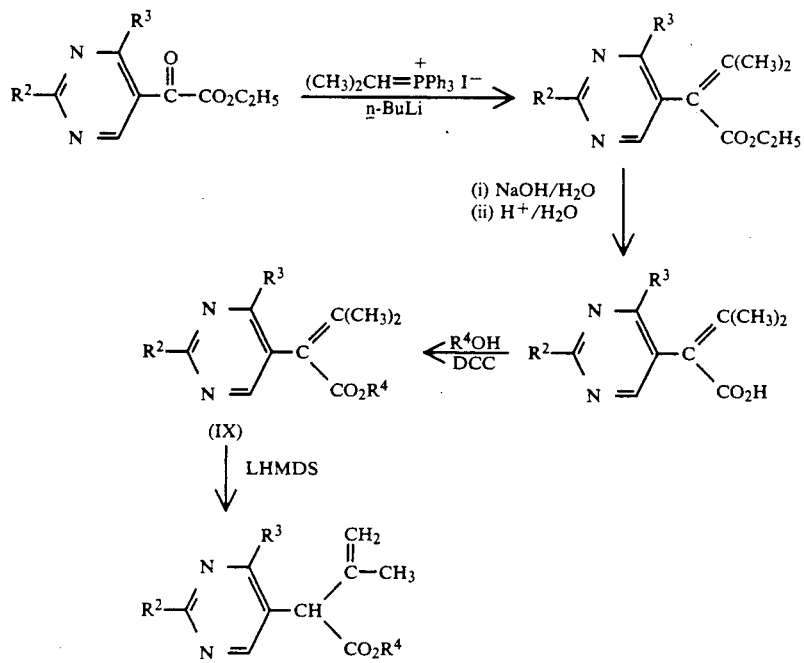

Key: n-BuLi = n-butyllithium
  DCC = dicyclohexylcarbodiimide
  LHMDS = Lithium hexamethyldisilazide Further details of the processes described above may be found in the Examples hereinafter.

Many of the intermediates used in the processes described hereinabove are believed to be novel. Accordingly in further aspects, the invention provides a compound of formula (II):

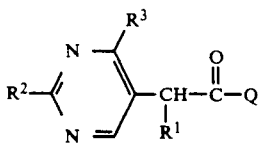
(II)

wherein $R^1$, $R^2$ and $R^3$ have any of the meanings given above and Q represents hydroxy, lower alkoxy containing from 1 to 6 carbon atoms or halogen; a compound of formula (VI):

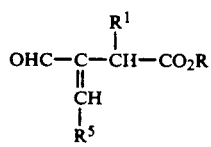
(VI)

where $R^1$ has any of the meanings given above, R represents lower alkyl containing from 1 to 6 carbon atoms, and $R^5$ represents alkoxy containing 1 to 6 carbon atoms, dialkylamino wherein each alkyl group contains 1 to 4 carbon atoms, piperidin-1-yl or pyrrolidin-1-yl; a compound of formula (VII):

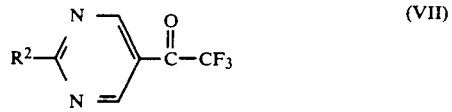
(VII)

wherein $R^2$ has any of the meanings given hereinbefore; a compound of formula (VIII)

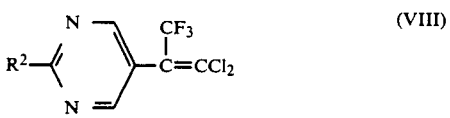
(VIII)

wherein $R^2$ has any of the meanings given herein before; and a compound of formula (IX)

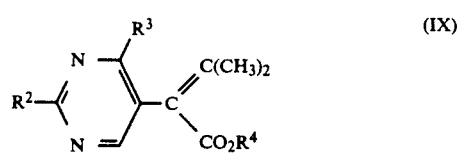
(IX)

wherein $R^2$, $R^3$, and $R^4$ have any of the meanings given hereinbefore. The compounds of formula (IX) have also been shown to exhibit insecticidal and acaricidal activity.

The compounds of formula (I) may be used to combat and control infestations of insect and acarine pests. The insect and acarine pests which may be combated and controlled by the use of the invention compounds include those pests associated with agriculture (which term includes the growing of crops for food and fibre products, horticulture and animal husbandry), forestry, the storage of products of vegetable origin, such as fruit, grain and timber, and also those pests associated with the transmission of diseases of man and animals.

In order to apply the compounds to the locus of the pests they are usually formulated into compositions which include in addition to the insecticidally active ingredient or ingredients of formula (I) suitable inert diluent or carrier materials, and/or surface active agents.

The compounds of the invention may be the sole active ingredient of the composition or they may be admixed with one or more additional active ingredients such as insecticides, insecticide synergist, herbicides, fungicides or plant growth regulators where appropriate.

Suitable additional active ingredients for inclusion in admixture with the compounds of the invention may be compounds which will broaden the spectrum of activity of the compounds of the invention or increase their persistence in the location of the pest. They may synergise the activity of the compounds of the invention or complement the activity for example by increasing the speed of effect, improving knockdown or overcoming repellency. Additionally multi-component mixtures of this type may help to overcome or prevent the development of resistance to individual components.

The particular insecticide, herbicide or fungicide included in the mixture will depend upon its intended utility and the type of complementary action required. Examples of suitable insecticides include the following:

(a) Pyrethroids such as permethrin, esfenvalerate, deltamethrin, cyhalothrin, biphenthrin, fenpropathrin, cyfluthrin, tefluthrin, fish safe pyrethroids for example ethofenprox, natural pyrethrins, tetramethrin, s-bioallethrin, fenfluthrin, prallethrin and 5-benzyl-3-furylmethyl-(E)-(1R,3S)-2,2-dimethyl-3-(2-oxothiolan-3-ylidenemethyl)cyclopropane carboxylate;

(b) Organophosphates such as profenfos, sulprofos, dichlorvos, methyl parathion, azinphos-methyl, demeton-s-methyl, heptenophos, thiometon, fenamiphos, monocrotophos, profenophos, triazophos, methamidophos, dimethoate, phosphamidon, malathion, chlorpyifos, phosalone, fensulfothion, fonofos, phorate, phoxim, pyrimiphos-methyl, fenitrothion and diazinon;

(c) Carbamates (including aryl carbamates) such as pirimicarb, cloethocarb, carbofuran, ethiofencarb, aldicarb, thiofurox, carbosulfan, bendiocarb, fenobucarb, propoxur and oxamyl;

(d) Benzoyl ureas such as triflumuron, chlorofluazuron;

(e) Organic tin compounds such as cyhexatin, fenbutatin oxide, azocyclotin;

(f) Macrolides such as avermectins or milbemycins, for example such as abamectin, avermectin, and milbemycin;

(g) Hormones and synthetic mimics thereof such as juvenile hormone, juvabione, ecdysones, methoprene and hydroprene.

(h) Pheromones.

(i) Organochlorine compounds such as benzene hexachoride, DDT, chlordane and dieldrin.

In addition to the major chemical classes of insecticide listed above, other insecticides having particular targets may be employed in the mixture if appropriate for the intended utility of the mixture. For instance selective insecticides for particular crops, for example stemborer specific insecticides for use in rice such as cartap or buprofezin, can be employed. Alternatively insecticides or acaricides specific for particular insect species/stages for example ovolarvicides such as clofentezine, amitraz, chlordimeform, flubenzimine, hexythiazox and tetradifon, motilicides such as dicofol or propargite, adulticides such as bromopropylate, chlorobenzilate, or insect growth regulators such as hydramethylon, cyromazine, methoprene, chlorofluazuron and diflubenzuron may also be included in the compositions.

Examples of suitable insecticide synergists for use in the compositions include piperonyl butoxide, sesamex, and dodecyl imidazole.

Suitable herbicides, fungicides and plant growth regulators for inclusion in the compositions will depend upon the intended target and the effect required. An example of a rice selective herbicide which can be included is propanil, an example of a plant growth regulator for use in cotton is "Pix", and examples of fungicides for use in rice include blasticides such as blasticidin-S. The choice of other ingredients to be used in mixture with the active ingredient will often be within the normal skill of the formulator, and will be made from known alternatives depending upon the total effect to be achieved.

The ratio of the compound of the invention to any other active ingredient in the composition will depend upon a number of factors including the type of insect pests to be controlled, and the effects required from the mixture. However in general, the additional active ingredient of the composition will be applied at about the rate it would usually be employed if used on its own, or at a lower rate if synergism occurs.

The composition may be in the form of dusting powders wherein the active ingredient is mixed with a solid diluent or carrier, for example kaolin, bentonite, kieselguhr, or talc, or they may be in the form of granules, wherein the active ingredient is absorbed in a porous granular material, for example pumice.

Alternatively the compositions may be in the form of liquid preparations to be used as dips, sprays or aerosols. Dips and sprays are generally aqueous dispersions or emulsions of the active ingredient in the presence of one or more known wetting agents, dispersing agents or emulsifying agents (surface active agents). Aerosol compositions may contain the active ingredient or ingredients, a propellant and an inert diluent, for example odourless kerosene or alkylated benzenes. In a preferred form, aerosol compositions may contain from 0.005% to 4% of active ingredient or ingredients, the remainder of the composition comprising a solvent, selected from odourless kerosine and alkylated benzenes, and a propellant. Aerosol compositions may optionally incorporate other additives, for example perfumes or corrosion inhibitors.

Wetting agents, dispersing agents and emulsifying agents may be of the cationic, anionic or non-ionic type. Suitable agents of the cationic type include, for example, quaternary ammonium compounds, for example cetyltrimethyl ammonium bromide. Suitable agents of the anionic type include, for example, soaps, salts of aliphatic monoesters or sulphuric acid, for example sodium lauryl sulphate, salts of sulphonated aromatic compounds, for example sodium dodecylbenzenesulphonate, sodium, calcium or ammonium lignosulphonate, or butylnaphthalene sulphonate, and a mixture of the sodium salts of diisopropyl- and triisopropylnaphthalene sulphonates. Suitable agents of the non-ionic type include, for example, the condensation products of ethylene oxide with fatty alcohols such as oleyl alcohol or cetyl alcohol, or with alkyl phenols such as octyl phenol, nonyl phenol and octyl cresol. Other non-ionic agents are the partial esters derived from long chain fatty acids and hexitol anhydrides, the condensation products of the said partial esters with ethylene oxide, and the lecithins.

The compositions may be prepared by dissolving the active ingredient in a suitable solvent, for example, a ketonic solvent such as diacetone alcohol, or an aromatic solvent such as trimethylbenzene and optionally adding the mixture so obtained to water which may contain one or more known wetting, dispersing or emulsifying agents.

Other suitable organic solvents are dimethyl formamide, ethylene dichloride, isopropyl alcohol, propylene glycol and other glycols, diacetone alcohol, toluene, kerosene, white oil, methylnaphthalene, xylenes and trichloroethylene, N-methyl-2-pyrrolidone and tetrahydrofurfuryl alcohol (THFA).

The compositions which are to be used in the form of aqueous dispersions or emulsions are generally supplied in the form of a concentrate containing a high proportion of the active ingredient or ingredients, the said concentrate to be diluted with water before use. These concentrates are often required to withstand storage for prolonged periods and after such storage, to be capable of dilution with water to form aqueous preparations which remain homogeneous for a sufficient time to enable them to be applied by conventional spray equipment. The concentrates may contain 1–99% by weight of the active ingredient or ingredients. When diluted to form aqueous preparations such preparations may contain varying amounts of the active ingredient depending upon the purpose for which they are to be used. For agricultural or horticultural purposes, an aqueous preparation containing between 0.0001% and 0.1% by weight of the active ingredient is particularly useful.

In use the compositions are applied to the pests, to the locus of the pests, to the habitat of the pests, or to growing plants liable to infestation by the pests, by any of the known means of applying pesticidal compositions, for example, by dusting or spraying.

The compounds of formula (I) and compositions comprising them are very toxic to wide varieties of insect, acarine and other invertebrate pests, including, for example, the following:
*Myzus persicae* (aphids)
*Aphis gossypii* (aphids)
*Aphis fabae* (aphids)
*Megoura viceae* (aphids)
*Aedes aegypti* (mosquitos)
Anopheles spp. (mosquitos)
Culex spp. (mosquitos)
*Dysdercus fasciatus* (capsids)
*Musca domestica* (houseflies)
*Pieris brassicae* (white butterfly, larvae)
*Plutella maculipennis* (diamond back moth, larvae)
*Phaedon cochleariae* (mustard beetle)
Aonidiella spp. (scale insects)
Trialeuroides spp. (white flies)
*Bemisia tabaci* (white flies)
*Blattella germanica* (cockroaches)
*Periplaneta americana* (cockroaches)
*Blatta orientalis* (cockroaches)
*Spodoptera littoralis* (cotton leaf worm)
*Heliothis virescens* (tobacco budworms)
*Chortiocetes terminifera* (locusts)
Diabrotica spp. (rootworms)
Agrotis spp. (cutworms)
*Chilo partellus* (maize stem borers)
*Nilaparvata lugens* (plant hoppers)
*Nephotettix cincticeps* (leaf hoppers)
*Panonychus ulmi* (European red mite)
*Panonychus citri* (citrus red mite)
*Tetranychus urticae* (two-spotted spider mite)
*Tetranychus cinnabarinus* (carmine spider mite)
*Phyllocoptruta oleivora* (citrus rust mite)
*Polyphagotarsonemus latus* (broad mite)
Brevipalpus spp. (mites)

Many of the compounds of formula (I) have shown especially high levels of activity towards tetranychid mites, such as Tetrancyhus species (for Example *Tetranychus urticae*) and Panonychus species (for Example *Panonychus ulmi*), in a variety of laboratory test systems. In particular, the compounds show high levels of activity against the egg stage as well as all older life stages of such mites. This strong acaricidal action has also been observed in field trials.

All of the compounds which have been tested have shown no cross-resistance to lambda-cyhalothrin or bifenthrin in a strain of *Panonychus ulmi* tolerant to lambda-cyhalothrin and bifenthrin.

The compounds of formula (I) may also be useful in combating insect and acarine pests which infest domestic animals, such as *Lucilia sericata*, and ixodid ticks such as Boophilus spp., Ixodes spp., Amblyomma spp., Rhipicephalus spp. and Dermocentor spp. They are effective in combating both susceptible and resistant strains of these pests in their adult, larval and intermediate stages of growth, and may be applied to the infested host animal by topical, oral or parenteral administration.

The following Examples illustrate various aspects of this invention. In the preparation Examples the products were usually identified and characterised by means of nuclear magnetic resonance spectroscopy and infra red spectroscopy. In each case where a product is specifically named its spectral characteristics are consistent with the assigned structure. Except where stated otherwise, exemplified compounds having one or more asymmetrically substituted carbon atoms were prepared in racemic form.

In the Examples, Gas Liquid Chromatography (GLC) retention times were determined on a Hewlett Packard 5890 Gas Chromatograph, using a Chromopak, C.P. Sil 5 C.B column of 12.5 m length and 0.2 mm internal diameter. Unless otherwise staged, the injection temperature was 100° C., and a temperature gradient of 15° C./minute employed, up to a maximum temperature of 280° C., maintained for 4 minutes. The carrier gas was helium at a column head pressure maintained at 11 pis. Alternative injection and maximum temperature are indicated in the Examples where appropriate.

$^1$H Nuclear Magnetic Resonance (NMR) spectrometry was performed at a frequency of 270 MHz on a Jeol FX 270 NMR spectrometer, unless otherwise indicated. 90 MHz, 60 MHz, 250 MHz and 400 MHz $^1$H NMR spectrometry were performed using Jeol FX 90Q, Brucker WH90, Jeol PMX 60 SI, Brucker WM250, and Jeol GX 400 spectrometers. $^{19}$F NMR spectrometry was performed on a Jeol FX90Q spectrometer at a frequency of 84.26 MHz. All NMR shift values ($\delta$) are quoted in ppm relative to a standard (TMS or CFCl$_3$). In the NMR data, the following abbreviations are used:

s=singlet, d=doublet, t=triplet, q=quartet, dd=double doublet, m=multiplet, b=broad.

Molecular Ion (M+) peaks were determined on one of three mass spectrometers: Jeol DX 303, Kratos MS80 or Hewlett Packard HP 5992.

EXAMPLE 1

The Example illustrates the preparation 2,2-dimethylpropionamidine hydrochloride.

Dry hydrogen chloride gas (ca 59 g) was passed through a solution of 2-cyano-2-methylpropane (86 g) in ethanol (60 cm$^3$) at 0° C. The solution was kept for 60 hours at the ambient temperature (ca. 20° C.), then diluted with diethyl ether (1000 cm$^3$) and the precipitated 1-ethoxy-1-imino-2,2-dimethylpropane hydrochloride collected by filtration, washed on the filter with diethyl ether and dried. This precipitate was then slurried with ethanol (150 cm$^3$) and gaseous ammonia passed into the mixture at the ambient temperature until the solid was completely dissolved.

The mixture was kept at the ambient temperature for 40 hours, diluted with diethyl ether (500 cm$^3$) and the solid precipitate collected by filtration and dried to yield 2,2-dimethylpropionamidine hydrochloride (25.75 g), melting point 192°-194° C. A second crop (50.29 g) was obtained by evaporation of the filtrate.

Infra red (paraffin mull): 3300, 3100, 1680, 1520 1230, 995, 980 cm$^{-1}$

EXAMPLE 2

By a procedure similar to that described in Example 1, the following compounds were prepared from the appropriate starting nitriles. In each case below, the incubation time with hydrogen chloride (to produce the intermediate iminoether) and subsequent incubation time with ammonia (to produce the amidine) are noted where they differ from those recorded in Example 1.

(i) 2-Methylpropionamidine hydrochloride from 2-methylpropionitrile

Hydrogen chloride reaction time: 18 hours (initial warming to 30° C. required to initiate reaction)
Ammonia reaction time: 48 hours.
Infra red (paraffin mull): 3300, 3100, 1680, 1520 cm$^{-1}$ (ii) Cyclopropanecarboxyamidine hydrochoride from cyclopropanecarbonitrile.

Hydrogen chloride reaction time: 6 days
Ammonia reaction time: 16 hours.
Melting point: 55°-58° C.
$^1$H NMR (CDCl$_3$): 0.85 (m); 1.2 (m); 1.7 (m)
Infra red (paraffin mull): 3400, 3200, 1650, 1460, 1380, 1310, 1150, 1040, 940 cm$^1$ (iii) 2,2-Dimethylbutyramidine hydrochloride from 2,2-dimethylbutyronitrile.

Melting point 128°-129° C.
Infra red (paraffin mull): 3350-2630, 1670, 1510, 1460, 1380, 1300, 1210, 1085 cm$^{-1}$ (iv) 1-Methylcyclopropanecarboxamidine hydrochloride from 1-methylcyclopropanecarbonitrile.
Hydrogen chloride reaction time: 1 hour
Ammonia reaction time: 48 hours
$^1$H NMR (CDCl$_3$): 0.84 (m,2H); 1.16 (m,2H); 1.26 (s,3H); 8.40-9.00 (broad, 3H)
Infra Red (paraffin mull): 3200 (broad), 1670, 1530, 1085, 960, 890 cm$^{-1}$ (v) 1-methylcyclohexylcarboxamidine hydrochloride from 1-methylcyclohexylcarbonitrile (prepared according to the method of Example 47)

270 MH$_2$ $^1$H NMR (d$^6$DMSO): 1.10 (3H,s); 1.15-1.50 (8H,m); 1.85 (2H,m); 2.45 (2H,broad s); 8.35 (1H, broad s).

The following amidines were prepared according to literature procedures.

(vi) 2,2,2-trifluoroethylamidine was prepared according to the procedure of W. L. Reilly and H. C. Brown J.A.C.S. 6032–34 1956.

(vii) 2-chlorobenzylamidine was prepared according to the procedure of E. R. Biehl et al J.O.C. 44 (21), 3674, 1979.

EXAMPLE 3

This Example illustrates the stages in the preparation of ethyl (RS)-2-[2-(1,1-dimethylethyl)pyrimidin-5-yl]butanoate.

(i) diethyl (RS)-formylsuccinate

Ethanol (20 cm$^3$) was added portionwise to a suspension of finely divided sodium (10.0 g) in dry toluene (100 cm$^3$). On completion of the addition the mixture was heated for 3.5 hours at 80° C. To the resulting yellow suspension, cooled to 20° C., was added dropwise, over a period of 1 hour, a mixture of diethyl succinate (70.0 g) and ethyl formate (35.0 g), whilst the temperature of the mixture was maintained in the range 20° to 30° C. The mixture was kept at the ambient temperature for 16 hours after which water (100 cm$^3$) was added carefully.

The aqueous layer was separated, neutralised with 50% aqueous sulphuric acid, and extracted with diethyl ether.

The ethereal extracts were washed with water, dried over anhydrous magnesium sulphate, and concentrated by evaporation of the solvent under reduced pressure. The residual liquid (66 g) was subjected to fractional distillation under reduced pressure to obtain the desired diethyl (RS)-formylsuccinate (46.0 g), boiling range 82° to 86° C./0.53 mmHg.

NMR spectroscopy indicated that the product exists as an approximately 1:1 mixture of keto and enol forms.
$^1$H NMR (CDCl$_3$): 1.10-1.40 (m, 3H); 2.90 (d, J=7 Hz, 1H); 3.05 (s,1H); 3.75 (t, J=7 Hz, 0.5H); 4.00-4.40 (m,4H); 7.10 (d,J=11 Hz, 0.5H); 9.92 (s, 0.5H); 11.5 (d, J=11 Hz, 0.5H).
Infra red (liquid film): 3300, 2980, 1735, 1665, 1175, 1030 cm$^{-1}$ (ii) ethyl 2-[2-(1,1-dimethylethyl)-4-hydroxypyrimidin-5-yl]acetate.

A solution of sodium ethoxide obtained by dissolving sodium (6.9 g) in ethanol (120 cm$^3$) was added portionwise to a stirred suspension of 2,2-dimethylpropionamidine hydrochloride (41.0 g) in ethanol (150 cm$^3$). The precipitated sodium chloride was removed by filtration. Diethyl (RS)-formylsuccinate (60 g) was added dropwise to the stirred filtrate at the ambient temperature. After keeping the mixture for 16 hours it was heated to the reflux temperature for 1 hour, after which the solvent was removed by evaporation under reduced pressure to give a solid residue which was washed with petroleum ether (boiling range 60°-80° C.) to yield ethyl 2-[2-(1,1-dimethylethyl)-4-hydroxypyrimidin-5-yl]acetate (40 g), melting point 98°-102° C. A further quantity (15 g) was recovered from the petroleum ether washings by evaporation of the solvent and column chromatographic purification of the residue using a silica column and eluting with a mixture (1:1 by volume) of ethyl acetate and petroleum ether (boiling range 60°-80° C.).

$^1$H NMR (CDCl$_3$): 1.27 (t, J=7 Hz, 3H); 1.39 (s,9H); 3.44 (s, 2H); 4.13 (q, J=7 Hz, 2H); 7.92 (s, 1H); 12.5 (bs, 1H).

Infra red (liquid paraffin): 3400, 1735, 1660, 1570, 1460, 11375, 1335, 1275, 1155, 1030, 980 cm$^{-1}$.

(iii) ethyl 2-[2-(1,1-dimethylethyl)-4-chloropyrimidin-5-yl]acetate

Phosphorus oxychloride (30 cm$^3$) was added portionwise to ethyl 2-[2-(1,1-dimethylethyl)-4-hydroxypyrimidin-5-yl]-acetate (15.0 g). An exothermic reaction occurred and the resultant mixture was poured onto ice. After neutralisation with sodium carbonate the mixture was extracted with ethyl acetate and the extracts washed with water and dried over anhydrous magnesium sulphate. Removal of the solvent by evaporation under reduced pressure yielded ethyl 2-[2-(1,1-dimethylethyl)-4-chloropyrimidin-5-yl]acetate (11.35 g, oil, solidified on standing, mp. 42°-44° C.).

$^1$H NMR (CDCl$_3$): 1.29 (t, J=7 Hz, 3H); 1.40 (s, 9H); 3.71 (s, 2H); 4.20 (q, J=7 Hz, 2H); 8.51 (s, 1H)

Infra red (liquid film): 2960, 1735, 1580, 1520, 1420, 1250, 1180, 1025, 880 cm$^{-1}$ (iv) ethyl 2-[2-(1,1-dimethylethyl)pyrimidin-5-yl]acetate.

A mixture of ethyl 2-[2-(1,1-dimethylethyl)-4-chloropyrimidin-5-yl]acetate (18 g), toluene (180 cm$^3$), zinc dust (36 g) and 3 molar ammonium hydroxide solution saturated with sodium chloride (180 cm$^3$) was heated at 100° C. for 120 hours. After cooling and filtering to remove the solid component the organic phase was separated, the aqueous phase washed with ethyl acetate and the washings combined with the organic phase. After washing the organic phase with water and drying over anhydrous magnesium sulphate the solvents were removed by evaporation under reduced pressure and the residual oil (16 g) was subjected to purification by column chromatography using a silica column eluted with dichloromethane to yield ethyl 2-[2-(1,1-dimethylethyl)pyrimidin-5-yl]acetate (12 g) as a yellow oil.

$^1$H NMR (CDCl$_3$): 1.25 (t, J=7 Hz, 3H); 1.40 (s, 9H); 3.55 (s, 2H); 4.2 (q, J=7 Hz, 2H); 8.6 (s, 2H)

Infra red (liquid film): 2960, 1735, 1480, 1430, 1260. 1180, 1025 cm$^{-1}$

An alternative reduction procedure is described below: (reference J. Org. Chem (1985), 50, 3408-11).

Ethyl 2-[2-(1,1-dimethylethyl)-4-chloro-pyrimidin-5-yl]acetate (0.016 g) was dissolved in tetrahydrofuran (25 cm$^3$) containing potassium carbonate (0.809 g) and 5% palladium on carbon (0.188 g, catalyst). To the stirred mixture at the ambient temperature was added in portions sodium hypophosphite (0.995 g) in water (7.3 cm$^3$) over 5 hours.

The reaction mixture was stood overnight, filtered to remove the catalyst and the filtrate, and extracted with ethyl acetate. The organic layer was washed with water, dried (magnesium sulphate) and evaporated under reduced pressure to yield the reduced product as an oil (0.635 g), shown by spectroscopic analysis to be identical with that obtained by the process described above.

GLC Retention time: 3.76 minutes.
Molecular ion: 222

(v) ethyl (RS)-2-[2-(1,1-dimethylethyl)pyrimidin-5-yl]butanoate.

Lithium bis-(trimethylsily)amide (2.5 cm$^3$ of a 1 molar solution in dry tetrahydrofuran) was added dropwise to a solution of ethyl 2-[2-(1,1-dimethylethyl)pyrimidin-5-yl]acetate (0.5 g) in dry tetrahydrofuran (10 cm$^3$) maintained at −78° C., and the resultant solution stirred for 30 minutes at −78° C. Ethyl iodide (1.05 g) was then added dropwise, and after stirring the resultant mixture for 1 hour while maintaining the temperature at −78° C., the reaction mixture was allowed to warm to the ambient temperature. After a further fourteen hours, the reaction mixture was poured into aqueous ammonium chloride solution, and extracted with ethyl acetate. The combined organic extracts were washed with water, dried over anhydrous magnesium sulphate and concentrated by evaporation of the solvent under reduced pressure.

The resultant orange oil was purified by column chromatography on silica gel using dichloromethane as eluent to give ethyl (RS)-2-[2-(1,1-dimethylethyl)-pyrimidin-5-yl]-butanoate.

$^1$H NMR (CDCl$_3$): 0.95 (3H,t); 1.20 (3H,t); 1.4 (9H,s); 1.8-2.20 (2H,m); 3.40 (1H,t); 4.20 (2H,q); 8.60 (s,2H)

GLC Retention Time: 4.37 minutes.

EXAMPLE 4

Ethyl 2-[2-(1,1-dimethylethyl)pyrimidin-5-yl]pent-4-enoate was prepared according to the procedure described in Example 3(v), using allyl bromide in place of ethyl iodide.

$^1$H NMR (CDCl$_3$): 1.10 (t,3H); 1.25 (s,9H); 2.40 (m,1H); 2.70 (m,1H); 3.45 (t,1H); 4.00 (m,2H); 4.95 (m,2H); 5.55 (m,1H); 8.50 (s,2H);

IR (Liquid film): 2960, 1735, 1588, 1547, 1482, 1433, 1366, 1182, 1031, 921, 820 cm$^{-1}$ GLC Retention time: 4.76 minutes.

EXAMPLE 5

This example illustrates the steps involved in the preparation of ethyl (RS)-4-dimethylamino-3-formyl-2-(1-methylethyl)-3-butenoate, ethyl (RS)-4-ethoxy-3-formyl-2-(1-methylethyl)-3-butenoate and mixtures thereof.

(i) Preparation of diethyl 2-(1-methylethyl)-2-(2,2-diethoxyethyl)-malonate. (Reference Bull. Soc. Chim. France, 1965, p 1761).

Sodium hydride (4.8 g of a 50% dispersion in oil) was washed free of oil with petroleum ether of boiling range 40°-60° C., and suspended in dry dimethylformamide; the suspension was cooled to 0° C. by external cooling. A solution of diethyl 2-(1-methylethyl)malonate (21.2 g) in dry dimethylformamide (25 cm$^3$) was added in portions to the suspension and the reaction mixture was stirred at 10° C. for 15 minutes, whereafter no further evolution of hydrogen could be detected. A solution of bromoacetaldeyde diethylacetal (19.7 g - commercially available from Aldrich Chemical Company Limited, Gillingham, England) in dimethylformamide (25 cm$^3$) was added to the reaction mixture to give a red-brown solution, which was then heated at 120°-130° C. for 20 hours with stirring. After cooling the reaction mixture to 0° C., an ice/water mixture (total volume 1000 cm$^3$) was added cautiously. The product was extracted with diethyl ether (3×250 cm$^3$) and the combined organic layers washed with water (2×300 cm$^3$), dried over anhydrous magnesium sulphate and concentrated by evaporation of the solvent under reduced pressure. The residual liquid was subjected to fractional distillation through a short Vigreux column to give diethyl 2-(1-methylethyl)-2-(2,2-diethoxyethyl)malonate (10.5 g), boiling point 94°-98° C./0.1 mmHg.

¹H NMR (CDCl₃): 1.0 (d, 6H); 1.2 (t, 6H); 1.3 (t, 6H); 2.25 (d, 2H); 2.3 (m, 1H); 3.4-3.75 (m, 4H); 4.2 (m, 4H); 4.65 (m, 1H).

Infra red (liquid film): 2990, 1730, 1230, 1120, 1070 cm⁻¹

(ii) Preparation of ethyl (RS)-4,4-diethoxy-2-(1-methylethyl)butanoate

Diethyl 2-(1-methylethyl)-2-(2,2-diethoxyethyl)-malonate (60 g) was added to dimethyl sulphoxide (450 cm³) containing potassium acetate (37 g) and water (6.8 cm³). The mixture was stirred under nitrogen and heated to 130°-140° C. for 18 hours. Analysis by gas liquid chromatography indicated that the reaction was 40% complete. The reaction temperature was increased to 160°170° C. and heating continued for a further 18 hours.

The reaction mixture was cooled to room temperature and diluted with water (3000 cm³). The product was extracted using diethyl ether (3×800 cm³) and the combined organic layers were washed with water (33×800 cm³) and dried over anhydrous magnesium sulphate. The solvent was evaporated under reduced pressure to give a brown liquid. Fractional distillation of the residue gave ethyl (RS)-4,4-diethoxy-2-(1-methylethyl)butanoate (31.8 g) as a pale yellow liquid, boiling point 68°-70° C./0.2 mmHg.

1H NMR (CDCl₃): 0.9 (d, 6H); 1.0 (m, 9H); 1.75 (m, 1H); 1.8-2.05 (m, 2H); 2.15 (m, 1H); 3.4-3.7 (m, 4H); 4.05-4.2 (m, 2H); 4.45 (m, 1H)

Infra red (liquid film): 2990, 1730, 1375, 1180, 1120, 1060 cm⁻¹

This compound may also be prepared by the methods described in Chemical Abstracts, 59, 5012g (1963) and 51 12086c (1957).

(iii) Preparation of ethyl (RS)-4-dimethylamino-3-formyl-2-(1-methylethyl)-3-butenoate, ethyl (RS)-4-ethoxy-3-formyl-2-(1-methylethyl)-3-butenoate and mixtures thereof.

To dry dimethylformamide (4.64 cm³) was added dropwise at 5° C., phosphorous oxychloride (5.50 cm³). This gave initially a viscous solution which then solidified. To this was added 1,2-dichloroethane (10 cm³) and the reaction mixture stirred at 60° C. for 45 minutes to form the Vilsmeyer - Haack reagent.

A solution of ethyl (RS)-4,4-diethoxy-2-(1-methylethyl)butanoate (5 g) in 1,2-dichloroethane (10 cm³) was added dropwise to the reaction mixture, which was then heated for a further 1 hour at 60° C.

The reaction mixture was sampled by adding an aliquot to solid potassium carbonate, diluting with water, and heating for a 5 minutes at 50°-65° C. An extract using ethyl acetate as solvent was analysed by gas liquid chromatography, which indicated 30% completion of reaction.

The reaction mixture was heated for a further 1 hour at 70° C., allowed to cool to the ambient temperature, then reheated for a further 1 hour at 70° C. The reaction mixture was cooled to 0° C. and cautiously added to an excess of solid potassium carbonate. The slurry was cautiously diluted with ice/water and the mixture heated on a steam bath for 10 minutes. The mixture was cooled to room temperature and saturated sodium chloride solution added. The product was extracted with ethyl acetate (2×750 cm³), dried over anhydrous magnesium sulphate and the solvent was evaporated under reduced pressure. The residual brown liquid was placed under vacuum (0.5-1.0 mmHg) and heated to 50° C. to remove volatile impurities.

The product was obtained as a brown liquid (3.4 g) and was used without further purification.

Analysis of the product by gas chromatography/mass spectroscopy showed the product to contain 68% ethyl (RS)-4-dimethylamino-3-formyl-2-(1-methylethyl)-3-butenoate (I), 12% ethyl (RS)-4-ethoxy-3-formyl-2-(1-methylethyl)-3-butenoate (II) and 17.5% 3-(1-methylethyl)-5-hydroxytetrahydrofuran-2-one (III) as an impurity. Ratios of I to II were found to vary according to reaction conditions and isolation procedures, but all mixtures were found to be satisfactory for further conversion to derivatives as described in the remaining examples.

Molecular ion (Product I): 227
Molecular ion (Product II): 228
Molecular ion (Product III): 144

EXAMPLE 6

Ethyl (RS)-4-dimethylamino-3-formyl-2-(1,1-dimethylethyl)-3-butenoate was prepared by the method of Example 5 from diethyl 2-(1,1-dimethylethyl)malonate. The physical data for the intermediates and final product are given below:

(i) Diethyl 2-(1,1-dimethylethyl)-2-(2,2-diethoxyethyl)malonate

¹H NMR (CDCl₃): 1.10 (9H,s); 1.17 (6H,t); 1.3 (6H,t); 2.2 (2H,d); 3.4-3.71 (4H,m); 4.2 (4H,q); 4.75 (1H,t)

Infra Red (liquid film) 2977, 1725, 1446, 1372, 1256, 1198, 1074, 977, 867 cm⁻¹

GLC Retention Time: 5.01 minutes.

(ii) Ethyl (RS)-4,4-diethoxy-2-(1,1-dimethylethyl)-butanoate

¹H NMR (CDCl₃): 0.96 (9H,s); 1.18-1.3 (9H,m); 1.7-1.8 (1H,m); 2.0-2.1 (1H,m); 2.05-2.30 (1H,dd); 3.4-3.8 (4H,m); 4.05-4.2 (2H,m): 4.4 (1H,m).

Infra Red (liquid film) 2975, 1729, 1478, 1372, 1347, 1064 cm⁻¹

GLC Retention Time: 2.90 minutes (iii) Ethyl (RS)-4-dimethylamino-3-formyl-2-(1,1-dimethylethyl)-3-butenoate as a 2:1 mixture of Z and E isomers.

¹H NMR (CDCl₃): 0.94 and 1.04 (9H,2s); 1.23 (3H,t); 3.15 and 3.20 (6H,2s); 3.94-4.2 (3H,m); 6.9-7.5 (1H, broad s); 9.05-9.65 (1H, broad s).

Infra Red (liquid film) 2957, 1720, 1599, 1399, 1365, 1305, 1146, 1044, 878 cm⁻¹

GLC Retention Time: 3.95 minutes.

Molecular ion: 241

Spectroscopic data consistent with 2:1 mixture of Z and E isomers.

Variation of the reaction and isolation conditions may produce ethyl (RS)-4-ethoxy-3-formyl-2-(1,1-dimethyethyl)-3-butenoate in addition to the dimethylamino product.

EXAMPLE 7

The Example illustrates an alternative procedure for the preparation of ethyl (RS)-4,4-diethoxy-2-(1,1-dimethylethyl)butanoate.

(i) Preparation of ethyl (RS)-2-(1,1-dimethylethyl)-pent-4-enoate.

n Butyllithium (44 cm³ of a 2.5 molar solution in Hexane) was added to a solution of dry di-isopropylamine (14.7 cm³) in dry tetrahydrofuran (75 cm³) whilst the temperature was maintained at −40° C.

The reaction mixture was then allowed to warm to 0° C. before being cooled to −70° C. A solution of ethyl 3,3-dimethylbutanoate (14.4 g) in dry tetrahydrofuran (20 cm$^3$) was then added dropwise to the reaction mixture which was maintained at −70° C. After the addition was complete, the reaction temperature was allowed to rise to −60° C. for 15 minutes, before being cooled again to −70° C. A solution of allyl bromide (13.4 g) in dry tetrahydrofuran (5 cm$^3$) was then added in portions to the reaction mixture, which was allowed to warm to the ambient temperature, and stirred for a further 16 hours.

The solvent was removed by evaporation under reduced pressure and the residual liquid was poured into water, and extracted into diethyl ether. The combined organic extracts were washed with water, dilute aqueous hydrochloric acid and water again.

The organic portion was dried over anhydrous magnesium sulphate, and concentrated by evaporation of the solvent under reduced pressure. The residual liquid was subjected to fractional distillation under reduced pressure through a Vigreux column to give ethyl (RS)-2-(1,1-dimethylethyl)pent-4-enoate (14.3 g), boiling point 49°–50° C./0.6 mmHg.

90 MHz $^1$H NMR (CDCl$_3$): 0.95 (9H,s); 1.20 (3H,t); 2.20 (3H,m); 4.10 (2H,q); 4.7–5.8 (3H,m).

Infra Red (Liquid film): 3083, 2966, 1729, 1641, 1477, 1369, 1346, 1151, 1028 and 915 cm$^{-1}$ (ii) Preparation of ethyl (RS)-2-(1,1-dimethylethyl)-4-oxobutanoate.

A stream of ozone in oxygen generated using a Pennwalt type BA 023012 ozonator was passed through a solution of ethyl (RS)-2-(1,1,-dimethylethyl)pent-4-enoate (4.3 g) in dry dichloromethane (100 cm$^3$) while the temperature was maintained at −40° C. When the reaction solution had taken on a pale blue colouration excess ozone was removed by the passage of oxygen through the solution. Triphenyl phosphine (20 g) was added to the cold reaction mixture, which was allowed to warm to the ambient temperature, for a period of three hours.

The solvent was removed by evaporation under reduced pressure, and replaced by petroleum ether (boiling range 40°–60° C., 250 cm$^3$) and the triturated mixture filtered. The residue was washed with a further portion of petroleum ether, and the combined filtrates concentrated by evaporation of the solvent under reduced pressure.

The residue was subjected to short path distillation through a Kugelrohr apparatus to give ethyl (RS)-2-(1,1-dimethylethyl)-4-oxo-butanoate (3.2 g), boiling point 100° C./2 mmHg.

270 MHz $^1$H NMR (CDCl$_3$): 0.98 (9H,s); 1.27 (3H,t); 2.64 (2H,m); 3.00 (1H,m); 4.15 (2H,q); 9.50 (1H,s)

Infra Red (liquid film): 2966, 1726, 1477, 1370, 1216, 1187, 1157, 1096, 1027 and 924 cm$^{-1}$.

GLC Retention Time: 1.53 minutes.

(iii) Ethyl (RS)-4,4-diethoxy-2-(1,1-dimethylethyl)-butanoate.

Ethyl (RS)-2-(1,1-dimethylethyl)-4-oxo-butanoate (0.57 g) was dissolved in excess triethylorthoformate and a catalytic amount of p-toluenesulphonic acid was added. After stirring for 1 hour at the ambient temperature, excess triethylorthoformate was evaporated under reduced pressure to give ethyl (RS)-4,4-diethoxy-2-(1,1-dimethylethyl)butanoate, the spectral data of which were identical to those obtained in Example 6 (ii).

EXAMPLE 8

Ethyl (RS)-4-dimethylamino-3-formyl-2-cyclopropyl-3-butenoate was prepared by the method of Example 5 from diethyl 2-cyclopropylmalonate. (Note: the preparation of 2-cyclopropylmalonate is described by Carney et al, Organic Preparations And Procedures International, Vol 5, P 25–29 (1973). The physical data for the intermediates and final produce are given below:

(i) Diethyl 2-cyclopropyl-2-(2,2-diethoxyethyl)malonate.

Boiling Point: 104°–110° C./0.1 mmHg $^1$H NMR (CDCl$_3$): 0.4, 0.56 (4H,m); 1.18 (6H,t); 1.26 (6H,t); 1.42 (1H,m); 2.24 (2H,d); 3.48, 3.64 (4H,m); 4.16 (4H,m); 4.76 (1H,t).

Infra Red (liquid film) 2979, 1729, 1445, 1372, 1285, 1242, 1062, 862 cm$^{-1}$.

GLC Retention Time: (50° C.–280° C. run): 7.04 minutes.

(ii) Ethyl (RS-4,4-diethoxy-2-cyclopropylbutanoate.

Boiling Point 62°–63° C./0.08 mmHg $^1$H NMR (CDCl$_3$): 0.16, 0.32 (2H,m); 0.50 (2H,m); 0.88 (1H,m); 1.18 (6H,t); 1.26 (3H,t); 1.70, 1.88 (2H,m); 2.12 (1H,m); 3.46, 3.60 (4H,m); 4.15 (2H,m); 4.56 (1H,t).

Infra Red (liquid film): 3081, 2977, 1732, 1444, 1373, 1060, 825 cm$^{-1}$.

GLC Retention Time (50° C.–280° C. run): 4.78 minutes.

(iii) Ethyl (RS)-4-dimethylamino-3-formyl-2-cyclopropyl-3-butenoate.

$^1$H NMR (CDCl$_3$): 0.1, 0.24 (2H,m); 0.42, 0.64 (2H,m); 1.24 (3H,t); 1.42 (1H,m); 3.12 (6H,s); 3.44 (1H,d); 4.18 (2H,q); 6.66 (1H, broad s); 8.88 (1H, broad s).

Infra Red (liquid film) 3080, 2982, 2730, 1726, 1680, 1606, 1488, 1445, 1401, 1303, 1197, 1036, 911, 886, 853, 826, 727 cm$^{-1}$.

GCL Retention Time: (50° C.–280° C. run): 7.61 minutes.

Molecular ion: 225

It is believed that the spectroscopic data are consistent with the E isomer of the product.

EXAMPLE 9

This Example illustrates the preparation of ethyl (RS)-2-[2(1,1-dimethylethyl)pyrimidin-5-yl]-3,3-dimethylbutanoate.

A solution of sodium ethoxide in ethanol was prepared by the addition of sodium (0.276 g) to ethanol (20 cm$^3$) under a nitrogen atmosphere. The solution was cooled to the ambient temperature (ca 20° C.) and 2,2-dimethylpropionamidine hydrochloride (1.64 g) was added. A solution of a 1:1 mixture of ethyl (RS)-4-dimethylamino-3-formyl-2-(1,1-dimethylethyl)-3-butenoate and ethyl (RS)-4-ethoxy-3-formyl-2-(1,1-dimethylethyl)-3-butenoate (2.6 g prepared according to the method of Example 6) in ethanol (25 cm$^3$) was added to the reaction mixture which was then heated at the reflux temperature for 3.5 hours. The mixture was cooled to the ambient temperature and the solvent evaporated under reduced pressure. Water (200 cm$^3$) was added to the residue and the products extracted into diethyl acetate (2×150 cm$^3$). The combined organic layers were dried over anhydrous magnesium sulphate and the solvent evaporated under reduced pressure to leave a brown oil. The crude product was purified by column chromatography on a silica gel support, eluting with dichloromethane containing 2% by volume ethyl acetate to give the title compound (1.5 g) as a pale yellow oil.

¹H NMR (CDCl₃): 1.0 (9H,s); 1.25 (3H,t); 1.42 (9H,s); 3.35 (1H,s); 4.15 (2H,m); 8.75 (2H,s).

Infra Red (liquid film) 2962, 2872, 1732, 1586, 1539, 1482, 1433, 1369, 1333, 1200, 1149, 1036, 939, 854, 821 cm⁻¹

GLC Retention Time: 4.87 minutes.

Molecular ion: 278

EXAMPLE 10

This Example illustrates the preparation of (RS)-2-[2-(1,1-dimethylethyl)pyrimidin-5-yl]-3,3-dimethyl-butanoic acid.

A solution of lithium hydroxide hydrate (0.12 g) in water (5 cm³) was added to a solution of ethyl (RS)-2-[2-(1,1-dimethylethyl)pyrimidin-5-yl]-3,3-dimethyl-butanoate (0.35 g) in propan-2-ol (10 cm³) and the mixture was heated at the reflux temperature for 8 hours. Further lithium hydroxide hydrate (0.13 g) was then added and heating continued for a further 13 hours. The mixture was cooled, and concentrated by evaporation under reduced pressure. The residue was added to aqueous sodium carbonate solution and residual ester extracted into dichloromethane (2×75 cm³). The aqueous layer was acidified with 2 molar aqueous hydrochloric acid solution and the acid product extracted into dichloromethane (2×100 cm³). The organic layers were dried over anhydrous magnesium sulphate and the solvent evaporated under reduced pressure to give the title compounds as a low melting solid (0.22 g). The product was used without further purification.

¹H NMR (CDCl₃): 0.89 (9H,s); 1.29 (9H,s); 3.4 (1H,s); 3.25 (1H,broad s); 8.7 (2H,s).

Infra Red (paraffin mull) Acid OH at 3100-2300 cm⁻¹

GLC Retention Time: 5.5 minutes.

Molecular ion: 250

EXAMPLE 11

The following compounds were prepared from the appropriate starting materials according to the method of Example 9.

(i) Ethyl (RS)-2-[2-(1-methylethyl)pyrimidin-5-yl]-3,3-dimethylbutanoate.

90 MHz ¹H NMR (CDCl₃): 1.25 (3H,2t); 1.35 (6H,d); 3.20 (1H,m); 3.35 (1H,s); 4.15 (2H,2d); 8.7 (2H,s).

(ii) Ethyl (RS)-2-[2-(N,N-dimethylamino)pyrimidin-5-yl]-3,3-dimethylbutanoate.

90 MHz ¹H NMR (CDCl₃): 1.0 (9H,s); 1.25 (3H,2t); 3.15 (6H,s); 4.10 (2H,2q); 8.30 (2H,s).

(iii) Ethyl (RS)-2-(2-cyclopropylpyrimidin-5-yl)-3,3-dimethylbutanoate.

90 MHz ¹H NMR (CDCl₃): 1.0 (9H,s); 1.15 (4H,m); 1.25 (3H,2t); 2.25 (1H,m); 3.30 (1H,s); 4.12 (2H,2q); 8.55 (2H,s).

(iv) Ethyl (RS)-2-(2-phenylpyrimidin-5-yl)-3,3-dimethylbutanoate.

90 MHz ¹H NMR (CDCl₃): 1.05 (9H,s); 1.25 (3H,t); 3.40 (1H,s); 3.15 (2H,q); 7.40 (3H,m); 8.40 (2H,m); 8.80 (2H,s).

(v) Ethyl (RS)-2-[2-(1-methylcyclopropyl)pyrimidin-5-yl]-3,3-dimethylbutanoate.

270 MHz ¹H NMR (CDCl₃): 0.91 (2H,m); 1.00 (9H,s); 1.26 (3H,t); 1.35 (2H,m); 1.57 (3H,s); 3.33 (1H,s); 4.10 (2H,m); 8.65 (2H,s).

GLC Retention Time: 5.86 minutes.

(vi) Ethyl (RS)-2-(2-methylpyrimidin-5-yl)-3,3-dimethylbutanoate.

60 MHz ¹H NMR (CDCl₃): 1.00 (9H,s), 1.25 (3H,t); 2.7 (3H,s); 3.35 (1H,s); 4.2 (2H,q); 8.65 (2H,s).

GLC Retention Time: 3.98 minutes.

(vii) Ethyl (RS)-2-[2-(1,1-dimethylpropyl)-pyrimidin-5-yl]-3,3-dimethylbutanoate 60 MHz ¹H NMR (CDCl₃): 1.05 (9H,s); 0.7-1.4 (8H,m); 1.4 (6H,m); 3.35 (1H,s); 4.2 (2H,2q); 8.8 (2H,s)

GLC Retention Time: 5.69

Molecular Ion: 292

(viii) Ethyl (RS)-2-(2-methylpyrimidin-5-yl)-3-methylbutanoate

¹H NMR (CDCl₃): 0.76 (3H,d); 1.06 (3H,d); 1.25 (3H,t); 2.28-2.44 (1H,m); 2.73 (3H,s); 3.16 (1H,d); 4.10-4.24 (2H,m); 8.64 (2H,s)

(ix) Ethyl (RS)-2-[2-(2-chlorophenyl)pyrimidin-5-yl]-3,3-dimethylbutonate.

90 MHz ¹H NMR (CDCl₃): 1.05 (9H,s); 1.30 (3H,t); 3.45 (1H,s); 4.20 (2H,qd); 7.40 (3H,m); 7.80 (1H,m); 8.95 (2H,s).

(x) Ethyl (RS)-2-[2-(1-methylcyclohexyl)pyrimidin-5-yl]-3,3-dimethylbutanoate.

270 MHz ¹H NMR (CDCl₃): 1.00 (9H,s); 1.25 (3H,t); 1.27 (3H,s); 1.20-1.60 (8H,m); 2.35 (2H,m); 3.35 (1H,s); 4.15 (2H,q); 8.78 (2H,s).

(xi) Ethyl (RS)-2-[2-(trifluoromethyl)pyrimidin-5-yl]-3,3-dimethylbutanoate.

270 MHz ¹H NMR (CDCl₃): 1.00 (9H,s); 1.27 (3H,t); 3.50 (1H,s); 4.20 (2H,dq), 8.98 (2H,s).

(xii) Ethyl (RS)-2-(2-phenylpyrimidin-5-yl)-3-methylbutanoate

¹H NMR (CDCl₃): 0.82 (d,3H); 1.08 (d,3H); 1.30 (t,3H); 2.40 (m,1H); 3.22 (d,1H); 4.26 (q,2H); 7.48 (m,3H); 8.44 (m,2H); 8.80 (s,2H)

EXAMPLE 12

The following compounds were prepared from the appropriate starting materials according to the method of Example 10:

(i) (RS)-2-[2-(1,1-dimethylpropyl)pyrimidin-5-yl]-3,3-dimethylbutanoic acid

60 MHz ¹H NMR (CDCl₃): 0.8 (3H,t); 1.05 (9H,s); 1.5 (6H,s); 1.85 (2H,q); 3.4 (1H,s); 8.8 (2H,s) (acid OH not seen).

GLC Retention Time: 6.25 minutes.

(ii) (RS)-2-(2-methylpyrimidin-5-yl)-3,3-dimethylbutanoic acid

60 MHz ¹H NMR (CDCl₃): 1.05 (9H,s); 2.75 (3H,s); 3.45 (1H,s); 8.1 (1H, broad s); 8.8 (2H,s).

GLC Retention Time: 4.5 minutes (iii) (RS)-2-[2-(1-methylcyclopropyl)pyrimidin-5-yl]-3,3-dimethylbutanoic acid 400 MHz ¹H NMR (CDCl₃): 0.9 (2H,m); 1.05 (9H,s); 1.4 (2H,m); 1.55 (3H,s); 3.4 (1H,s); 8.65 (2H,s) (acid OH not seen).

GLC Retention Time: 6.20 minutes (iv) (RS)-2-(2-cyclopropylpyrimidin-5-yl)-3,3-dimethylbutanoic acid Infra Red (Nujol mull): 2927, 2478, 2347, 1901, 1710, 1592, 1548, 1457, 1331, 1228, 1210, 1170, 1064, 912, 793, 713 and 656 cm⁻¹

Melting Point: 146° C.

(v) (RS)-2-[2-(N,N-Dimethylamino)pyrimidin-5-yl]-3,3-dimethylbutanoic acid

Infra Red (Nujol mull): 2923, 2854, 2528, 1917, 1717, 1611, 1534, 1460, 1413, 1206, 973, 793, 711 and 659 cm⁻¹

Melting Point: 164°-166° C.

(vi) (RS)-2-[2-(1-methylethyl)pyrimidin-5-yl]-3,3-dimethylbutanoic acid

Infra Red (Nujol mull): 2931, 2857, 2347, 1898, 1710, 1592, 1550, 1458, 1369, 1333, 1304, 1232, 1206, 1171, 854, 800, 776 and 719 cm$^{-1}$ Melting Point: 180° C.

(vii) (RS)-2-(2-phenylpyrimidin-5-yl)-3,3-dimethylbutanoic acid

Infra Red (thin film): 2923, 2859, 1711, 1585, 1542, 1460, 1376, 1233, 1203, 1175, 1162, 745 and 695 cm$^{-1}$ Melting Point: 185° C.

(viii) (RS)-2-(2-methylpyrimidin-5-yl)-3-methylbutanoic acid

Infra Red (thin film): 2967, 1724, 1595, 1557, 1453, 1272, 1047, 751, 662 cm$^{-1}$ (ix) (RS)-2-[2-(1,1-dimethylethyl)pyrimidin-5-yl]butanoic acid $^1$H NMR (CDCl$_3$): 1.0 (3H,t); 1.4 (9H,s); 1.8–2.4 (2H,m); 3.5 (1H,t); 6.8 (1H,broad s); 8.65 (2H,s)

GLC Retention Time: 4.69 minutes (x) (RS)-2-[2-(2-chlorphenyl)pyrimidin-5-yl]-3,3-dimethylbutanoic acid $^1$H NMR (CDCl$_3$): 1.05 (9H,s); 3.45 (1H,s); 7.40 (2H,m); 7.50 (1H,m); 7.75 (1H,m); 8.95 (1H,m)

(xi) (RS)-2-[2-(1-methylcyclohexyl)pyrimidin-5-yl]-3,3-dimethylbutanoate

270 MHz $^1$H NMR (CDCl$_3$): 1.05 (9H,s); 1.25 (3H,s); 1.20–1.60 (8H,m); 2.30 (2H,m); 3.42 (1H,s); 8.78 (2H,s)

EXAMPLE 13

The Example illustrates an alternative procedure for the preparation of Ethyl (RS)-2-[2-(1,1-dimethylethyl)-pyrimidin-5-yl]-3,3-dimethylbutanoate.

(i) Preparation of Ethyl 2-oxo-2-[2-(1,1-dimethylethyl)pyrimidin-5-yl]acetate

Magnesium turnings (1.9 g), a catalytic amount of iodine and dry tetrahydrofuran (50 cm$^3$) were placed in a round-bottomed flask under an atmosphere of dry nitrogen. A portion of a solution of 5-bromo-2-(1,1-dimethylethyl)pyrimidine (15.2 g) in dry tetrahydrofuran (50 cm$^3$) was added to the reaction vessel and the Grignard reaction was initiated by the addition of a small portion of methyl iodide, followed by heating the reaction contents to the reflux temperature. The remainder of the pyrimidine solution was added at such a rate so as to maintain reflux, and on completion of the addition and cessation of reaction, the so formed Grignard reagent was added to a solution of diethyl oxalate (20.4 g) in dry tetrahydrofuran, whilst the reaction temperature was maintained between −10° C. and −15° C. After the addition was complete, the reaction mixture was allowed to warm to the ambient temperature, at which point it was allowed to stir for 16 hours. Dilute aqueous hydrochloric acid was added to the reaction mixture which was then extracted into dichloromethane. The combined organic extracts were washed with water, and brine, and dried over anhydrous magnesium sulphate. Evaporation of the solvent under reduced pressure, and short-path distillation of the residue using a Kugelrohr apparatus gave ethyl 2-oxo-2-[2-(1,1-dimethylethyl)-pyrimidin-5-yl]-acetate (9.3 g).

Boiling point 140° C./0.08 mmHg.

90 MHz $^1$H NMR (CDCl$_3$): 1.45 (9H,s); 1.45 (3H,t); 4.45 (2H,q); 9.30 (2H,s).

GLC Retention Time: 4.05 minutes.

(ii) Preparation of Ethyl (RS)-2-hydroxy-2-[2-(1,1-dimethylethyl)pyrimidin-5-yl]-3,3-dimethylbutanoate.

A 2 molar solution of (1,1-dimethylethyl) magnesium chloride in diethyl ether (5 cm$^3$) was added in portions to a solution of ethyl 2-oxo-2-[2-(1,1-dimethylethyl)-pyrimidin-5-yl]acetate (2.36 g) in dry tetrahydrofuran whilst the reaction temperature was maintained at −78° C. After the addition was complete, the reaction mixture was allowed to warm to the ambient temperature, and to stand overnight. Water was added, and the products were extracted into ethyl acetate. The combined organic extracts were washed, and dried over anhydrous magnesium sulphate.

After removal of the solvent by evaporation under reduced pressure, the residue was subjected to column chromatography on silica gel using hexane containing 10% ethyl acetate by volume as eluent, to give ethyl (RS)-2-hydroxy-2-[2-(1,1-dimethylethyl)pyrimidin-5-yl]-3,3-dimethylbutanoate (0.65 g) as a colourless oil.

90 MHz $^1$H NMR (CDCl$_3$): 1.0 (9H,s); 1.3 (3H,t); 1.4 (9H,s); 3.9 (1H, broad s); 4.4 (2H, 9.05 (2H,s)

(iii) Preparation of Ethyl (RS)-2-chloro-2-[2(1,1-dimethylethyl)pyrimidin-5-yl]-3,3-dimethylbutanoate Thionyl chloride (0.57 g) was added dropwise to a solution of ethyl (RS)-2-hydroxy-2-[2-1,1-dimethylethyl)pyrimidin-5-yl]-3,3-dimethylbutanoate (0.2 g) and imidazole (0.32 g) in dry acetonitrile (7 cm$^3$), whilst the reaction temperature was maintained at 0° C. The mixture was allowed to warm to the ambient temperature and stirred for a period of sixteen hours, after which time it was poured into water, and extracted into dichloromethane. The combined organic extracts were washed with water, dried over anhydrous magnesium sulphate, passed through a short plug of silica, and concentrated by evaporation of the solvent under reduced pressure to give ethyl (RS)-2-chloro-2-[2-(1,1-dimethylethyl)pyrimidin-5-yl]-3,3-dimethylbutanoate as a yellow oil (0.15 g).

270 MHz $^1$H NMR (CDCl$_3$): 1.09 (9H,s); 1.25 (3H,t); 1.35 (9H,s); 4.25 (2H,2q); 8.85 (2H,s).

(iv) Ethyl (RS)-2-[2-(1,1-dimethylethyl)pyrimidin-5-yl]-3,3-dimethylbutanoate

Tri-n-Butyl tin hydride (1.3 cm$^3$) was added to a solution of ethyl (RS)-2-chloro-2-[2-(1,1-dimethylethyl)pyrimidin-5-yl]-3,3-dimethylbutanoate (1.4 g) and a catalytic amount of 2,2'-azobisisobutyronitrile in dry toluene (10 cm$^3$). The mixture was heated to the reflux temperature for a period of 1½ hours, after which it was cooled to the ambient temperature, poured into water, and extracted into ethyl acetate. After concentration by evaporation of the solvent under reduced pressure, the residue was subjected to column chromatography on silica gel using hexane followed by ethyl acetate as eluent to give ethyl (RS)-2-[2-(1,1-dimethyl-ethyl)-pyrimidin-5-yl]-3,3-dimethylbutanoate (1.1 g) as a pale yellow liquid, the spectral data of which were identical to those obtained for the sample generated in Example 9.

EXAMPLE 14

Ethyl (RS)-2-[2-(1,1-dimethylethyl)pyrimidin-5-yl]-3,3-dimethylpentanoate was prepared from ethyl 2-oxo-2-[2-(1,1-dimethylethyl)pyrimidin-5-yl]acetate and 1,1-dimethylpropyl magnesium chloride using the method described in Example 13.

$^1$H NMR (CDCl$_3$): 0.92 (6H,m); 1.00 (3H,s); 1.20–1.30 (4H,m); 1.30–1.40 (1H,m); 1.42 (9H,s); 3.45 (1H,s); (4.05–4.25 (2H,m); 8.75 (2H,s)

GLC Retention Time: 5.81 minutes.

EXAMPLE 15

This Example illustrates an alternative procedure for the preparation of (RS)-2-[2-(1,1-dimethylethyl)pyrimidin-5-yl]-3,3-dimethylbutanoic acid.

(i) Preparation of 2,2-dimethyl-1-hydroxy-1-[2-(1,1-dimethylethyl)pyrimidin-5-yl]propanol Magnesium turnings (0.42 g), a catalytic amount of iodine, and dry tetrahydrofuran (5 cm$^3$) were placed in a round-bottomed flask under an atmosphere of dry nitrogen. A portion of a solution of 5-bromo-2-(1,1-dimethylethyl)pyrimidine (3.1 g) in dry tetrahydrofuran (10 cm$^3$) was added to the reaction pot, and the Grignard reaction was initiated by warming of the reaction mixture to the reflux temperature; the remainder of the pyrimidine solution was added at such a rate so as to maintain reflux. After the addition was complete, and the reflux had subsided, the reaction mixture was cooled to 10° C., and a solution of pivaldehyde (1.5 cm$^3$) in dry tetrahydrofuran (5 cm$^3$) was slowly added.

After the addition was complete, the reaction mixture was stirred for 5 minutes, quenched with aqueous ammonium chloride solution, and extracted into ethyl acetate. The combined organic extracts were washed, dried over anhydrous magnesium sulphate, and concentrated by evaporation of the solvent under reduced pressure, to give 2,2-dimethyl-1-hydroxy-1-[2-(1,1-dimethylethyl)pyrimidin-5-yl]propan-1-ol as a pale solid.

90 MHz $^1$H NMR (CDCl$_3$): 0.95 (9H,s); 1.25 (9H,s); 2.2 (1H, broad s); 4.4 (1H,s); 8.6 (2H,s).

GLC Retention Time: 4.07 minutes (ii) Preparation of 3,3-dimethyl-2-[2-(1,1-dimethylethyl)pyrimidin-5-yl]butyronitrile (a) Methane sulphonyl chloride (0.17 cm$^3$) was added to a solution of 2,2-dimethyl-1-[2-(1,1-dimethylethyl)pyrimidin-5-yl]propan-1-ol (0.44 g) and a catalytic amount of 4-dimethylaminopyridine in dry pyridine (3 cm$^3$) was added to the mixture.

After stirring for 16 hours at the ambient temperature, the reaction solution was poured into water, extracted into ethyl acetate, and the organic fractions washed with dilute aqueous hydrochloric acid, water and brine. The organic solution was dried over anhydrous magnesium sulphate and concentrated by evaporation of the solvent under reduced pressure.

GLC Retention Time: 6.04 minutes

This intermediate mesylate was not further characterised, but immediately added to a solution of sodium cyanide (0.10 g) in dry dimethyl sulphoxide (4 cm$^3$), and heated to 60° C. for 4 hours. After cooling to the ambient temperature, the reaction mixture was diluted with water, extracted into ethyl acetate, washed with water and brine, and dried over anhydrous magnesium sulphate. Evaporation of the solvent under reduced pressure gave 3,3-dimethyl-2-[2-(1,1-dimethylethyl)pyrimidin-5-yl]butyronitrile (0.25 g).

60 MHz $^1$H NMR (CDCl$_3$): 1.1 (9H,s); 1.43 (9H,s); 3.55 (1H,s); 9.62 (2H,s).

Molecular Ion: 231

(iii) An alternative process for the preparation of the butyronitrile stage (ii) is described below:

(a) Preparation of 1-chloro-2,2-dimethyl-1-[2-(1,1-dimethylethyl)pyrimidin-5-yl]propane A solution of 2,2-dimethyl-1-[2-(1,1-dimethylethyl)pyrimidin-5-yl]propan-1-ol (19.37 g) in thionyl chloride (125 cm$^3$) was heated at the reflux temperature for 30 minutes. After cooling to the ambient temperature, the excess thionyl chloride was removed by evaporation under reduced pressure, and the residue dissolved in dichloromethane and washed with aqueous sodium bicarbonate solution. After drying over anhydrous magnesium sulphate, concentration of the organic solution by evaporation of the solvent under reduced pressure gave 1-chloro-2,2-dimethyl-1-[2-(1,1-dimethylethyl)pyrimidin-5-yl]propane (20.95 g).

Infra Red (Nujol Mull): 2924, 2854, 1586, 1540, 1460, 1434, 1365, 1156, 859, 834 and 774 cm$^{-1}$ GLC Retention Time: 3.72 minutes (b) Preparation of 3,3-dimethyl-2-[2-(1,1-dimethylethyl)pyrimidin-5-yl]butyronitrile.

A solution of 1-chloro-2,2-dimethyl-1-[2-(1,1-dimethylethyl)pyrimidin-5-yl]propane (5.08 g) and sodium cyanide (2.07 g) in dry dimethylsulphoxide (50 cm$^3$) was heated to 60° C., under an atmosphere of dry nitrogen for a period of 17 hours. After cooling to the ambient temperature, the solution was poured into aqueous sodium bicarbonate solution and extracted with diethyl ether, washed with brine, dried over anhydrous magnesium sulphate, and concentrated by evaporation of the solvent under reduced pressure. The resulting brown oil was combined with the crude product from a similar reaction and subjected to column chromatography on silica gel using dichloromethane followed by dichloromethane containing 5% by volume ethyl acetate to give 3,3-dimethyl-2-[2-(1,1-dimethylethyl)pyrimidin-5-yl]butyronitrile (7.6 g), identical in all respects to the material obtained in Example 15 (ii) above.

(iv) Preparation of (RS)-2-[2-(1,1-dimethylethyl)pyrimidin-5-yl]-3,3-dimethylbutanoic acid A solution of 3,3-dimethyl-2-[2-(1,1-dimethylethyl)pyrimidin-5-yl]butyronitrile (13.3 g) in a mixture of concentrated sulphuric acid (100 cm$^3$) and water (20 cm$^3$) was heated to 80° C. for 2 hours.

GLC Analysis of a withdrawn sample of the mixture then showed the absence of starting material, but the presence of a new peak with retention time 6.29 minutes. The cooled reaction mixture was added dropwise to a solution of sodium nitrite (25.78 g) in water (50 cm$^3$) at the ambient temperature.

Two hours after the addition was complete the reaction mixture was taken to pH 10 by addition of solid and aqueous sodium carbonate, and washed with ethyl acetate. The aqueous fraction was acidified to pH 4 to 5 with concentrated aqueous hydrochloric acid and extracted with chloroform, and the combined organic extracts were dried over anhydrous magnesium sulphate and concentrated by evaporation of the solvent under reduced pressure to give (RS)-2-[2-(1,1-dimethylethyl)pyrimidin-5-yl)-3,3-dimethylbutanoic acid, identical to the material generated in Example 10.

EXAMPLE 16

This Example illustrates the preparation of methyl (RS)-2-[2-(1,1-dimethylethyl)pyrimidin-5-yl]-3,3,3-trifluoropropionate.

(i) 2-(1,1-dimethylethyl)-5-trifluoroacetylpyrimidine

A solution of 5-bromo-2-(1,1-dimethylethyl)pyrimidine (3.133 g) in dry tetrahydrofuran (5 cm$^3$) was added in portions to a mixture of magnesium turnings (Grignard quality, 0.40 g) in tetrahydrofuran (5 cm$^3$) and a crystal of iodine as catalyst. The reaction was stirred under a nitrogen atmosphere and the reaction allowed to warm to the reflux temperature by controlling the addition of the bromopyrimidine. When the addition was complete the mixture was stirred for a further 30 minutes. To the stirred mixture at the ambient temperature was added (in portions) dry N,N-dimethyltrifluoroacetamide (2.088 g) and the reaction was stirred for an additional 1 hour after complete addition. The reaction was treated with saturated aqueous ammonium chloride solution, and extracted (twice) with ethyl acetate). The organic fractions were combined, dried (magnesium sulphate) and the solvent evaporated under reduced pressure to yield a brown oil (3.09 g). The oil was distilled (b.p ca 100° C./12 mm Hg) to give a pale yellow semi solid (2.35 g). Infra Red Spectroscopy indicated this product to be the hydrate of the required ketone.

The semi-solid (2.2 g) was mixed with phosphorous pentoxide (2.34 g), heated to 100° C. and distilled from the residue under a dry nitrogen atmosphere at reduced pressure (b 12 mm Hg) to yield a colourless liquid (ca 1.6 g). The product was stored under dry nitrogen to avoid rehydration.

Infra Red (liquid film): 2965, 1729, 1583, 1533, 1483, 1440, 1388, 1364, 1217, 1148, 939, 822, 759, 723 cm$^{-1}$.
Molecular Ion: 232
GLC Retention Time: 1.39 minutes (ii) 1,1-dichloro-2-[2-(1,1-dimethylethyl)-pyrimidin-5-yl]-3,3,3-trifluoroprop-1-ene 2-(1,1-dimethylethyl-5-trifluoroacetylpyrimidine (0.9 g) was dissolved in dry carbon tetrachloride (15 cm$^3$) containing triphenylphosphine (2.5 g). The reaction mixture was stirred under a nitrogen atmosphere and heated at the reflux temperature for 30 hours to give a deep red-brown solution. The reaction mixture was fractioned by filtering the cooled solution through a short column of silica gel and eluting with a mixture of hexane/dichloromethane (3:1 by volume). On evaporation of the solvents the product was obtained as a colourless solid (0.9 g)
Melting Point 58° C.
$^1$H NMR (CDCl$_3$): 1.45 (s,9H), 8.60 (s,2H)
GLC Retention Time: 2.60 minutes (iii) Methyl (RS)-2-[2-(1,1-dimethylethyl)pyrimidin-5-yl]-3,3,3-trifluoropropionate.

1,1-dichloro-2-[2-(1,1-dimethylethyl)pyrimidin-5-yl]-3,3,3-trifluoroprop-1-ene (0.40 g) was dissolved in dry methanol (10 cm$^3$) containing potassium hydroxide (0.22 g). The reaction mixture was stirred at the ambient temperature for 5 hours.

A sample was withdrawn from the reaction mixture, diluted with water and extracted into ethyl acetate.

GLC/MS analysis showed this to contain a mixture of (i) E and Z 1-chloro-1-methoxy-2-[2-(1,1-dimethylethyl)pyrimidin-5-yl]-3,3,3-trifluoroprop-1-ene (GLC Retention Time: 3.15, 3.32 minutes, Molecular Ion: 294), (ii) 1,1-dimethoxy-2-[2-(1,1-dimethylethyl)pyrimidin-5-yl]-3,3,3-trifluoroprop-1-ene (GLC Retention Time: 3.67 minutes) and (iii) methyl (RS)-2-[2-(1,1-dimethylethyl)pyrimidin-5-yl]-3,3,3-trifluoropropionate (GLC Retention Time: 2.64 minutes, Molecular Ion: 276).

After a further 18 hours at the ambient temperature the mixture was partially evaporated under reduced pressure (to ca 3 cm$^3$ in volume) and acidified with concentrated hydrochloric acid to pH1. The reaction mixture was stirred at the ambient temperature for 4 hours, extracted with dichloromethane, washed with water and dried (anhydrous magnesium sulphate). The solvent was evaporated to yield an oil which was fractionated by eluting through a column of silica gel with dichloromethane/ethyl acetate (100:5 by volume). The product was obtained as a colourless oil [0.15 g].
$^1$H NMR (CDCl$_3$): 1.40 (s,9H), 3.85 (s,3H), 4.30 (q,1H), 89.75 (s,2H)
GLC Retention Time: 2.64 minutes.

EXAMPLE 17

This Example illustrates the preparation of (RS)-2-[2-(1,1-dimethylethyl)pyrimidin-5-yl]-3,3-dimethylpent-4-enoic acid.

(i) 3-methylbut-2-en-1-yl 2-[2-(1,1-dimethylethyl]pyrimidin-5-yl]acetate

Prepared according to the esterification process described in Example 19, 1 Method 1 from 3-methylbut-2-en-1-ol and 2-[2-(1,1-dimethylethyl)pyrimidin-5-yl]acetic acid
$^1$H NMR (CDCl$_3$): 1.45 (9H,s); 1.70 (3H,s); 1.75 (3H,s); 3.60 (2H,s); 4.65 (2H,d); 5.35 (1H,m); 8.60 (2H,s)
GLC Retention Time: 5.72 minutes (ii) 2-[2-(1,1-dimethylethyl)pyrimidin-5-yl]-3,3-dimethylpent-4-enoic acid 3-methylbut-2-en-1-yl 2-[2-(1,1-dimethylethyl)-pyrimidin-5-yl]acetate (0.366 g) was dissolved in dry toluene (5 cm$^3$) containing sodium amide (0.068 g) and heated to the reflux temperature with stirring under a nitrogen atmosphere. After heating for 2½ hours the reaction was cooled to the ambient temperature and diluted with water. The organic layer was separated and the aqueous fraction re-extracted with ethyl acetate. The aqueous layer was acidified (2M HCl) and extracted with chloroform (3 times). The chloroform fractions were combined, dried (MgSO$_4$) and evaporated under reduced pressure to give a light brown solid (0.283 g) shown by GLC analysis to contain a major component in 70% purity, identified as (RS)-2-[2-(1,1-dimethylethyl)pyrimidin-5-yl]-3,3-dimethylpent-4-enoic acid.
GLC Retention Time: 6.0 minutes (70%).
Molecular Ion: 262

A second component (19%) was identified as 2-[2-(1,1-dimethylethyl)pyrimidin-5-yl]acetic acid.
GLC Retention Time: 4.0 minutes.

EXAMPLE 18

This Example illustrates the preparation of ethyl (RS)-2-(2-chloropyrimidin-5-yl)-3-methylbutanoate.

(i) Preparation of ethyl (RS)-2-(2-aminopyrimidin-5-yl)-3-methylbutanoate

A solution of sodium methoxide (0.9 g) in ethanol (5 cm$^3$) was added dropwise to a stirred suspension of guanidine hydrochloride (1.58 g) and ethyl (RS)-4-dimethylamino-3-formyl-2-(1-methylethyl)-3-butenoate in ethanol (10 cm$^3$). The reaction mixture was heated at the reflux temperature for 2 hours, then stood at the ambient temperature for 70 hours. The solvent was evaporated under reduced pressure and water added to the residue.

The reaction products were extracted into ethyl acetate, and the combined organic layers dried over anhydrous magnesium sulphate. Evaporation of the solvent under reduced pressure gave the title compound (1.08 g) as an oil which crystallised on standing.
$^1$H NMR (CDCl$_3$): 0.78 (3H,d); 1.02 (3H,d); 1.23 (3H,t); 2.23 (1H,m); 2.97 (1H,d); 4.15 (2H,q); 5.23 (2H,broad s); 8.25 (2H,s).

Molecular Ion: 223

(ii) Preparation of Ethyl (RS)-2-(2-chloropyrimidin-5-yl)-3-methylbutanoate and ethyl (RS)-2-pyrimidin-2-one-5-yl)-3-methylbutanoate.

A solution of sodium nitrite (1.33 gm) in water (5 cm³) was added dropwise to a cooled solution of ethyl (RS)-2-(2-aminopyrimidin-5-yl)-3-methylbutanoate (1.08 g) in concentrated aqueous hydrochloric acid solution (14.5 cm³), the temperature of the reaction mixture being maintained at less than 5° C. during the addition. The mixture was stirred at 0° C. for 3 hours, then allowed to warm to the ambient temperature and stood for 16 hours. The mixture was then cooled in an ice bath and neutralised by dropwise addition of aqueous potassium carbonate solution (the temperature of the mixture being maintained below 4° C.). The products were extracted into dichloromethane, the organic layers being washed with water and dried over anhydrous magnesium sulphate. Removal of the solvent by evaporation under reduced pressure gave a mixture of two products which was separated by column chromatography on a silica gel support, eluting firstly with dichloromethane containing 2% by volume ethyl acetate to give ethyl (RS)-2-(2-chloropyrimidin-5-yl)-3-methylbutanoate (0.27 g), Product A, and secondly with dichloromethane containing 10% by volume methanol to give ethyl (RS)-2-(pyrimidin-2-one-5-yl)-3-methylbutanoate, (0.34 g), Product B.

PRODUCT A

¹H NMR (CDCl₃): 0.80 (3H,d); 1.08 (3H,d); 1.30 (3H,t); 1.32 (1H,m); 1.22 (1H,d); 4.16 (2H,m); 8.64 (2H,s)
Molecular ion: 242

PRODUCT B

Melting Point: 142°-144° C.
Molecular ion: 296

EXAMPLE 19

This Example illustrates five alternative esterification processes for preparing the esters of formula (I) according to the invention.

METHOD 1 dicyclohexylcarbodiimide coupling of acid and alcohol

Preparation of 2,3,5,6-tetrafluoro-4-(methoxymethyl)benzyl (RS)-2-[2-(1,1-dimethylethyl)pyrimidin-5-yl]-3,3-dimethylbutanoate (Compound No. 15).

A solution of (RS)-2-[2-(1,1-dimethylethyl)pyrimidin-5-yl]-3,3-dimethylbutanoic acid (0.1 g), 2,3,5,6-tetrafluoro-4-(methoxymethyl)benzyl alcohol (0.089 g) and 4-dimethylaminopyridine (0.002 g) in dry dichloromethane (4 cm³) was stirred at the ambient temperature (20° C.) whilst N,N'-dicyclohexylcarbodiimide (0.084 g) was added in portions; the mixture was stirred for 18 hours. The solution was passed through silica gel and the silica gel eluted with, firstly, dichloromethane and, secondly a 50:1 mixture (by volume) of dichloromethane and ethyl acetate Evaporation of the solvents of the combined filtrate and eluted fractions gave the title compound (0.09 g) as a colourless oil.
¹H NMR (CDCl₃): 1.0 (9H,s); 1.5 (9H,s); 3.4 (4H,broad s); 3.6 (2H,broad s); 5.25 (2H,q); 8.72 (2H,s).
GLC Retention Time: 8.14 minutes.
Molecular ion: 456

METHOD 2

1-ethyl-3-(dimethylaminopropyl)carbodiimide coupling of acid and alcohol

Preparation of 2,3,5,6-tetrafluoro-4-(methoxymethyl)-benzyl (RS)-2-(2-methylpyrimidin-5-yl)-3,3-dimethylbutanoate (Compound No 120).

A solution of 1-ethyl-3-(3-dimethylaminopropyl)carbodiimide hydrochloride (0.276 g) in dry dichloromethane (6 cm³) was added to a stirred solution of (RS)-2-(2-methylpyrimidin-5-yl)-3,3-dimethylbutanoic acid (0.3 g) and 4-(methoxymethyl)-2,3,5,6-tetrafluorobenzylalcohol (0.33 g) containing a catalytic amount of 4-(N,N'-dimethylamino) pyridine. The stirred mixture was maintained at the ambient temperature for 2 hours, and left to stand overnight. The reaction solution was washed with water, dried over anhydrous magnesium sulphate and concentrated by evaporation of the solvent under reduced pressure. The residue was subjected to column chromatography on silica gel using a 1:1 (by volume) mixture of ethyl acetate and dichloromethane as eluent to give 2,3,5,6-tetrafluoro-4-(methoxymethyl)-benzyl (RS)-2-(2-methylpyrimidin-5-yl)-3,3-dimethylbutanoate (0.228 g) as a yellow oil.
270 MHz ¹H NMR (CDCl₃): 0.99 (9H,s); 2.73 (3H,s); 3.38 (1H,s); 3.40 (3H,s); 4.58 (2H,s); 5.2 (1H,d); 5.3 (1H,d); 8.68 (2H,s).
GLC Retention Time: 8.98 minutes.

METHOD 3

Base catalysed reaction of acid with halide, mesylate or tosylate derivative of alcohol Preparation of 4-fluoro-3-phenoxybenzyl (RS)-2-(2-methylpyrimidin-5-yl)-3,3,-dimethylbutanoate (compound No 206).

Solid potassium carbonate (0.4 g) was added to a solution of 4-fluoro-3-phenoxybenzyl bromide (0.4 g) and (RS)-2-(2-methylpyrimidin-5-3,3-dimethylbutanoic acid (0.3 g) in acetone (20 cm³), and the mixture was stirred for a period of 6 hours. After standing for a further 2 days, the reaction mixture was filtered, the residue washed with acetone, and the combined filtrate and acetone washings concentrated by evaporation of the solvent under reduced pressure to give an orange oil. Column chromatography on silica gel using dichloromethane followed by ethyl acetate as eluent gave 4-fluoro-3-phenoxybenzyl (RS)-2-(2-methylpyrimidin-5-yl)-3,3-dimethylbutanoate (0.33 g) as an orange oil, which solidified on standing.
270 MHz ¹H NMR (CDCl₃): 0.95 (9H,s); 2.72 (3H,s); 3.38 (1H,s); 4.95 (1H,d); 5.1 (1H,d); 6.9-7.4 (8H,m); 8.67 (2H,s).
GLC Retention Time: 11.42 minutes.

METHOD 4

Titanium alkoxide catalysed transesterification between simple alkyl ester and alcohol)

Preparation of 2,3,5,6-tetrafluoro-4-methylbenzyl (RS)-2-[2-(1,1-dimethylethyl)pyrimidin-5-yl]-3,3-dimethylbutanoate (compound No. 4).

A mixture of ethyl (RS)-2-[2-(1,1-dimethylethyl)-pyrimidin-5-yl]-3,3-dimethylbutanoate (0.07 g), 2,3,5,6-tetrafluoro-4-methylbenzyl alcohol (0.1 g), titanium VI ethoxide (catalytic amount) and dry toluene (2 cm³) was heated at the reflux temperature for 10 hours. After cooling, the solvent was evaporated under reduced pressure to leave a brown gum, which was purified by preparative thin layer chromatography on 20 cm×20 cm×0.2 cm silica gel plates, eluting with dichloromethane containing 2% by volume ethyl acetate, to give the title compound (0.05 g) as an oil which solidified on standing.
Melting Point: 91° C.
$^1$H NMR (CDCl$_3$): 1.0 (9H,s); 1.4 (9H,s); 2.28 (3H, broad s); 3.38 (1H,s); 5.18 (2H,q); 8.72 (2H,s).
GLC Retention Time: 8.57 minutes.
Molecular ion: 426

METHOD 5

Reaction between acid chloride and alcohol or thioalcohol

Preparation of 4-hydroxymethyl-2,3,4,6-tetrafluorobenzyl (RS)-2-[2-(1,1-dimethylethyl)pyrimidin-5-yl]-3,3-dimethylbutanthioate (compound No. 196).

(RS)-2-[2(1,1-dimethylethyl)pyrimidin-5-yl]-3,3-dimethylbutanoic acid (0.20 g) was treated with thionyl chloride (2 cm$^3$) and heated to reflux with stirring for 2.5 hours. Unreacted thionyl chloride was evaporated under reduced pressure to leave a gum containing (RS)-2-[2-(1,1-dimethylethyl)pyrimidin-5-yl]-3,3-dimethylbutanoyl chloride. The gum was dissolved in dry dichloromethane (3 cm$^3$) and added dropwise at the ambient temperature to a stirred solution of 4-hydroxymethyl-2,3,5,6-tetrafluorobenzylmercaptan (0.181 1 g) in dry dichloromethane (2 cm$^3$) containing dry triethylamine (0.1 cm$^3$). The reaction mixture was stirred for 2 hours and further triethylamine (0.05 cm$^3$) added. After stirring for a further 4 hours the mixture was diluted with dichloromethane and dilute hydrochloric acid. The organic layer was separated and the aqueous fraction extracted with further dichloromethane. The organic fractions were combined, washed with water and dried over anhydrous magnesium sulphate. The solvent was evaporated under reduced pressure to yield an oil (0.30 g).

This oil was fractionated by eluting through a bed of silica gel (Merck 7729) with (1) dichloromethane and (2) dichloromethane/ethyl acetate (100:5 by volume) to give the required thioester as a colourless solid (0.13 g).
Melting point 38°-41° C.
$^1$H NMR (CDCl$_3$): 1.0 (s,9H); 1.40 (s,9H); 2.1 (t,1H); 3.50 (s,1H); 4.20 (dd,2H); 4.80 (d,2H); 8.65 (s,2H)
GLC Retention Time: 14.36 minutes.

EXAMPLE 20

The following esters were prepared from the appropriate starting materials according to one of the methods described in Example 19.
(i) 2,3,5,6-tetrafluoro-4-(prop-2-yn-1-yl)benzyl (RS)-2-[2-(1,1-dimethylethyl)pyrimidin-5-yl]-3,3-dimethylbutanoate (compound No. 12) using method 1.
$^1$H NMR (CDCl$_3$): 1.0 (9H,s); 1.4 (9H,s); 2.05 (1H, m); 3.4 (1H,s); 3.6 (2H,broad s); 5.4 (2H,q); 8.75 (2H,s).
GLC Retention Time: 9.55 minutes.
Molecular ion: 450
(ii) 2,3,5-trifluoro-6-methoxy-4-(methoxymethyl)benzyl (RS)-2-[2-(1,1-dimethylethyl)pyrimidin-5-yl]-3,3-dimethylbutanoate (compound No. 16) using method 3 or 4.
$^1$H NMR (CDCl$_3$): 1.0 (9H,s); 2.4 (9H,s); 3.38 (1H,s); 3.4 (3H,s); 3.9 (3H, broad s); 4.56 (2H,broad s); 5.2 (2H,q); 8.75 (2H,s).
GLC Retention time: 10.3 minutes.
Molecular ion: 468
(iii) 2,3,5,6-tetrafluoro-4-(prop-2-en-1-yl)benzyl (RS)-2-2-trifluoromethylpyrimidin-5-yl)-3-methylbutanoate (compound No. 114) using method 4.
$^1$H NMR (CDCl$_3$): 0.8 (3H,d); 1.04 (3H,d); 2.4 (1H,m); 3.4 (3H,m); 5.08 (4H,m); 5.8 (1H,m); 8.88 (2H,s).
Molecular ion: 450
(iv) 2,3,5,6-tetrafluoro-4-(prop-2-yn-1yl)benzyl (RS)-2-(2-trifluoromethylpyrimidin-5-yl)-3-methylbutanoate (compound No. 87) using method 1.
$^1$H NMR (CDCl$_3$): 0.8 (3H,d); 1.04 (3H,d); 2.06 (1H,m); 2.40 (1H,m); 3.36 (1H,d); 3.64 (2H,broad); 5.26 (2H,q); 8.86 (2H,s).
(v) 2,3,5,6-tetrafluoro-4-(methoxymethyl)benzyl (RS)-2(2-trifluoromethylpyrimidin-5-yl)-3-methylbutanoate (compound No. 116) using method 1.
$^1$H NMR (CDCl$_3$): 0.80 (3H,d); 1.06 (3H,d); 2.04 (1H,m); 3.36 (1H,d); 3.41 (3H,s); 4.58 (2H,broad); 5.28 (2H,broads); 8.88 (2H,s).
Molecular ion: 454
(vi) 2,3,5,6-tetrafluoro-4-(prop-2-en-1-yl)benzyl (RS)-2-[2-(N,N-dimethylamino)pyrimidin-5-yl]-3-methylbutanoate (compound No. 115) using method 4.
$^1$H NMR (CDCl$_3$): 0.76 (3H,d); 1.00 (3H,d); 1.26 (1H,m); 3.00 (1H,d); 3.18 (6H,s); 3.48 (2H,m); 5.16 (4H,m); 5.88 (1H,m); 8.25 (2H,s).
Molecular ion: 425
(vii) 2,3,5,6-tetrafluoro-4-(prop-2-en-1-yl)benzyl (RS)-2-(2-trichloromethylpyrimidin-5-yl)-3-methylbutanoate (compound No. 117) using method 4.
$^1$H NMR (CDCl$_3$): 0.80 (3H,d); 1.02 (3H,d); 2.40 (1H,m); 3.34 (1H,d); 3.46 (2H,m); 5.04 (4H,m); 5.88 (1H,m); 8.86 (2H,s).
Molecular ion: 498
(viii) 4-fluoro-3-phenoxybenzyl (RS)-2-[2-(1,1-dimethylethyl)pyrimidin-5-yl]-2-cyclopropylacetate (compound No. 125) using method 1.
$^1$H NMR (CDCl$_3$): 0.16 (1H,m); 0.40 (1H,m); 0.60 (2H,m); 1.36 (1H,m); 1.41 (9H,s); 2.80 (1H,d); 5.08 (2H,d); 7.40–6.94 (8H,m); 8.66 (2H,s).
GLC Retention Time: 10.45 minutes.
Molecular ion: 434.
(ix) (RS)-1-(6-phenoxyprid-2-yl)ethyl (RS)-2-[2-(1,1-dimethylethyl)pyrimidin-5-yl]-2-cyclopropylacetate. (compound No. 90) using method 1.
$^1$H NMR (CDCl$_3$): 0.20–0.66 (4H,m); 1.42 (9H,s); 1.42 (1H,m); 1.52 (3H,m); 2.84 (1H,d); 5.84 (1H,m); 6.70 (1H,t); 6.86, 6.94 (1H, 2d); 7.14 (2H,m); 7.20 (1H,m); 7.38 (2H,m); 7.60 (1H,2t); 8.68 (2H,d)
GLC Retention Time: 10.17, 10.26 minutes. (mixture of diastereoisomers)
Molecular ion: 431.
(x) 3,5,6-trifluoro-2-methoxy-4-(methoxymethyl)benzyl (RS)-2-[2-(1,1-dimethylethyl)pyrimidin-5-yl]-2-cyclopropylacetate (compound No. 92) using method 1.
$^1$H NMR (CDCl$_3$): 0.18 (1H,m); 0.46 (1H,m); 0.60 (1H,m); 0.72 (1H,m); 1.41 (9H,s); 1.44 (1H,m); 2.80 (1H,d); 3.41 (3H,s); 3.85 (3H,s); 4.59 (2H,s); 5.24 (2H,s); 8.67 (2H,s).
GLC Retention Time: 8.95 minutes.
Molecular ion: 452
(xi) 2,3,5,6-tetrafluoro-4-(prop-2-yn-1-yl)benzyl (RS)-2-[2-1,1-dimethylethyl)pyrimidin-5-yl]-2-cyclopropylacetate (compound 91) using method 1.

¹H NMR (CDCl₃): 0.18 (1H,m); 0.44 (1H,m); 0.62 (1H,m); 0.72 (1H,m); 1.41 (1H,m); 1.41 (9H,s); 2.08 (1H,m); 2.82 (1H,d); 3.64 (2H,broad s); 5.27 (2H,s); 8.68 (2H,s).

GLC Retention Time: 8.15 minutes.

(xii) 2,3,5,6-tetrafluoro-4-(prop-2-en-1-yl)benzyl (RS)-2-[2-(1,1-dimethylethyl)pyrimidin-5-yl]butanoate. (compound No. 123) using method 1.

¹H NMR (CDCl₃): 0.95 (3H,t); 1.4 (9H,s); 1.85, 2.15 (2H,m); 3.45 (2H,d); 3.45 (1H,t); 5.1 (2H,2d); 5.9 (1H,m); 5.2 (2H,2d); 8.6 (2H,s).

GLC Retention Time: 8.26 minutes.

(xiii) 2,3,5,6-tetrafluoro-4-methyl (RS)-2-[2-(1,1-dimethylethyl)pyrimidin-5-yl]butanoate (compound No. 122) using method 1.

¹H NMR (CDCl₃): 0.9 (3H,t); 1.4 (9H,s); 1.8, 2.15 (2H,m); 2.3 (3H,t); 3.45 (2H,t); 5.2 (2H,2d); 8.6 (2H,s).

GLC Retention Time: 7.52 minutes.

(xiv) (RS)-α-cyano-4-fluoro-3-phenoxybenzyl (RS)-2-[2-(1,1-dimethylethyl)pyrimidin-5-yl]butanoate (compound No. 121) using method 1.

¹H NMR (CDCl₃): 0.8–1.0 (3H,2t); 1.4 (9H,s); 1.8, 2.1 (2H,m); 3.5 (1H,t); 6.3 (1H,2s); 6.9–7.4 (8H,m); 8.6 (2H,2s).

GLC Retention Time: 11.26, 11.49 minutes.

Physical data consistent with 66:34 mixture of 2 diastereoisomers.

(xv) 2,3,5,6-tetrafluoro-4-(methoxymethyl)benzyl (RS)-2-(2-chloropyrimidin-5-yl)-3-methylbutanoate (compound No. 118) using method 4.

¹H NMR (CDCl₃): 0.78 (3H,t); 1.02 (3H,t); 2.32 (1H,m);3.20 (1H,d); 3.36 (3H,s); 4.56 (2H, broad s); 5.22 (2H,q); 8.56 (2H,s).

Molecular ion: 420

4-(Prop-2-en-1-yl)-2,3,5,6-tetrafluorobenzyl (RS)-2-2-methylpyrimidin-5-yl]-3-methylbutanoate (compound No. 119).

¹H NMR (CDCl₃): 0.75 (d,3H); 1.00 (d,3H); 2.35 (m,1H); 2.75 (s,3H); 3.20 (d,1H); 3.50 (m,2H); 5.05–5.30 (m,4H); 5.85–5.95 (m,1H); 8.60 (s,2H)

GLC Retention Time: 6.75 minutes (95%).

(xvi) 4-(Prop-2-en-1-yl)-2,3,5,6-tetrafluorobenzyl (RS)-2-[2-methylpyrimidin-5-yl]-3-methylbutanoate (compound No. 119).

¹H NMR (CDCl₃): 0.75 (d,3H); 1.00 (d,3H); 2.35 (m,1H); 2.75 (s,3H); 3.20 (d,1H); 3.50 (m, 2H); 5.05–5.30 (m,4H); 5.85–5.95 (m,1H); 8.60 (s,2H)

GLC Retention Time: 6.75 minutes (95%).

(xvii) 4-(methoxymethyl)-b 2,3,5,6-tetrafluoroenzyl (RS)-2-(2-methylpyrimidin-5-yl)-3-methylbutanoate (compound No. 214) by method 1.

¹H NMR (CDCl₃): 0.75 (d,3H); 1.05 (d,3H); 2.35 (m,1H); 2.75 (s,3H); 3.20 (d,1H); 3.40 (s,3H); 4.60 (s,2H); 5.2–5.3 (dd, 2H); 8.60 (s,2H)

GLC Retention Time: 7.04 minutes (xviii) 2,3,5,6-tetrafluoro-4-(methoxymethyl)benzyl (RS)-2-[2-(1-methylcyclopropyl)pyrimidin-5-yl]-3,3-dimethylbutanoate (compound No. 139) using method 2.

400 MHz ¹H NMR (CDCl₃): 0.90 (2H,m); 0.95 (9H,s); 1.35 (2H,m); 1.55 (3H,s); 3.35 (1H,s); 3.40 (3H,s); 4.60 (3H,s); 5.17 (1H,d); 5.25 (1H,d); 8.60 (2H,s)

GLC Retention Time: 10.38 minutes (xix) (RS)-1-(6-phenoxypyrid-2-yl)ethyl (RS)-2-[2-(1-methylcyclopropyl)pyrimidin-5-yl]-3,3-dimethylbutanoate (compound No. 203) using method 2.

400 MHz ¹H NMR (CDCl₃): 0.90 (2H,m); 0.95 and 1.00 (9H,s); 1.35 (2H,m); 1.45 and 1.55 (3H,d); 1.58 (3H,s); 3.38 and 3.42 (s,1H); 5.8 (1H,m); 6.67–7.65 (8H,complex); 8.62 and 8.64 (2H,s)

GLC Retention Time: 12.31 and 12.58 minutes (mixture of diastereoisomers)

(xx) RS-1-(6-phenoxypyrid-2-yl)ethyl (RS)-2-(2-methylpyrimidin-5-yl)-3,3-dimethylbutanoate using method 2 (compound No. 205)

400 MHz ¹H NMR (CDCl₃): 0.9 and 1.0 (9H,s); 1.45 and 1.55 (3H,d); 2.72 and 2.74 (3H,s); 3.40 and 3.43 (1H,s); 5.8 (1H,m); 6.65–7.7 (8H,m); 8.68 and 8.70 (2H,s)

GLC Retention Time: 11.08 and 11.28 minutes (mixture of diastereoisomers)

(xxi) 2,3,5,6-tetrafluoro-4-(methoxymethyl)benzyl (RS)-2-[2-1,1-dimethylpropyl)pyrimidin-5-yl]-3,3-dimethylbutanoate using method 2 (compound No. 61).

400 MHz ¹H NMR (CDCl₃): 0.7 (3H,t); 0.99 (9H,s); 1.37 (6H,s); 1.80 (2H,q); 3.38 (1H,s); 3.40 (3H,s); 4.6 (2H,s); 5.15 (1H,d); 5.3 (1H,d); 8.70 (2H,s)

GLC Retention Time: 10.21 minutes (xxii) (RS)-1-(6-phenoxypyrid-2-yl)ethyl (RS)-2-[2-(1,1-dimethylpropyl)pyrimidin-5-yl]-3,3-dimethylbutanoate using method 2 (compound No. 57)

400 MHz ¹H NMR (CDCl₃): 0.6 (3H,m); 1.85 and 1.95 (9H;s); 1.30 and 1.32 (6H,s); 1.4 and 1.5 (3H,d); 1.75 (2H,m); 3.35 and 3.38 (1H,s); 5.75 (1H,m); 6.6–7.6 (8H,m); 8.65 (2H,s)

GLC Retention Time: 12.13 and 12.34 minutes (mixture of diastereoisomers)

(xxiii) 2,3,5,6-tetrafluoro-4-(methoxymethyl)benzyl (RS)-2-[2-(1-methylethyl)-pyrimidin-5-yl]-3,3-dimethylbutanoate using method 1 (compound No. 131)

250 MHz ¹H NMR (CDCl₃): 0.95 (9H,s); 1.25 (6H,d); 3.15 (1H,septet); 3.35 (3H,s); 3.36 (1H,s); 4.50 (2H,s); 5.15 (1H,d); 5.25 (1H,d); 8.65 (2H,s)

(xxiv) 4-methyl-2-thiomethyl-3,5-difluorobenzyl (RS)-2-[2-(1,1-dimethylethyl)pyrimidin-5-yl]-3,3-dimethylbutanoate using method 2 (compound No. 182)

¹H NMR (CDCl₃): 1.00 (s,9H); 1.40 (s,9H); 2.20 (m,3H); 2.30 (s,3H); 3.42 (s,1H); 5.24–5.36 (bq, 2H); 6.88 (bd, 1H); 8.72 (s,2H)

GLC Retention Time: 10.51 minutes (xxv) 4-(EZ-3-chloroprop-2-en-1-yl)-2,3,5,6-tetrafluorobenzyl (RS)-2-[(1,1-dimethylethyl)pyrimidin-5-yl]-3,3-dimethylbutanoate (E:Z ratio 1:2) using Method 2 (compound No. 14)

¹H NMR (CDCl₃): 1.00 (s,9H); 1.40 (s,9H); 3.40 (s,1H); 3.50, 3.70 (2d broad, 2H); 5.12–5.30 (bq, 2H); 5.80–6.20 (m,2H); 8.72 (s,2H)

GLC Retention Time: 10.66 minutes (E isomer) 10.73 minutes (Z isomer)

(xxvi) 4-[3-(triethylsilyl)prop-1-yl]-2,3,5,6-tetrafluorobenzyl (RS)-2-[2-(1,1-dimethylethyl)pyrimidin-5-yl]-3,3-dimethylbutanoate using method 2 (compound No. 218)

¹H NMR (CDCl₃): 0.42–0.60 (m,8H); 0.88–0.95 (m,9H); 1.00 (s,9H); 1.40 (s,9H); 1.55–1.65 (m,2H); 2.70–2.80 (m,2H); 3.40 (s,1H); 5.12–5.30 (bq, 2H); 8.72 (s,2H)

GLC Retention Time: 12.84 minutes (xxvii) 4-(Prop-2-ylideneaminoxymethyl)-2,3,5,6-tetrafluorobenzyl (RS)-2-[2-(1,1-dimethylethyl)-pyrimidin-5-yl]-3,3-dimethylbutanoate using method 2 (compound No. 178)

¹H NMR (CDCl₃): 1.00 (s,9H); 1.41 (s,9H); 1.82 (d,6H); 3.40 (s,1H); 5.14 (bs, 2H); 5.14–5.32 (bq, 2H); 8.72 (s,2H)

GLC Retention Time: 10.68 minutes (xxviii) 4-[(1,1-dimethylethyl)thio]methyl-2,3,5,6-tetrafluorobenzyl (RS)-2-[2-(1,1-dimethylethyl)-pyrimidin-5-yl]-3,3-dimethylbutanoate using method 2 (compound No. 175)

$^1$H NMR (CDCl$_3$): 1.00 (s,9H); 1.40 (s,9H); 1.42 (s,9H); 3.40 (s,1H); 3.80 (bs, 2H); 5.12–5.30 (bq, 2H); 8.72 (s,2H)

GLC Retention Time: 11.54 minutes (xxix): 4-[(1-methylethyl)thiomethyl-2,3,5,6-tetrafluorobenzyl (RS)-2-[2-(1,1-dimethylethyl)pyrimidin-5-yl]-3,3-dimethylbutanoate using method 2 (compound No. 174)

$^1$H NMR (CDCl$_3$): 1.00 (s,9H); 1.30 (d,6H); 1.40 (s,9H); 2.82–2.96 (m,1H); 3.40 (s,1H) 3.80 (bs, 2H); 5.12–5.30 (bq, 2H); 8.72 (s,2H)

GLC Retention Time: 11.23 minutes (xxx) 4-[(piperidin-1-yl)methyl]-2,3,5,6-tetrafluorobenzyl (RS)-2-(2-(1,1-dimethylethyl)pyrimidin-5-yl)-3,3-dimethylbutanoate using method 2 (compound No. 177)

$^1$H NMR (CDCl$_3$): 1.00 (s,9H); 1.32–1.44 (m,2H); 1.41 (s,9H); 1.52–1.64 (bs, 4H); 2.38–2.52 (bs, 4H); 3.40 (s,1H); 3.72–3.80 (bs, 2H); 5.12–5.32 (bq, 2H); 8.72 (s,2H)

GLC Retention Time: 11.84 minutes (xxxi) 4-[(2,2-dichlorocyclopropyl)methyl]-2,3,5,6-tetrafluorobenzyl (RS)-2-[2-(1,1-dimethylethyl)-pyrimidin-5-yl]-3,3-dimethylbutanoate using method 2 (compound No. 216)

$^1$NMR (CDCl$_3$): 1.00 (s,9H); 1.22–1.34 (m,1H); 1.41 (s,9H); 1.60–1.66 (m,1H) 1.80–2.00 (m,1H); 2.72–2.84 (m,1H); 3.20–3.27 (m,1H); 3.40 (s,1H); 5.12–5.30 (bq, 2H) 8.72 (s,2H)

GLC Retention Time: 11.75 minutes (xxxii) 4-(cyclopropylmethyl)-2,3,5,6-tetrafluorobenzyl (RS)-2-[2-(1,1-dimethylethyl)pyrimidin-5-yl]-3,3-dimethylbutanoate using method 2 (compound No. 179)

$^1$H NMR (CDCl$_3$): 0.25–0.3 (m,2H); 0.45–0.55 (m,2H); 1.00 (s,9H); 1.15–1.25 (m,1H); 1.40 (s,9H); 2.6–2.7 (bd, 2H); 3.40 (s,1H); 5.15–5.30 (bq, 2H) 8.75 (s, 2H)

GLC Retention Time: 10.27 minutes (xxxiii) 4-(N,N-dimethylaminomethyl)-b 2,3,5,6-tetrafluorobenzyl (RS)-2-[2-(1,1-dimethylethyl)-pyrimidin-5-yl]-3,3-dimethylbutanoate using method 2 (compound No. 176)

$^1$H NMR (CDCl$_3$): 1.00 (s,9H); 1.08 (bt,6H); 1.41 (s,9H); 2.54 (bq, 4H); 3.40 (s,1H); 3.76 (bs, 2H); 5.10–5.30 (bq, 2H); 8.72 (s,2H)

GLC Retention Time: 10.81 minutes (xxxiv) (RS)-1-[6-(4-chlorophenoxy)pyrid-2-yl]ethyl (RS)-2-[2-(1,1-dimethylethyl)pyrimidin-5-yl]-3,3-dimethylbutanoate using method 2 (compound No. 181)

$^1$H NMR (CDCl$_3$): 0.94 (s); 1.01 (s); 1.42 (bs); 1.44–1.5 (m); 3.42 (bs); 5.72–5.84 (m); 6.68–7.72 (m); 8.72 (bs). Integration consistent with 3:2 mixture of diastereoisomers GLC Retention Time: 12.47 minutes (60%) 12.72 minutes (40%)

(xxxv) 2,3,4,5,6-pentafluorobenzyl (RS)-2-[2-(1,1-dimethylethyl)pyrimidin-5-yl]-3,3-dimethylbutanoate using method 2 (compound No. 30)

$^1$H NMR (CDCl$_3$): 1.00 (s,9H); 1.40 (s,9H); 3.45 (s,1H); 5.20 (q,2H); 8.70 (s,2H)

GLC Retention Time: 7.62 minutes (xxxvi) 4-(prop-2-en-1-yl)-2,3,5,6-tetrafluorobenzyl (RS)-2-[2-(1,1-dimethylethyl)pyrimidin-5-yl]-3,3-dimethylbutanoate using method 2 (compound No. 5)

$^1$H NMR (CDCl$_3$): 1.00 (s,9H); 1.40 (s,9H); 3.40 (s,1H); 5.10 (m,2H); 5.20 (q,2H); 5.90 (m,1H); 8.70 (s,2H)

GLC Retention Time: 9.42 minutes (xxxvii) 2-methyl-3,4,5,6-tetrafluorobenzyl (RS)-2-[2-(1,1-dimethylethyl)pyrimidin-5-yl]-3,3-dimethylbutanoate using method 2 (compound No. 219)

$^1$H NMR (CDCl$_3$): 1.00 (s,9H); 1.40 (s,9H); 2.20 (s,3H); 3.35 (s,1H); 5.15 (q,2H); 8.70 (s,2H)

GLC Retention Time: 8.46 minutes (xxxviii) 4-(trimethylsilyl)-2,3,5,6-tetrafluorobenzyl (RS)-2-[2-(1,1-dimethylethyl)pyrimidin-5-yl]-3,3-dimethylbutanoate using method 2 (compound No. 22)

$^1$H NMR (CDCl$_3$): 0.41 (s,9H); 1.00 (s,9H); 1.40 (s,9H); 3.40 (s,H); 5.12–5.30 (bq, 2H); 8.72 (s,2H)

GLC Retention Time: 9.81 minutes (xxxix) 4-(n-propyl)-2,3,5,6-tetrafluorobenzyl (RS)-2-[2-(1,1-dimethylethyl)pyrimidin-5-yl]-3,3-dimethylbutanoate using method 2 (compound No. 168)

$^1$H NMR (CDCl$_3$): 0.95–1.00 (m,3H); 1.00 (s,9H); 1.40 (s,9H); 1.60–1.70 (m,2H); 2.70–2.75 (bt, 2H); 3.40 (s,1H); 5.12–5.30 (bq, 2H); 8.72 (s,2H)

GLC Retention Time: 9.50 minutes (93%)

(xl) 4-benzyl-2,3,5,6-tetrafluorobenzyl (RS)-2-[2-(1,1-dimethylethyl)pyrimidin-5-yl]-3,3-dimethylbutanoate using method 2 (compound No. 17)

$^1$H NMR (CDCl$_3$): 1.00 (s,9H); 1.40 (s,9H); 3.40 (s,1H); 4.06 (bs, 2H); 5.12–5.30 (bq, 2H); 7.20–7.36 (m,5H); 8.72 (s,2H)

GLC Retention Time: 11.93 minutes (xli) 4-(methylthio)-2,3,5,6-tetrafluorobenzyl (RS)-2-[2-(1,1-dimethylethyl)pyrimidin-5-yl]-3,3-dimethylbutanoate using method 2 (compound No. 183)

$^1$H NMR (CDCl$_3$): 1.00 (s,9H); 1.40 (s,9H); 2.55 (s,3H); 3.40 (s,1H); 5.20 (q,2H); 8.70 (s,2H)

GLC Retention Time: 9.53 minutes (xlii) 4-fluoro-3-phenoxybenzyl (RS)-2-[2-(1,1-dimethylpropyl)pyrimidin-5-yl]-3,3-dimethylbutanoate using method 3 (compound No. 68)

270 MHz $^1$H NMR (CDCl$_3$): 0.7 (3H,t); 0.95 (9H,s); 1.37 (6H,s); 1.8 (2H,q); 3.4 (1H,s); 5.0 (1H,d); 5.1 (1H,d); 7.0–7.4 (8H,m); 8.72 (2H,s)

GLC Retention Time: 12.57 minutes (xliii) 4-fluoro-3-phenoxybenzyl (RS)-2-[2-(1-methylethyl)pyrimidin-5-yl]-3,3-dimethylbutanoate using method 3 (compound No. 197)

250 MHz $^1$H NMR (CDCl$_3$): 0.95 (9H,s); 1.35 (6H,d); 3.20 (1H,septet); 3.35 (1H,s); 4.95 (1H,d); 5.10 (1H,d); 6.9–7.5 (8H,m); 8.7 (2H,s)

Melting Point: 85° C.

(xliv) (RS)-1-(6-phenoxypyridin-2-yl)ethyl (RS)-2-[2-(1-methylethyl)pyrimidin-5-yl]-3,3-dimethylbutanoate using method 3 (compound No. 74)

250 MHz $^1$H NMR (CDCl$_3$): 0.92 and 1.00 (9H,s); 1.35 and 1.36 (6H,d); 1.45 and 1.55 (3H,d); 3.25 (1H,m); 3.45 and 3.47 (s,1H); 5.80 (1H,m); 6.6–7.7 (8H,m); 8.69 and 8.70 (2H, s)

Mixture of Diastereoisomers (xlv) 4-fluoro-3-phenoxybenzyl (RS)-2-[2-(N,N-dimethylamino)pyrimidin-5-yl]-3,3-dimethylbutanoate using method 3 (compound No. 200)

250 MHz ¹H NMR (CDCl₃): 0.95 (9H,s); 3.18 (6H,s); 3.20 (1H,s); 4.95 (1H,d); 5.05 (1H,d); 6.9–7.4 (8H,m); 8.30 (2H,s)

(xlvi) 2,3,5,6-tetrafluoro-4-(methoxymethyl)benzyl (RS)-2-[2-(N,N-dimethylaminopyrimidin-5-yl]-3,3-dimethylbutanoate using method 3 (compound No. 199)

250 MHz ¹H NMR (CDCl₃): 0.95 (9H,s); 3.15 (6H,s); 3.20 (1H,s); 3.40 (3H,s); 4.58 (2H,s); 5.15 (1H,d); 5.25 (1H,d); 8.30 (2H,d)

(xlvii) (RS)-1-(6-phenoxypyrid-2-yl)ethyl (RS)-2-[2-(N,N-dimethylamino)pyrimidin-5-yl]-3,3-dimethylbutanoate using method 3 (compound No. 198)

250 MHz ¹H NMR (CDCl₃): 0.95 and 1.00 (s,9H); 1.45 and 1.55 (3H,d); 3.18 and 3.19 (6H,s); 3.27 and 3.29 (1H,s); 5.75 (1H,m); 6.6–7.7 (8H,m); 8.35 and 8.37 (2H,s)

As a Mixture of Diastereoisomers (xlviii) 4-fluoro-3-phenoxybenzyl (RS)-2-(2-cyclopropylpyrimidin-5-yl)-3,3-dimethylbutanoate using method 3 (compound No. 201)

90 MHz ¹H NMR (CDCl₃): 0.95 (9H,s), 1.10 (4H,m); 2.22 (1H,m); 3.35 (1H,s); 4.90 (1H,d); 5.1 (1H,d); 6.80–7.40 (8H,m); 8.50 (2H,s)

Melting Point: 92°–93° C.

(xlix) 2,3,5,6-tetrafluoro-4-(methoxymethyl)benzyl (RS)-2-(2-cyclopropylpyrimidin-5-yl)-3,3-dimethylbutanoate using method 3 (compound No. 135)

250 MHz ¹H NMR (CDCl₃): 0.95 (9H,s); 1.10 (4H,m); 2.23 (1H,m); 3.35 (1H,s); 3.40 (3H,s); 4.58 (2H,s); 5.15 (1H,d); 5.25 (1H,d); 8.58 (2H,s)

(l) RS-1-(6-phenoxypyrid-2-yl)ethyl (RS)-2-(2-cyclopropylpyrimidin-5-yl)-3,3-dimethylbutanoate using method 3 (compound No. 78)

250 MHz ¹H NMR (CDCl₃): 0.95 and 1.00 (9H,s); 1.20 (4H,m); 1.45 and 1.55 (3H,d); 2.25 (1H,m); 3.35 and 3.39 (1H,s); 5.80 (1H,m); 6.65–7.70 (8H,m); 8.59 and 8.60 (1H,s)

(li) 3,5,6-trifluoro-2-methoxy-4-(methoxymethyl)benzyl (RS)-2-[2-(1-methylethyl)pyrimidin-5-yl]-3,3-dimethylbutanoate using method 3 (compound No. 76)

250 MHz ¹H NMR (CDCl₃): 1.00 (9H,s); 1.25 (6H,d); 3.20 (1H, septet); 3.35 (1H,s); 3.40 (3H,s); 3.90 (3H,s); 4.45 (2H,s); 5.15 (1H,d); 5.25 (1H,d); 8.72 (2H,s)

(lii) 2,3,5,6-tetrafluoro-4-(methoxymethyl)benzyl (RS)-2-(2-phenylpyrimidin-5-yl)-3,3-dimethylbutanoate using method 3 (compound No. 161)

250 MHz ¹H NMR (CDCl₃): 1.05 (9H,s); 3.40 (3H,s); 3.45 (1H,s); 4.68 (2H,s); 5.20 (1H,d); 5.30 (1H,d); 7.5 (3H,m); 8.55 (2H,m); 8.85 (2H,s)

(liii) (RS)-1-(6-phenoxypyrid-2-yl)ethyl (RS)-2-(2-phenylpyrimidin-5-yl)-3,3-dimethylbutanoate using method 3 (compound No. 82)

250 MHz ¹H NMR (CDCl₃): 0.95 and 1.05 (9H,s); 1.48 and 1.55 (3H,d); 3.48 and 3.52 (1H,s); 5.85 (1H,m); 6.60–7.80 (11H,m); 8.45 (2H,m); 8.83 and 8.87 (2H,s)

(liv) 4-methoxymethyl-2,3,5,6-tetrafluorobenzyl (RS)-2-[2-(1,1-dimethylethyl)-pyrimidin-5-yl]-3,3-dimethylpentanoate using method 3 (compound No. 210)

¹H NMR (CDCl₃): 0.90 (t,3H); 0.9 (s,3H); 1.00 (s,3H); 1.2–1.4 (m,2H); 1.40 (s,9H); 3.40 (s,3H); 3.50 (s,1H); 4.60 (broad s, 2H); 5.1–5.3 (m,2H); 8.7 (s,2H)

GLC Retention Time: 10.43 minutes (lv) 4-(methylthiomethyl)-2,3,5,6-tetrafluorobenzyl (RS)-2-[2-(1,1-dimethylethyl)pyrimidin-5-yl]-3,3-dimethylbutanoate using method 3 (compound No. 169)

¹H NMR (CDCl₃): 1.00 (s,9H); 1.40 (s,9H); 2.12 (s,3H); 3.40 (s,1H); 3.77 (bs, 2H); 5.12–5.30 (bq, 2H); 8.72 (s,2H)

GLC Retention Time: 10.91 minutes (lvi) 4-[(prop-2-yn-1-yl)thiomethyl]-2,3,5,6-tetrafluorobenzyl (RS)-2-[2-(1,1-dimethylethyl)pyrimidin-5-yl]-3,3-dimethylbenzoate using method 3 (compound No. 220)

¹H NMR (CDCl₃): 1.00 (s,9H); 1.40 (s,9H); 2.25 (m,1H); 3.27 (d,2H); 3.40 (s,1H); 3.97 (bs, 2H); 5.12–5.30 (bq, 2H); 8.72 (s,2H)

GLC Retention Time: 11.57 minutes (lvii) 3-(4-chlorophenoxy)benzyl (RS)-2-[2-(1,1-dimethylethyl)pyrimidin-5-yl]-3,3-dimethylbutanoate using method 3 (compound No. 180)

¹H NMR (CDCl₃): 1.00 (s,9H); 1.40 (s,9H); 3.40 (s,1H); 5.10 (q,2H); 6.95 (t,3H); 7.05 (d,1H); 7.30 (q,4H); 8.75 (s,2H)

GLC Retention Time: 13.04 minutes (lviii) (RS)-1-cyano-1-(3-phenoxyphenyl)methyl (RS)-2-[2-(1,1-dimethylethyl)pyrimidin-5-yl]-3,3-dimethylbutanoate using method 3 (compound No. 2)

¹H NMR (CDCl₃): 0.92 (s); 1.06 (s); 1.40 (m); 3.46 (m); 6.28 (s); 6.40 (s); 6.96–7.44 (m); 8.72 (m); (Consistent with mixture of diastereoisomers)

GLC Retention Time: 12.51 minutes and 12.78 minutes (lix) 4-(ethoxycarbonyl)-2,3,5,6-tetrafluorobenzyl (RS)-2-[2-(1,1-dimethylethyl)pyrimidin-5-yl]-3,3-dimethylbutanoate using method 3 (compound No. 170)

¹H NMR (CDCl₃): 1.00 (s,9H); 1.36–1.44 (m,12H); 3.40 (s,1H); 4.40–4.48 (q,2H); 5.12–5.30 (bq, 2H); 8.72 (s,2H)

GLC Retention Time: 10.28 minutes (lx) 4-[(prop-2-yl)oxycarbonyl]-2,3,5,6-tetrafluorobenzyl (RS)-2-[2-(1,1-dimethylethyl)pyrimidin-5-yl]-3,3-dimethylbutanoate using method 3 (compound No. 171)

¹H NMR (CDCl₃): 1.00 (s,9H); 1.36 (d, 6H); 1.42 (s,9H); 3.40 (s,1H); 5.12–5.40 (m,3H); 8.72 (s,2H)

GLC Retention Time: 10.45 minutes (lxi) 4-[(4-chlorobenzyloxy)methyl]-2,3,5,6-tetrafluorobenyl (RS)-2-[2-(1,1-dimethylethyl)pyrimidin-5-yl]-3,3-dimethylbutanoate using method 3 (compound No. 163)

¹H NMR (CDCl₃): 1.00 (s,9H); 1.40 (s,9H); 3.40 (s,1H); 4.56 (s,2H); 4.66 (bs, 2H); 5.12–5.30 (bq, 2H); 7.26–7.36 (m,4H); 8.72 (s,2H)

GLC Retention Time: 14.53 minutes (lxii) (6-phenoxypyrid-2-yl)methyl (RS)-2-[2-(1,1-dimethylethyl)pyrimidin-5-yl]-3,3-dimethylbutanoate using method 3 (compound No. 9)

¹H NMR (CDCl₃): 1.00 (s,9H); 1.40 (s,9H); 3.45 (s,1H) 5.05–5.15 (q, 2H); 6.75–7.70 (m,8H); 8.75 (s,2H)

GLC Retention Time: 12.00 minutes (lxiii) (RS)-1-(6-phenoxypyrid-2-yl)ethyl (RS)-2-[2-(1,1-dimethylethyl)pyrimidin-5-yl]-3,3-dimethylbutanoate using method 3 (compound No. 11)

¹H NMR (CDCl₃): 0.95 (s); 1.00 (s); 1.40 (m); 1.45 (m); 1.55 (m); 3.45 (m); 5.80 (m); 6.65–7.70 (m); 8.75 (m) Consistent with 1:1 mixture of diastereoisomers GLC Retention Time: 11.57 minutes, 11.79 minutes (lxiv) 2-chloro-6-fluorobenzyl (RS)-2-[2-(1,1-dimethylethyl)pyrimidin-5-yl]-3,3-dimethylbutanoate using method 3 (compound No. 26)

¹H NMR (CDCl₃): 1.00 (s,9H); 1.40 (s,9H); 3.40 (s,1H); 5.20–5.40 (q,2H); 7.00–7.36 (m,3H); 8.72 (s,2H)
GLC Retention Time: 9.26 minutes (lxv) N-3,4,5,6-tetrahydrophthalimidomethyl (RS)-2-[2-(1,1-dimethylethyl)pyrimidin-5-yl]-3,3-dimethylbutanoate using method 3 (compound No. 6)

¹H NMR (CDCl₃): 1.00 (s,9H); 1.40 (s,9H); 1.80 (m,4H); 2.36 (m,4H); 3.72 (s,1H); 5.44–5.60 (q,2H); 8.72 (s,2H)
GLC Retention Time: 11.60 minutes (lxvi) 2-methyl-3-phenylbenzyl (RS)-2-[2-(1,1-dimethylethyl)pyrimidin-5-yl]-3,3-dimethylbutanoate using method 3 (compound No. 3)

¹H NMR (CDCl₃): 1.00 (s,9H); 1.40 (s,9H); 2.16 (s,3H); 3.40 (s,1H); 5.12–5.24 (q,2H); 7.20–7.44 (m,8H); 8.72 (s,2H)
GLC Retention Time: 12.19 minutes (lxvii) 3-phenoxybenzyl (RS)-2-[2-(1,1-dimethylethyl)pyrimidin-5-yl]-3,3-dimethylbutanoate using method 3 (compound No. 1)

¹H NMR (CDCl₃): 1.00 (s,9H); 1.40 (s,9H); 3.40 (s,1H); 5.00–5.16 (q,2H); 6.92–7.40 (m,9H); 8.72 (s,2H)
GLC Retention Time: 12.07 minutes (lxviii) 4-fluoro-3-phenoxybenzyl (RS)-2-[2-(1,1-dimethylethyl)pyrimidin-5-yl]-3,3-dimethylbutanoate using method 3 (compound No. 25)

¹H NMR (CDCl₃): 1.00 (s,9H); 1.40 (s,9H); 3.40 (s,1H); 4.92–5.12 (bq,2H); 6.92–7.36 (m,8H); 8.72 (s,2H)
GLC Retention Time: 11.97 minutes (lxix) 3-benzyl-4-fluorobenzyl (RS)-2-[2-(1,1-dimethylethyl)pyrimidin-5-yl]-3,3-dimethylbutanoate using method 3 (compound No. 18)

¹H NMR (CDCl₃): 1.00 (s,9H); 1.40 (s,9H); 3.35 (s,1H); 4.00 (bs, 2H); 4.95–5.10 (bq, 2H); 6.95–7.30 (m,8H); 8.72 (s,2H)
GLC Retention Time: 12.00 minutes (lxx) 4-(methoxymethyl)-2,3,5,6-tetrafluorobenzyl (RS)-2-[2-(1,1-dimethylethyl)pyrimidin-5-yl]pent-4-enoate using method 4 (compound No. 212)

¹H NMR (CDCl₃): 1.40 (s,9H); 2.55 (m,1H); 2.85 (m,1H); 3.40 (s,3H); 3.65 (t,1H); 4.60 (broad s, 2H); 5.0–5.1 (m,2H); 5.20–5.30 (q, 2H); 5.6–5.75 (m,1H); 8.60 (s,2H)
GLC Retention Time: 9.53 minutes (lxxi) 4-(methoxymethyl)-2,3,5,6-tetrafluorobenzyl (RS)-2-[2-(1,1-dimethylethyl)pyrimidin-5-yl]-3,3,3-trifluoropropionate using method 4 (compound No. 213)

¹H NMR (CDCl₃): 1.40 (s,9H); 3.40 (s,3H); 4.30 (q,1H); 4.60 (s,2H); 5.35 (s,2H); 8.75 (s,2H)
GLC Retention Time: 7.86 minutes (lxxii) (RS)-1-(6-phenoxypyrid-2-yl)-2,2,2-trifluoroethyl (RS)-2-[2-(1,1-dimethylethyl)pyrimidin-5-yl]-3,3-dimethylbutanoate, using method 5 (compound No. 32)

¹H NMR (CDCl₃): 0.95 (s); 1.00 (s); 1.40 (bs); 3.55 (2s); 6.05 (m); 6.8–7.0 (m); 7.05–7.25 (m); 7.35–7.45 (m); 7.60–7.65 (m); 7.70–7.80 (m); 8.70 (s); 8.75 (s) Integration consistent with 3:2 mixture of diastereoisomers
GLC Retention Time: 10.73 minutes, 11.07 minutes (lxxiii) 4-(methoxymethyl)-2,3,5,6-tetrafluorobenzyl (RS)-2-[2-(1,1-dimethylethyl)pyrimidin-5-yl]-3,3-dimethylpent-4-enoate using method 3 (compound No. 211)

¹H NMR (CDCl₃): 1.05 (2s,6H); 1.4 (s,9H); 3.40 (s,3H); 3.45 (s,1H); 4.60 (bs,2H); 4.85 (d,1H); 5.05 (d,1H); 5.1–5.3 (dd,2H); 5.85–5.95 (dd,1H); 8.70 (s,2H)
GLC Retention Time: 10.0 minutes (lxxiv) 4-(hydroxymethyl)-2,3,5,6-tetrafluorobenzyl (RS)-2-[2-(1,1-dimethylethyl)pyrimidin-5-yl]-3,3-dimethylbutanoate using method 3 (compound No. 164). The preparation of 4-halomethyl-2,3,5,6-tetrafluorobenzenemethanols is described in UK Patent No. 2153819

¹H NMR (CDCl₃): 1.00 (s,9H); 1.40 (s,9H); 2.16 (bs,1H); 3.40 (s,1H); 4.84 (bs,2H); 5.12–5.30 (bq,2H); 8.72 (s,2H)
GLC Retention Time: 10.04 minutes (lxxv) 2,3,5-trifluoro-6-ethoxy-4-(ethoxymethyl)benzyl (RS)-2-[2-(1,1-dimethylethyl)pyrimidin-5-yl]-3,3-dimethylbutanoate, using method 3 (compound No. 188)

250 MHz ¹H NMR (CDCl₃): 0.99 (9H,s); 1.22 (3H,t); 1.26 (3H,t); 1.40 (9H,s); 3.36 (1H,s); 3.58 (2H,t); 4.08 (2H,m); 4.58 (2H,t); 5.15 (1H,dd); 5.24 (1H,dd); 8.72 (2H,s)

(lxxvi) 2,3,5-trifluoro-6-ethoxy-4-(phenoxymethyl)benzyl (RS)-2-[2-(1,1-dimethylethyl)pyrimidin-5-yl]-3,3-dimethylbutanoate using method 3 (compound No. 194)

250 MHz ¹H NMR (CDCl₃): 1.00 (9H,s); 1.25 (3H,t); 1.42 (9H,s); 3.36 (1H,s); 4.10 (2H,m); 5.12 (2H,s); 5.15 (1H,d); 5.25 (1H,d); 7.0 (2H,m); 7.40 (3H,m); 8.70 (2H,s)

(lxxvii) 2,3,6-trifluoro-5-methoxy-4-(methoxymethyl)-benzyl (RS)-2-[2-(1,1-dimethylethyl)pyrimidin-5-yl]-3,3-dimethylbutanoate, using method 3 (compound 217)

250 MHz ¹H NMR (CDCl₃): 0.93 (9H,s); 1.34 (9H,s); 3.33 (3H+1H,s); 3.85 (3H,d); 4.45 (2H,d); 5.05 (1H,d); 5.20 (1H,d); 8.65 (2H,s)

(lxxviii) 2,3,5-trifluoro-6-methoxy-4-[(1-methyl)ethoxy]methylbenzyl (RS)-2-[2-(1,1-dimethylethyl)pyrimidin-5-yl]-3,3-dimethylbutanoate, using method 3 (compound No. 190)

250 MHz ¹H NMR (CDCl₃): 1.00 (9H,s); 1.21 (6H,d); 1.40 (9H,s); 3.36 (1H,s); 3.71 (1H, septet); 3.86 (3H,d); 4.59 (3H,t); 5.15 (1H,dd); 5.25 (1H,dd); 8.73 (2H,s)

(lxxix) 2,3,5-trifluoro-6-methoxy-4-(phenoxymethyl)benzyl (RS)-2-[2-(1,1-dimethylethyl)pyrimidin-5-yl]-3,3-dimethylbutanoate, using method 3 (compound No. 193)

250 MHz ¹H NMR (CDCl₃): 0.82 (9H,s); 1.22 (9H,s); 3.18 (1H,s); 3.68 (3H,d); 4.94 (2H,t); 4.96 (1H,dd); 5.04 (1H,dd); 6.80 (3H,m); 7.1 (2H,m); 8.54 (2H,s)

(lxxx) 2,3,5-trifluoro-6-ethoxy-4-(methoxymethyl)benzyl (RS)-2-[2-(1,1-dimethylethyl)pyrimidin-5-yl]-3,3-dimethylbutanoate, using method 3 (compound No. 185)

250 MHz ¹H NMR (CDCl₃): 1.00 (9H,s); 1.26 (3H,t); 1.40 (9H,s); 3.35 (1H,s); 3.40 (3H,s); 4.08 (2H,m); 4.57 (2H,t); 5.15 (1H,dd); 5.25 (1H,dd); 8.72 (2H,s)

(lxxxi) 2,3,5,6-tetrafluoro-4-(phenoxymethyl)benzyl (RS)-2-[2-(1,1-dimethylethyl)pyrimidin-5-yl]-3,3-dimethylbutanoate, using method 3 (compound No. 192)

250 MHz ¹H NMR (CDCl₃): 0.8 (9H,s); 1.22 (9H,s); 3.2 (1H,s); 4.97 (2H,s); 5.00 (1H,d); 5.10 (1H,d); 6.80 (3H,m); 7.10 (2H,m); 8.55 (2H,s)

(lxxxii) 2,3,5-trifluoro-6-methoxy-4-(ethoxymethyl)benzyl (RS)-2-[2-(1,1-dimethylethyl)pyrimidin-5-yl]-3,3-dimethylbutanoate, using method 3 (compound No. 187)

250 MHz ¹H NMR (CDCl₃): 1.00 (9H,s); 1.25 (3H,t); 1.43 (9H,s); 3.38 (1H,s); 3.58 (2H,q); 3.87 (3H,d); 4.60 (2H,t); 5.15 (1H,dd); 5.25 (1H,dd); 8.75 (2H,s)

(lxxiii) 2,3,5,6-tetrafluoro-4-(ethoxymethyl)benzyl (RS)-2-[2-(1,1-dimethylethyl)pyrimidin-5-yl]-3,3-dimethylbutanoate, using method 3 (compound No. 186)

250 MHz $^1$H NMR (CDCl$_3$): 1.00 (9H,s); 1.25 (3H,t); 1.45 (9H,s); 3.40 (1H,s); 3.60 (2H,q); 4.65 (2H,s); 5.20 (1H,d); 5.30 (1H,d); 8.73 (2H,s)

(lxxxiv) 2,3,5,6-tetrafluoro-4-[(1-methyl)ethoxy]methylbenzyl (RS)-2-[2-(1,1-dimethylethyl)pyrimidin-5-yl]-3,3-dimethylbutanoate using method 3 (compound No. 189)

250 MHz $^1$H NMR (CDCl$_3$): 0.98 (9H,s); 1.22 (6H,d); 1.41 (9H,s); 3.38 (1H,s); 3.73 (1H, septet); 4.6 (2H,s); 5.16 (1H,d); 5.28 (1H,d); 8.70 (2H,s)

(lxxxv) 2,3,5,6-tetrafluoro-4-(methoxymethyl)benzyl (RS)-2-[2-(1-methylcyclohexyl)pyrimidin-5-yl]-3,3-dimethylbutanoate, using method 2 (compound No. 207)

270 MHz $^1$H NMR (CDCl$_3$): 1.00 (9H,s); 1.25 (3H,s); 1.20–1.60 (8H,m); 2.34 (2H,m); 3.40 (1H,s); 3.42 (3H,s); 4.58 (2H,s); 5.17 (1H,d); 5.30 (1H,d); and 9.73 (2H,d)

(lxxxvi) 2,3,5,6-tetrafluoro-4-(methoxymethyl)benzyl (RS)-2-[2-(trifluoromethyl)pyrimidin-5-yl]-3,3-dimethylbutanoate, using method 4 (compound No. 41)

270 MHz $^1$H NMR (CDCl$_3$): 1.00 (9H,s); 3.40 (3H,s); 3.53 (1H,s); 4.58 (2H,s); 5.20 (1H,d); 5.30 (1H,d); 8.96 (2H,s)

(lxxxvii) 2,3,5,6-tetrafluorobenzyl-4-(methoxymethyl)-benzyl (RS)-2-[2-(2-chlorophenyl)pyrimidin-5-yl]-3,3-dimethylbutanoate using method 3 (compound No. 208)

250 MHz $^1$H NMR (CDCl$_3$): 1.05 (9H,s); 3.40 (3H,s); 3.50 (1H,s); 4.60 (2H,s); 5.23 (1H,d); 5.33 (1H,d); 7.35 (2H,m); 7.50 (1H,m); 7.75 (1H,m); 8.93 (2H,s)

(lxxxviii) 4-fluoro-3-phenoxybenzyl (RS)-2-[2-(2-chlorophenyl)pyrimidin-5-yl]-3,3-dimethylbutanoate using method 3 (compound No. 209)

250 MHz $^1$H NMR (CDCl$_3$): 1.00 (9H,s); 3.48 (1H,s); 4.47 (1H,d); 5.13 (1H,d); 6.90–7.40 (10H,m); 7.50 (1H,m); 7.75 (1H,m); 8.90 (2H,s)

(lxxxix) 4-(prop-2-en-1-yl)-2,3,5,6-tetrafluorobenzyl (RS)-2-[2-phenylpyrimidin-5-yl)-3-methylbutanoate using method 4 (compound No 113)

250 MHz $^1$H NMR (CDCl$_3$): 0.80 (d,3H); 1.06 (d,3H); 2.40 (m,1H); 3.26 (d,1H ); 3.46 (m,2H); 5.18 (m,4H); 5.88 (m,1H); 7.48 (m,3H); 8.44 (m,2H); 8.78 (s,2H);

GLC Retention Time: 12.24 minutes (xc) 4-fluoro-3-phenoxybenzyl (RS)-2-[2-(1-methylcyclopropyl)pyrimidin-5-yl]-3,3-dimethylbutanoate using method 3 (compound No 204)

270 MHz $^1$H NMR (CDCl$_3$): 0.93 (2H,m); 0.95 (9H,s); 1.35; (2H,m); 1.56 (3H,s); 3.3 (1H,s); 4.95 (1H,d); 5.50 (1H,d); 6.8–7.4 (8H,m); 8.61 (2H,s)

GLC Retention Time: 12.65 Minutes

EXAMPLE 21

This Example illustrates the preparation of 2,3,5,6-tetrafluoro-4-(acetyloxymethyl)benzyl (RS)-2-[2-(1,1-dimethylethyl)pyrimidin-5-yl]-3,3-dimethylbutanoate (compound No 166) from 2,3,5,6-tetrafluoro-4-(hydroxymethyl)benzyl (RS)-2-[2-(1,1-dimethylethyl)pyrimidin-5-yl]-3,3-dimethylbutanoate (prepared according to example 20 (lxxxiv).

4-(hydroxymethyl)-2,3,5,6-tetrafluorobenzyl 2-[2-(1,1-dimethylethyl)pyrimidin-5-yl]-3,3-dimethylbutanoate (0.066 g) was dissolved in dry dichloromethane (2 cm$^3$) and cooled to 0° C. To the stirred solution was added triethylamine (dry, 0.03 cm$^3$), followed by acetyl chloride (0.016 cm$^3$). The reaction was kept at 0° C. for 1 hour, then diluted with dichloromethane and a small volume of water. The organic fraction was separated, dried and evaporated under reduced pressure to yield an oil which was fractionated by thick layer chromatography (silica gel, eluted with dichloromethane/ethyl acetate 20:1 by volume; extracted with ethyl acetate) to give the title compound as a colourles oil (0.06 g).

$^1$H NMR (CDCl$_3$): 1.00 (s,9H); 1.40 (s,9H); 2.10 (s,3H); 3.40 (s,1H); 5.12–5.30 (m,4H); 8.72 (s,2H).

GLC Retention Time: 10.56 minutes

EXAMPLE 22

The following compounds were prepared according to the method described in Example 21.

(i) 4-[(2,2-dimethylpropionyl)oxymethyl]-2,3,5,6-tetrafluorobenzyl (RS)-2-[2-(1,1-dimethylethyl)-pyrimidin-5-yl]-3,3-dimethylbutanoate (compound No 172)

$^1$H NMR (CDCl$_3$): 1.00 (s,9H); 1.20 (s,9H); 1.40 (s,9H); 3.40 (s,1H); 5.12–5.30 (m,4H); 8.72 (s,2H).

GLC Retention Time: 11.12 minutes (ii) 4-[(2-methylpropionyl)oxymethyl]-2,3,5,6-tetrafluorobenzyl (RS)-2-[2-(1,1-dimethylethyl)pyrimidin-5-yl]-3,3-dimethylbutanoate (compound No 173)

$^1$H NMR (CDCl$_3$): 1.00 (s,9H); 1.16 (d,6H); 1.40 (s,9H); 2.50–2.60 (m,1H); 3.40 (s,1H); 5.12–5.30 (bq,2H); 5.20 (bs,2H); 8.72 (s,2H)

GLC Retention Time: 11.04 minutes (iii) 4-chloromethyl-2,3,5,6-tetrafluorobenzyl (RS)-2-[2-(1,1-dimethylethyl)pyrimidin-5-yl]-3,3-dimethylbutanoate (compound No 167) prepared using methanesulphonyl chloride.

$^1$H NMR (CDCl$_3$): 1.00 (s,9H); 1.40 (s,9H); 3.40 (s,1H); 4.68 (bs,2H); 5.12–5.30 (bq,2H); 8.72 (s,2H).

GLC Retention Time: 9.91 minutes

EXAMPLE 23

This Example illustrates the preparation of 4-(methoxymethyl)-2,3,5,6-tetrafluorobenzyl (RS)-2-[2-(1,1-dimethylethyl)pyrimidin-5-yl]-3,3-dimethylbutanthioate (compound No 195) from 4-hydroxymethyl-2,3,5,6-tetrafluorobenzyl (RS)-2-[2-(1,1-dimethylethyl)pyrimidin-5-yl]-3,3-dimethylbutanthioate.

4-hydroxymethyl-2,3,5,6-tetrafluorobenzyl 2-[2-(1,1-dimethylethyl)pyrimidin-5-yl]-3,3-dimethylbutanthioate (0.064 g) was dissolved in dichloromethane (2 cm$^3$) and mixed with an aqueous solution of sodium hydroxide (2 cm$^3$, 50% w/v) and tetrabutylammonium hydrogen sulphate (0.002 g; phase transfer catalyst). To the rapidly stirred mixture at the ambient temperature was added methyl iodide (0.2 cm$^3$). The reaction mixture was stirred for 24 hours, stored for a further 60 hours and then diluted with dichloromethane. The organic fraction was separated, washed with water and dried over anhydrous magnesium sulphate. The solvent was evaporated under reduced pressure to yield an oil (0.073 g) which was fractionated by eluting through a bed of silica gel with dichloromethane/ethyl acetate (20:1 by volume). The required product was obtained as an oil (0.053 g).

$^1$H NMR (CDCl$_3$): 1.00 (s,9H); 1.40 (s,9H); 3.40 (s,3H); 3.48 (s,1H); 4.12–4.30 (bq,2H); 4.52 (bs,2H); 8.72 (s,2H)

GLC Retention Time: 10.82 minutes

EXAMPLE 24

The following compounds were prepared according to the method described in Example 23.

(i) 4-[(1,1-dimethylethyl)oxycarbonylmethoxymethyl]-2,3,5,6-tetrafluorobenzyl (RS)-2-[2-(1,1-dimethylethyl]pyrimidin-5-yl]-3,3-dimethylbutanoate (compound No 165) using 1,1-dimethylethyl 2-bromacetate $^1$H NMR (CDCl$_3$): 1.00 (s,9H); 1.40 (s,9H); 1.50 (s,9H); 3.40 (s,1H); 4.02 (s,2H); 4.76 (bs,2H); 5.12–5.30 (bq,2H); 8.72 (s,2H)

GLC Retention Time: 12.32 minutes

EXAMPLE 25

This Example describes the stages in the preparation of (+)-4-(methoxymethyl)-2,3,5,6-tetrafluorobenzyl 2-[2-(1,1-dimethylethyl)pyrimidin-5-yl]-3,3-dimethylbutanoate (compound No 15-resolved form).

Stage 1: Resolution of (RS)-2-[2-(1,1-dimethylethyl)-pyrimidin-5-yl]-3,3-dimethylbutanoic acid (+)-2-[2-(1,1-dimethylethyl)pyrimidin-5-yl]-3,3-dimethylbutanoic acid (0.234 g) was mixed with (−)-α-methylbenzylamine (available from Sigma Chemical Company, 0.071 g) in ethanol (5 cm$^3$), and the mixture warmed until all of the reagents had dissolved. The solution was stored at −15° C. to −10° C. for 5 days to produce a solid precipitate which was filtered from the chilled solution. The solid was washed with a small volume of cold ethanol and recrystallised once from ethanol to give strands of the (−)-α-methylbenzylamine salt on filtration. The solid was suspended in toluene/2M hydrochloric acid and warmed with stirring for 3 hours. The aqueous layer was separated, extracted with dichloromethane and the toluene and dichloromethane fractions combined. Evaporation of the solvents under reduced pressure gave a colourless solid (0.42 g). Analysis by HPLC cyclobond column eluted with acetonitrile/water/formic acid in ratio 40/60/0.1 by volume] indicated the produce to have a >85% enantiomeric excess of (−)-2-[2-(1,1-dimethylethyl)-pyrimidin-5-yl]-3,3-dimethylbutanoic acid.

Melting Point: 224°–227.4° C.

Optical Rotation: [α]$_D$ 1.0°±0.1° (chloroform)

A similar procedure using (+)-α-methylbenzylamine gave (+)-2-[2-(1,1-dimethylethyl)pyrimidin-5-yl]-3,3-dimethylbutanoic acid in >85% enantiomeric excess.

Melting Point: 222.3°–223.7° C.

Optical Rotation: [α]$_D$ 0.9°±0.1° (chloroform)

Either enantiomer may be re-converted to the racemic acid by heating at temperatures from 150°–230° C. in the presence of an acid catalyst such as para-toluenesulphonic acid or concentrated sulphuric acid, either with no solvent, or in solution in a high-boiling solvent such as 1,4-dichlorobenzene, typically for 0.5 to 20 hours. This process provides a method of racemisation and recycling of the (+)-enantiomer, which has been found to yield esters having reduced insecticidal and acaricidal activity, thereby allowing a greater overall yield of the (−)-enantiomer which on esterification, gives esters in the more active enantiomeric or diastereoisomeric form.

Stage 2: The resolved acids obtained in stage 1 were esterified using method 3 (described in Example 19) to produce the (+) and (−) isomers of 4-(methoxymethyl)-2,3,5,6-tetrafluorobenzyl 2-[2-(1,1-dimethylethyl)pyrimidin-5-yl]-3,3-dimethylbutanoate (compound No 15—resolved forms).

The (+)-isomer (shown to be present in greater than 95% enantiomeric excess) exhibited an optical rotation ([α]$_D$) of 39.6° chloroform (25.3° in methanol).

The (−)-isomer (>85% enantiomeric excess) exhibited an optical rotation ([α]$_D$ of −38.5°±0.1° in chloroform (−24.5° in methanol).

Biological screening has shown that the (−)-enantiomer exhibits substantially greater insecticidal and acaricidal activity than the (+)-enantiomer.

EXAMPLE 26

This Example illustrates the stages in the preparation of 2,3,5,6-tetrafluoro-4-(methoxymethyl)benzyl (RS)-2-[2-(1,1-dimethylethyl)pyrimidin-5-yl]-3-methylbut-3-enoate (compound No 202)

Stage 1: Preparation of ethyl 2-[2-(1,1-dimethylethyl)-pyrimidin-5-yl]-3-methylbut-2-enoate A 2.5 molar solution of n-butyl lithium in hexanes (5.5 cm$^3$) was added in portions to a suspension of isopropyltriphenylphosphonium iodide (6 g) in dry diethyl ether, whilst the temperature was maintained between −10° and −20° C. After stirring for 1 hour at this temperature, a solution of ethyl 2-[2-(1,1-dimethylethyl)pyrimidin-5-yl]-2-oxo-acetate (3 g) in dry diethyl ether (15 cm$^3$) was added in portions. The stirred reaction mixture was allowed to warm to the ambient temperature, and allowed to stir for 16 hours. The reaction mixture was poured into water and extracted into ethyl acetate. The combined organic extracts were washed, dried over anhydrous magnesium sulphate, and concentrated by removal of the solvent under reduced pressure to give a dark brown oil, which was subjected to chromotography on silica gel, using hexane containing 10% ethyl acetate (by volume), as eluent to give ethyl 2-[2-(1,1-dimethylethyl)pyrimidin-5-yl]-3-methylbut-2-enoate (0.4 g) as a clear oil.

270 MHz $^1$H NMR (CDCl$_3$): 1.23 (3H,t); 1.43 (9H,s); 1.75 (3H,s); 2.25 (3H,s); 4.15 (2H,q); 8.50 (2H,s)

Stage 2: Preparation of 2-[2-(1,1-dimethylethyl)pyrimidin-5-yl]-3-methylbut-2-enoic acid.

A solution of sodium hydroxide 0.24 g) and ethyl 2-[2-(1,1-dimethylethyl)pyrimidin-5-yl]-3-methylbut-2-enoate (0.4 g) in isopropanol (10 cm$^3$) and water (2 cm$^3$) was heated to the reflux temperature for a period of 3 hours. After cooling to the ambient temperature the crude reaction mixture was concentrated by evaporation of the solvent under reduced pressure, and the residue was dissolved in water, and extracted with ethyl acetate. The aqueous portion was acidified with dilute hydrochloric acid, and extracted with ethyl acetate. The combined organic extracts were washed with water, dried over anhydrous magnesium sulphate and concentrated by evaporation of the solvent under reduced pressure to give 2-[2-(1,1-dimethylethyl)pyrimidin-5-yl]-3-methylbut-2-enoic acid, containing a small amount of 2-[2-(1,1-dimethylethyl)pyrimidin-5-yl]-3-methylbut-3-enoic acid. The crude produce was used without further purification.

270 MHz $^1$H NMR (CDCl$_3$): 1.42 (9H,s); 1.80 (3H,s); 2.33 (3H,s); 8.55 (2H,s)

Stage 3: Preparation of 2,3,5,6-tetrafluoro-4-(methoxymethyl)benzyl 2-[2-(1,1-dimethylethyl)pyrimidin-5-yl]-3-methylbut-2-enoate 2-[2-(1,1-dimethylethyl)pyrimidin-5-yl]-3-methylbut-2-enoic acid (0.25 g) was reacted with 2,3,5,6-tetrafluoro-4-(methoxymethyl)benzyl alcohol (0.24 g) in the presence of 1-ethyl-3-(3-dimethylaminopropyl)carbodiimide, according to the procedure given in method 2 in Example 19.

The crude produce was subjected to chromatography on silica gel using dichloromethane containing 20% by volume ethyl acetate as eluent, to give 2,3,5,6-tetrafluoro-4-(methoxymethyl)benzyl 2-[2-(1,1-dimethylethyl)pyrimidin-5-yl]-3-methylbut-2-enoate (0.18 g).

270 MHz $^1$H NMR (CDCl$_3$): 1.40 (9H,s); 1.75 (3H,s); 2.25 (3H,s); 3.39 (3H,s); 4.55 (2H,s); 5.25 (2H,s); 8.45 (2H,s)

The product was shown by NMR to contain 30% of 2,3,5,6-tetrafluoro-4-(methoxymethyl)benzyl 2-[2-(1,1-dimethylethyl)pyrimidin-5-yl]-3-methylbut-3-enoate.

Stage 4: Preparation of 2,3,5,6-tetrafluoro-4-(methoxymethyl)benzyl (RS)-2-[2-(1,1-dimethylethyl)pyrimidin-5-yl]-3-methylbut-3-enoate (compound No 202).

A 1 molar solution of lithium hexamethyldisilazide (0.125 cm$^3$) in dry tetrahydrofuran was added to a stirred solution of 2,3,5,6-tetrafluoro-4-(methoxymethyl)benzyl 2-[2-(1,1-dimethylethyl)pyrimidin-5-yl]-3-methylbut-2-enoate (0.05 g) in dry tetrahydrofuran (1 cm$^3$) whilst the reaction temperature was maintained at $-78°$ C. After 30 minutes, acetic acid (0.01 g) was added in one portion, and the stirred reaction mixture was allowed to warm to the ambient temperature, and quenched with water. Extraction into ethyl acetate, and concentration by removal of the solvent under reduced pressure gave 2,3,5,6-tetrafluoro-4-(methoxymethyl)benzyl (RS)-2-[2-(1,1-dimethylethyl)pyrimidin-5-yl]-3-methylbut-3-enoate (0.05 g).

270 MHz $^1$H NMR (CDCl$_3$): 1.38 (9H,s); 1.60 (3H broad s); 3.40 (3H,s); 4.25 (1H,s); 4.56 (2H,s,); 4.90 (1H,s); 5.05 (1H,s); 5.27 (1H,d); 5.33 (1H,d); 8.63 (2H,s)

The product was shown by NMR spectroscopic analysis to contain 20% of 2,3,5,6-tetrafluoro-4-(methoxymethyl)benzyl (RS)-2-[2-(1,1-dimethylethyl)pyrimidin-5-yl)-3-methylbut-2-enoate.

EXAMPLE 27

This Example illustrates the stages in the preparation of Z-4-(3-chloroprop-2-en-1-yl)-2,3,5,6-tetrafluorobenzyl alcohol.

(i) Preparation of Z-1-chloro-3-iodoprop-1-ene. A solution of Z-1,3-dichloropropene (4.05 g) and potassium iodide (6.0 g) in dry acetone (75 cm$^3$) was heated to the reflux temperature for a period of two hours. After cooling to the ambient temperature (ca. 25° C.), the reaction mixture was poured into aqueous sodium thiosulphate solution, and then extracted with diethyl ether. The organic layer was washed with water, and brine, dried, and the solvent evaporated under reduced pressure to give Z-1-chloro-3-iodoprop-1-ene as an orange oil (2.4 g). This material was immediately carried through to the next stage.

GLC retention time: 1.04 minutes (ii) Preparation of 2-[Z-4-(3-chloroprop-2-en-1-yl)-2,3,5,6-tetrafluorobenzyloxy]tetrahydropyran.

n-Butyl lithium (2.5M in hexane, 3 cm$^3$) was added portionwise to a solution of 2-[4-bromo-2,3,5,6-tetrafluorobenzyloxy]-tetrahydropyran (1.7 g) in dry tetrahydrofuran (10 cm$^3$) under an atmosphere of dry nitrogen, whilst the reaction temperature was maintained at $-70°$ C. After 30 minutes, copper (I) bromide—dimethyl sulphide complex (1.54 g) was added in one portion and the reaction temperature allowed to warm to 0° C., for a period of 15 minutes. After cooling to $-70°$ C., a solution of Z-1-chloro-3-iodoprop-1-ene (2.03 g) in dry tetrahydrofuran (3 cm$^3$) was added portionwise, and the reaction mixture stirred for a further hour at $-70°$ C. After warming to the ambient temperature, (ca. 25° C.), aqueous ammonium chloride was added to the reaction mixture, which was then extracted with ethyl acetate. After drying, the solvent was evaporated under reduced pressure to give an orange oil. The residue was then subjected to medium pressure column chromaatography on a silica gel column using a Gilson apparatus, eluting with petroleum ether (boiling range 40°-60° C.) containing diethyl ether (5% by volume) to give 2-[4-(3-chloroprop-2-en-1-yl)-2,3,5,6-tetrafluorobenzyloxy]-tetrahydropyran, as a mixture consisting predominantly of the Z isomer.

$^1$H NMR (CDCl$_3$): 1.5–1.8 (m,6H); 3.5 (m,1H); 3.65 (d,2H); 3.90 (m,1H); 4.60 (d,1H); 4.8 (m,2H); 5.8 q,1H); 6.15 (m,1H)

GLC retention time: 5.98 minutes (iii) Preparation of Z-4-(3-chloroprop-2-en-1-yl)-2,3,5,6-tetrafluorobenzyl alcohol.

The tetrahydropyranyl ether prepared in stage (ii) was dissolved in methanol (30 cm$^3$), and to the stirred solution was added a catalytic amount of concentrated hydrochloric acid. After stirring for two hours, the reaction mixture was diluted with water, and extracted with ethyl acetate. The organic layer was washed and dried, and the solvent evaporated under reduced pressure to give Z-4-(3-chloroprop-2-en-1-yl)-2,3,5,6-tetrafluorobenzyl alcohol (0.6 g) as a colourless oil, which solidified on standing.

$^1$H NMR (CDCl$_3$): 3.65 (d,2H); 4.8 (s,2H); 5.85 (q,1H); 6.2 (m,1H)

Infra red (liquid film): 3640, 1490, 1300, 1250 and 1040 cm$^{-1}$

GLC retention time: 3.08 minutes.

EXAMPLE 28

This Example illustrates the stages in the preparation of 4-trimethylsilyl-2,3,5,6-tetrafluorobenzyl alcohol.

(i) Preparation of 2-[4-trimethylsilyl-2,3,5,6-tetrafluorobenzyloxy]-tetrahydropyran.

A solution of n-butyl lithium (1.5M in hexane, 2.9 cm$^3$) was added portionwise to a solution of 4-bromo-2,3,5,6-tetrafluorobenzyloxy]-tetrahydropyran (1.5 g) in dry tetrahydrofuran (43 cm$^3$) under an atmosphere of dry nitrogen, whilst the reaction temperature was maintained at $-70°$ C. As the last portion of base was added, an intense purple colour developed. Chlorotrimethylsilane (1.6 cm$^3$, dried over alumina) was added portionwise, leading immediately to a dissipation of the purple colouration. The reaction mixture was then poured into water, and extracted into ethyl acetate. The organic layer was washed with water and brine, dried, and the solvent evaporated under reduced pressure to give 2-[4-trimethylsilyl-2,3,5,6-tetrafluorobenzyloxyl]-tetrahydropyran. This crude material (94% pure by Gas Chromatography) was carried immediately to the next stage, without further purification.

90 MHz $^1$H NMR (CDCl$_3$): 0.5 (s,9H); 1.4–2.1 (m,6H); 3.4–4.4 (m,2H); 4.5–5.2 (m,3H)

GLC retention time: 5.07 minutes.

(ii) Preparation of 4-trimethylsilyl-2,3,5,6-tetrafluorobenzyl alcohol.

The crude tetrahydropyranyl ether prepared in Stage (i) was dissolved in methanol (20 cm$^3$), and to the stirred solution was added concentrated hydrochloric acid (3 drops). After stirring for 16 hours at the ambient temperature (ca. 25° C.), the reaction mixture was poured into ethyl acetate, washed with water and brine, and dried. Evaporation of the solvent under reduced pressure gave a yellow oil which was subjected to column chromatography on silica gel using petroleum ether (boiling range 40°–60° C.) containing diethyl ether (10% gradually increased to 40% by volume) as eluent to give 4-trimethylsilyl-2,3,5,6-tetrafluorobenzyl alcohol (0.79 g).

90 MHz $^1$H NMR (CDCl$_3$): 0.4 (s,9H); 1.0 (t,1H); 4.8 (m,2H)

GLC Retention Time: 2.24 minutes

EXAMPLE 29

This Example illustrates the stages in the preparation of 3,5-difluoro-4-methyl-2-methylthiobenzyl alcohol.

Stage 1: Preparation of methyl 2,3,5-trifluoro-6-methylthio-4-(methoxymethyl)benzoate.

A solution of methanethiol (0.7 g) in methanol (10 cm$^3$) was added to a stirred solution of sodium methoxide [by dissolving sodium metal (0.23 g) in methanol 10 cm$^3$], at the ambient temperature over 15 minutes.

The above solution was added dropwise to a stirred solution of methyl 4-(methoxymethyl)-2,3,5,6-tetrafluorobenzoate and stirring continued for a further 2 hours at the ambient temperature and stood overnight.

The reaction mixture was poured into water and was extracted into diethyl ether. The organic extracts were washed with water and brine, and dried over MgSO$_4$. Removal of the solvent by evaporation under reduced pressure yielded an oil (2.0 g) which was purified by HPLC (Gilson), eluting with hexane/diethyl ether (9:1 by volume). The first product eluted was identified as methyl 4-(methoxymethyl)-2-methylthio-3,5,6-trifluorobenzoate (1.5 g).

$^1$H NMR (CDCl$_3$): 4.48 (t,2H); 3.90 (s,3H); 3.32 (s,3H); 2.36 (s,3H)

Stage 2: Preparation of 3,5-difluoro-4-methyl-2-methylthiobenzyl alcohol.

Methyl 4-(methoxymethyl)-2-methylthio-3,5,6-trifluorobenzoate (0.48 g) was dissolved in dry tetrahydrofuran (2 cm$^3$) under a nitrogen atmosphere at room temperature. To the stirred solution was added dropwise a solution of lithium aluminum hydride (1.0 cm$^3$ of a 1.0 molar solution in THF). The mixture was stirred for 0.5 hour when stored for 18 hours. The solution was treated with 2 molar hydrochloric acid and extracted with dichloromethane (twice), dried (anhydrous magnesium sulphate), and evaporated under reduced pressure to give a pale yellow liquid (0.37 g). The liquid was fractionated by eluting through a bed of silica gel with dichloromethane/ethyl acetate (50:1 by volume) to yield the title product (0.04 g).

GLC Retention Time: 2.78 minutes
Molecular Ion: 204

EXAMPLE 30

This Example illustrates the preparation of 4-[(1,1-dimethylethyl)thiomethyl[-2,3,5,6-tetrafluorobenzyl alcohol.

2-Methyl-2-propanethiol (0.207 cm$^3$) was slowly added to a stirred mixture of sodium hydride (0.091 g, 56–60% dispersion in oil) in dry N,N-dimethylformamide (2 cm$^3$) under a nitrogen atmosphere at room temperature. After 1 hour the solution was added slowly to a stirred solution of 4-bromomethyl-2,3,5,6-tetrafluorobenzyl alcohol (0.496 g, preparation described in UK Patent Application No 2153819) in dry N,N-dimethylformamide (2 cm$^3$) under a nitrogen atmosphere at room temperature. On complete addition the reaction mixture was heated to 60° C. for 2 hours. After cooling, the reaction mixture was treated with water (10 cm$^3$) and extracted with diethyl ether (2×15 cm$^3$). The combined organic fractions were dried with anhydrous magnesium sulphate and evaporated under reduced pressure to give an orange oil. The oil was fractionated by eluting through a bed of silica gel (Merck 7729) with dichloromethane/ethyl acetate (100:2 by volume) to give the title product as a yellow gum (0.233 g).

GLC Retention Time: 4.57 minutes
Infra Red (liquid film): 3366, 2964, 1657, 1488, 1366, 1288, 1168, 1092, 1019, 942, 848, 670 cm$^{-1}$

EXAMPLE 31

4-[(1-Methylethyl)thiomethyl]-2,3,5,6-tetrafluorobenzyl alcohol was prepared according to the method described in Example 30, using 2 -propanethiol.

GLC Retention Time: 4.19 minutes
Infra Red (paraffin mull): 3417, 2921, 1462, 1376, 1290, 1016, 943 cm$^{-1}$

EXAMPLE 32

This Example illustrates the preparation of 4-methylthio-2,3,5,6-tetrafluorobenzyl alcohol.

4-Bromomethyl-2,3,5,6-tetrafluorobenzyl alcohol [10.0 g prepared according to the method described in UK Patent Application No 2153819] was dissolved in toluene (dry, 250 cm$^3$) and treated with thiourea (2.8 g). The reaction mixture was stirred and heated at the reflux temperature for 2 hours, further thiourea (1.5 g) was added and the mixture was heated for a further 1 hour. The reaction mixture was allowed to cool to the ambient temperature and stored for 18 hours. The solid (ca 15 g) which had precipitated from solution was filtered, and washed with toluene and diethyl ether.

This solid material was added to industrial methylated spirits (100 cm$^3$) containing sodium hydroxide (4.5 g) and water (50 cm$^3$). The mixture was stirred and heated at the reflux temperature for 3 hours, then cooled and the solvent evaporated under reduced pressure. The residue was diluted with water and extracted with dichloromethane (2×100 cm$^3$). The basic, aqueous fraction was acidified with concentrated hydrochloric acid to pH 1 and the oil which separated was extracted with dichloromethane (2×120 cm$^3$). The organic fraction was washed with water and dried over anhydrous magnesium sulphate. The solvent was evaporated under reduced pressure to yield an oil (6.3 g) which solidified on standing.

Infra Red (Paraffin Mull): 3363, 2924, 2853, 1484, 1392, 1293, 1250, 1189, 1094, 1015, 935, 894, 663 cm$^{-1}$
GLC Retention Time: 2.80 minutes

EXAMPLE 33

This Example illustrates the preparation of 4-(methylthiomethyl)-2,3,5,6-tetrafluorobenzyl alcohol.

4-Thiomethyl-2,3,5,6-tetrafluorobenzyl alcohol (0.25 g prepared according to the method described in Example 32) was mixed with potassium carbonate (0.306 g) and acetone (5 cm$^3$) and heated to the reflux temperature. Methyl iodide (0.083 cm$^3$) was added rapidly to the refluxing mixture. After approximately 10 minutes the mixture was filtered, the filter cake was washed with acetone (5 cm$^3$) and the filtrates evaporated under reduced pressure to give an off-white solid. The solid was dissolved in dichloromethane (5 cm$^3$) and the insoluble material was filtered off. The filtrates were evaporated under reduced pressure to give the title product as an off-white solid (0.122 g).
GLC Retention Time: 3.50 minutes
$^1$H NMR (CDCl$_3$): 1.965 (t,1H); 2.10 (s,3H); 3.75 (s,2H); 4.82 (d,2H)

EXAMPLE 34

4-[(Prop-2-yn-1-yl)thiomethyl]-2,3,5,6-tetrafluorobenzyl alcohol was prepared according to the method described in Example 30 using prop-2-yn-1-thiol.
GLC Retention Time: 4.62 minutes
Infra Red (liquid film): 3300, 2955, 1703, 1657, 1484, 1426, 1288, 1229, 1112, 1031, 945, 932, 670, 642 cm$^{-1}$

EXAMPLE 35

4-[(Piperdin-1-yl)methyl]-2,3,5,6-tetrafluorobenzyl alcohol was prepared by a method analogous to that described in European Patent Application No 54360 for the 4-(N,N-diethylaminomethyl)-2,3,5,6-tetrafluorobenzyl alcohol.
Infra Red (liquid film): 3379, 2974, 1483, 1383, 1281, 1199, 1042, 915, 869, 782, 748, 637 cm$^{-1}$
GLC Retention Time: 3.71 minutes

EXAMPLE 36

This Example illustrates the preparation of ethyl 4-(iodomethyl)-2,3,5,6-tetrafluorobenzoate.
Stage 1: 4-(Methoxymethyl)-2,3,5,6-tetrafluorobenzoic acid [5.0 g prepared by a process similar to that described in European Patent Application No 54360] was dissolved in thionyl chloride (50 cm$^3$) and heated to the reflux temperature with stirring for 3 hours. The excess thionyl chloride was evaporated under reduced pressure to yield 4-(methoxymethyl)-2,3,5,6-tetrafluorobenzoyl chloride (ca 5 g) as a pale yellow liquid.
Infra Red (liquid film): 2938, 1770, 1654, 1487, 1388, 1301, 1193, 1091, 1049, 937, 846, 782, 731, 687 cm$^{-1}$
Stage 2: The acid chloride from stage 1 (1.00 g) was dissolved in dry ethanol (5 cm$^3$) and, when the initial exothermic reaction had subsided, the solution was stirred for a further 3 hours at the ambient temperature. The excess ethanol was evaporated under reduced pressure to yield ethyl 4-(methoxymethyl)-2,3,5,6-tetrafluorobenzoate (0.90 g) as a yellow oil.
GLC Retention Time: 2.82 minutes
The ester from stage 2 (0.9 g) was dissolved in dry acetonitrile (5 cm$^3$) and treated with sodium iodide (1.208 g) under a dry nitrogen atmosphere to give a yellow solution. To the stirred solution was added dropwise trimethylsilyl chloride (0.86 cm$^3$) and the mixture, which had become red-brown, was warmed to 35°–40° C., then allowed to slowly cool to the ambient temperature, and stirred for a further 18 hours. A sample was withdrawn and GLC analysis showed the reaction was ca 40% complete.
Further sodium iodide (1.02 g) and trimethylsilyl chloride (0.8 cm$^3$) was added and the reaction heated to reflux for 3 hours. The mixture was allowed to cool to the ambient temperature, and stored for 60 hours. The solution was poured into mixture of ethyl acetate and water, the organic fraction separated and washed with (i) aqueous sodium meta-bisulphite solution and (ii) saturated aqueous sodium chloride solution. The organic fraction was dried (anhydrous magnesium sulphate) and evaporated under reduced pressure to yield ethyl 4-(iodomethyl)-2,3,5,6-tetrafluoro-benzoate (1.07 g) as an orange-red oil.
Infra Red (liquid film): 2986, 1734, 1653, 1484, 1393, 1367, 1314, 1229, 1164, 1115, 1068, 1014, 974, 942, 866, 746 cm$^{-1}$
GLC Retention Time: 4.05 minutes

EXAMPLE 37

2-Methylethyl 4-(iodomethyl)-2,3,5,6-tetrafluorobenzoate was prepared by a process analogous to that described in Example 36.
Infra Red (liquid film): 2985, 1734, 1489, 1311, 1234, 1165, 1103, 1068, 975, 934, 828 cm$^{-1}$
GLC Retention Time: 4.31 minutes
(GLC Retention Time of intermediate 1-methylethyl 4-(methoxymethyl)-2,3,5,6-tetrafluorobenzoate: 3.10 minutes)

EXAMPLE 38

This Example illustrates the preparation of 2,3,5,6-tetrafluoro-4-[(1-methylethoxy)methyl]-benzyl alcohol.
Sodium (1.0 g) was added to dry isopropanol (200 cm$^3$), maintained at 40° C. under an atmosphere of dry nitrogen. After dissolution was complete, 4-(bromomethyl)-2,3,5,6-tetrafluorobenzyl alcohol (10.9 g) was added and the reaction was stirred for 16 hours, at the ambient temperature. The reaction mixture was poured into water, acidified with dilute aqueous hydrochloric acid, and extracted into ethyl acetate. The combined organic extracts were washed with water, dried over anhydrous magnesium sulphate, and concentrated by evaporation of the solvent under reduced pressure. The residue was combined with the product of a similar reaction and distilled under reduced pressure to give 2,3,5,6-tetrafluoro-4-[(1-methyl-ethoxy)methyl]-benzyl alcohol (0.8 g).
Boiling Point: 150°–170° C./0.2 mm Hg
60 MHz $^1$H NMR (CDCl$_3$): 1.20 (6H,d); 2.80 (1H,s); 3.70 (1H,septet); 4.55 (2H,s); 5.72 (2H,s)

EXAMPLE 39

This Example illustrates the preparation of 2,3,5-trifluoro-4-(ethoxymethyl)-6-methoxybenzyl alcohol.
A solution of sodium methoxide (generated from 0.13 g sodium) in dry methanol (20 cm$^3$) was added to a solution of 4-(ethoxymethyl)-2,3,5,6-tetrafluorobenzyl alcohol (1.2 g) in dry diglyme. The stirred reaction mixture was heated at 90° C. for a period of 4 hours, under an atmosphere of dry nitrogen, after which time a further portion of sodium methoxide (0.1 g) was added, and heating continued for a further 8 hours. After cooling to the ambient temperature the reaction mixture was poured into water, acidified with dilute aqueous hydrochloric acid, and extracted into ethyl acetate. The combined organic extracts were dried over anhydrous magnesium sulphate, and concentrated by evaporation of the solvent under reduced pressure. The brown residue was subjected to column chromatography on silica gel using hexane containing increasing amounts of diethyl ether (from 0% to 100%) by volume as eluent. The crude product thus obtained was gain subjected to chromatography on silica gel in a similar manner to give 2,3,5-trifluoro-4-(ethoxymethyl)-6-methoxybenzyl alcohol (0.3 g) as a pale yellow oil.
250 MHz $^1$H NMR (CDCl$_3$): 1.24 (3H,t); 2.10 (1H,broad s); 3.57 (2H,d); 4.00 (3H,d); 4.69 (2H,t); 4.75 (2H,d)

EXAMPLE 40

The following alcohols were prepared using the procedure illustrated in Example 39.

(i) 6-methoxy-4-([1-methylethoxy)methyl]-2,3,5-trifluorobenzyl alcohol.

60 MHz $^1$H NMR (CDCl$_3$): 1.15 (6H,d); 2.50 (1H, broad s); 3.60 (1H,septet); 3.85 (3H,s); 4.5 (2H,s); 4.6 (2H,m)

(ii) 6-methoxy-4-(phenoxymethyl)-2,3,5-trifluorobenzyl alcohol.

250 MHz $^1$H NMR (CDCl$_3$): 2.20 (1H,bs); 4.00 (3H,d); 4.78 (2H,d); 5.12 (2H,t); 7.0 (3H,m); 7.30 (2H,m)

(iii) 6-ethoxy-4-(methoxymethyl)-2,3,5-trifluorobenzyl alcohol.

90 MHz $^1$H NMR (CDCl$_3$): 1.40 (3H,t); 2.20 (1H, broad s); 3.40 (3H,s); 4.25 (2H,q); 4.58 (2H,t); 4.80 (2H,d)

(iv) 6-ethoxy-4-(phenoxymethyl)-2,3,5-trifluorobenzyl alcohol

250 MHz $^1$H NMR (CDCl$_3$): 2.10 (1H, broad s); 4.00 (3H,d); 4.75 (2H,d); 5.15 (2H,t); 7.00 (3H,m); 7.30 (2H,m)

(v) 2-ethoxy-4-(ethoxymethyl)-3,4,5-trifluorobenzyl alcohol

90 MHz $^1$H NMR (CDCl$_3$): 1.20 (3H,t); 1.40 (3H,t); 2.40 (1H,broad s); 3.55 (2H,q); 4.20 (2H,qd); 4.60 (2H,t); 4.75 (2H,d)

EXAMPLE 41

4-(methoxymethyl)-3-methoxy-2,5,6-trifluorobenzyl alcohol was isolated by HPLC as a by-product in the reaction between 4-(methoxymethyl)-2,3,5,6-tetrafluorobenzyl alcohol and sodium methoxide in methanol solution.

$^1$H NMR (CDCl$_3$): 2.10 (1H, broad s); 3.39 (3H,d); 3.95 (3H,d); 4.53 (2H,d); 4.80 (2H,t)

EXAMPLE 42

This example illustrates the stages in the preparation of 4-[(2,2-dichlorocyclopropyl)methyl]-2,3,5,6-tetrafluorobenzyl alcohol.

Stage 1

4-[prop-2-en-1-yl]-2,3,5,6-tetrafluorobenzyl tetrahydropyran-2-yl ether

4-[prop-2-en-1-yl]-2,3,5,6-tetrafluorobenzyl alcohol (6.15 g prepared according to the method described in European Patent Application No. 31199) was treated at the ambient temperature with 3,4-dihydro-2H-pyran (2.813 g) and para-toluenesulphonic acid (0.005 g) as catalyst.

The solution was stirred for 4 hours and residual dihydropyran removed by evaporation under reduced pressure. The tetrahydropyranyl ether was obtained as a colourless liquid residue, and was used without further purification.

Infra red (liquid film): 2945, 1639, 1486, 1350, 1275, 1202, 1184, 1120, 1028, 975, 906, 869, 817 cm$^{-1}$ GLC Retention Time: 4.94 minutes Stage 2: 4-[(2,2-dichlorocyclopropyl)methyl]-2,3,5,6-tetrafluorobenzyl tetrahydropyran-2-yl ether 4-[prop-2-en-1-yl]-2,3,5,6-tetrafluorobenzyl tetrahydropyran-2-yl ether (1.0 g) was treated with aqueous sodium hydroxide (10 cm$^3$; 40% w/v) and benzyltriethyl ammonium chloride (0.050 g; phase transfer catalyst).

To the rapidly stirred mixture was added chloroform (5 cm$^3$, ethanol free) and the reaction heated at the reflux temperature for 6 hours. The reaction mixture was cooled to the ambient temperature, diluted with dichloromethane (100 cm$^3$) and water (100 cm$^3$). The organic fraction was separated, washed with water (50 cm$^3$) and dried (anhydrous magnesium sulphate). The solvent was evaporated under reduced pressure to yield a brown oil which was fractionated by chromatography on silica gel eluted with n-hexane/ethyl acetate (25:1 by volume). The title product (0.44 g) was obtained as a colourless oil.

$^1$H NMR (CDCL): 1.2–1.35 (t,1H); 1.45–2.00 (m; 8H); 2.70–2.85 (m;1H); 3.15–3.30 (m;1H); 3.45–3.65 (m,1H) 3.85–4.0 (m,1H); 4.50–4.60 (m,1H); 4.70–4.90 (m,2H);

GLC Retention Time: 7.90 minutes

Stage 3: 4-[(2,2-dichlorocyclopropyl)methyl]-2,3,5,6-tetrafluorobenzyl alcohol.

4-[(2,2-dichlorocyclopropyl)methyl]-2,3,5,6-tetrafluorobenzyl tetrahydropyran-2-yl ether (0.240 g) was heated at the reflux temperature for 3 hours in a mixture of methanol (5 cm$^3$) and 2 M hydrochloric acid (1 cm$^3$). The solvent was evaporated under reduced pressure and water removed azeotropically from the sample by heating with toluene (2×10 cm$^3$). The title product (0.15 g) was obtained as an orange oil.

Infra Red (liquid film): 3364, 2977, 1658, 1485, 1382, 1277, 1221, 1100, 1017, 929, 903, 842, 759 cm$^{-1}$ GLC Retention Time: 4.94 minutes

EXAMPLE 43

This Example illustrates the stages in the preparation of 4-(cyclopropylmethyl)-2,3,5,6-tetrafluorobenzyl alcohol.

Stage 1: 4-(cyclopropylmethyl)-2,3,5,6-tetrafluorobenzyl-tetrahydropyran-2-yl ether.

4-[(2,2-dichlorocyclopropyl)methyl]-2,3,5,6-tetrafluorobenzyl tetrahydropyran-2-yl ether (0.43 g prepared according to stage 2 to Example 42) was treated with tri-n-butyltin hydride (2 cm$^3$) and aza-iso-butyronitrile (AIBN) (0.005 g, catalyst) under a nitrogen atmosphere. The stirred solution was heated to 110° C. for 5 hours, and further tri-n-butyltin hydride (b 1 cm$^3$) and catalyst (0.005 g) were added. The mixture was heated at 110° C. for a further 5 hours and more tri-n-butyltin hydride (1 cm$^3$) and catalyst (0.0005 g) added. Heating was then continued for a further 10 hours.

The reaction was cooled and the crude product isolated by pouring the solution onto a short column of silica gel and eluting with firstly n-hexane to remove the organotin residues and, secondly, n-hexane/ethyl acetate (25:1 by volume) to give two products, identified as 4-[(2-chlorocyclopropyl)methyl]-2,3,5,6-tetrafluorobenzyl tetrahydropyran-2-yl ether (Molecular ion 251, GLC Retention Times: 6.41 and 6.85 minutes, consistent with a mixture of isomers) and the required 4-(cyclopropylmethyl)-2,3,5,6-tetrafluorobenzyl tetrahydropyran-2-yl ether, obtained as a colourless liquid:

Infra Red (Liquid film): 2944, 1485, 1276, 1120, 1028 cm$^{-1}$

GLC Retention Time: 5.36 minutes

Stage 2: 4-cyclopropylmethyl-2,3,5,6-tetrafluorobenzyl alcohol.

Prepared from 4-(cyclopropylmethyl)-2,3,5,6-tetrafluorobenzyl tetrahydropyran-2-yl ether by the method described in Stage 3 of Example 42.

GLC Retention Time: 2.60 minutes

Infra Red (liquid film): 3352, 1484, 1307, 1276, 1138, 1020, 922, 860 cm$^{-1}$

EXAMPLE 44

This Example illustrates the preparation of 4-[(prop-2-ylidene)aminooxymethyl]-2,3,5,6-tetra-fluorobenzyl alcohol.

4-Bromomethyl-2,3,5,6-tetrafluorobenzyl alcohol (1.002 g, preparation described in UK Patent Application No. 2153819 A), acetone oxime (0.311 g), potassium t-butoxide (0.424 g) and dry dimethoxyethane (3 cm$^3$) were heated at the reflux temperature for 2 hours. The reaction was diluted with dichloromethane and water, the organic layer separated and the aqueous layer was extracted with further dichloromethane. The combined organic extracts were washed with water, dried over anhydrous magnesium sulphate and the solvent evaporated under reduced pressure to give the title product as an orange oil (0.835 g).

GLC Retention Time: 3.62 minutes

Infra Red (thin film): 3376, 2957, 1734, 1487, 1369, 1286, 1032, 892, 828 cm$^{-1}$

EXAMPLE 45

This Example illustrates the preparation of 4-[3-(triethylsily)propan-3-yl]-2,3,5,6-tetrafluorobenzyl alcohol.

Reference: Organometallics, Vol. 2, No. 6, p. 769-771 (1983)

4-[prop-2-en-1-yl]-2,3,5,6-tetrafluorobenzyl tetrahydropyran-2-yl ether prepared according to Stage 1 of Example 42) (1.04 g) was treated with triethylsilane (0.52 cm$^3$) containing 5% platinum on carbon (catalyst, 0.05 g). The mixture was placed in an ultrasound bath and sonicated for 3 hours. Further triethylsilane (0.1 cm$^3$) was added and the mixture was sonicated for a further 2 hours. The mixture was diluted with dichloromethane and the catalyst was filtered from the solution. The solvent was evaporated under reduced pressure to yield the silylated tetrahydropyranyl ether as an oil.

GLC Retention Time: 9.31 minutes

The oil was dissolved in methanol (5 cm$^3$) and dilute aqueous hydrochloric acid (1 cm$^3$, 2 molar) was added. The solution was kept at the ambient temperature for 18 hours, the organic solvents evaporated under reduced pressure and water removed azeotropically by heating with propan-2-ol (twice) to give the title product as an oil (1.01 g).

Infra Red (liquid film): 3335, 2953, 2876, 1486, 1416, 1298, 1274, 1090, 1017, 890, 731 cm$^{-1}$ GLC Retention Time: 6.56 minutes

EXAMPLE 46

This Example illustrates the stages in the preparation of 1-methylcyclopropanecarbonitrile.

(i) Preparation of 1-methylcyclopropanecarboxylic acid chloride. Oxalyl chloride (59.7 g) was added in portions to a stirred solution of 1-methylcyclopropanecarboxylic acid (40 g—commercially available from Aldrich Chemical Company Ltd) in chloroform (300 cm$^3$). The reaction mixture was then heated at the reflux temperature for 3 hours. After this time, the volatile components were removed by distillation at atmospheric pressure to leave a pale yellow liquid (49 g) which was shown by gas liquid chromatography to contain a small amount of unreacted oxalyl chloride. The product was used without further purification.

Infra red (liquid film): 2980, 1850, 1780, 1430, 1300, 1285, 1055, 1080, 930 cm$^{-1}$.

(ii) Preparation of 1-methylcyclopropanecarboxamide.

A solution of 1-methylcyclopropanecarboxylic acid choride (49 g) in chloroform (300 cm$^3$) was added gradually to a concentrated aqueous solution of ammonia (300 cm$^3$), previously cooled to 0° C. by external cooling. The reaction mixture warmed spontaneously to 20° C. and a white solid precipitate was formed; the precipitate was redissolved by further addition of chloroform. The organic layer was separated, dried over anhydrous magnesium sulphate and the solvent evaporated under reduced pressure. The residual solid was recrystallised from a mixture of chloroform and n-hexane to give 1-methylcyclopropanecarboxamide (17.6 g) as colourless crystal.

Melting point: 148° C.

Infra red (paraffin mull): 3390, 3200, 1160, 1615, 1405, 1245, 1110, 880 cm$^{-1}$.

(iii) Preparation of 1-methylcyclopropanecarbonitrile.

A mixture of 1-methylcyclopropanecarboxamide (7.0 g) and excess phosphorus pentoxide was heated at 200° C. 1-Methylcyclopropanecarbonitrile was continuously distilled from the reaction flask during heating and was collected by condensation (2.3 g).

Boiling point: 126° C.

Infra Red (liquid film): 2980, 2950, 2250, 1465, 1430, 1035, 955, 895 cm$^{-1}$.

$^1$H NMR (CDCl$_3$): 0.76 (m, 2H); 1.24 (m, 2H); 1.40 (s, 3H).

EXAMPLE 47

1-Methylcyclohexylcarbonitrile was prepared according to the method given in Example 46 from 1-methylcyclohexylcarboxylic acid.

(i) 1-methylcyclohexylcarboxylic acid chloride from 1-methylcyclohexylcarboxylic acid and oxalyl chloride.

Infra Red (thin film): 2937, 2958, 1789, 1450, 1378, 1278, 1142, 1047, 984, 932, 912, 951, 838, 764 and 642 cm$^{-1}$ (ii) 1-methylcyclohexylcarboxamide from 1-methylcyclohexylcarboxylic acid chloride and concentrated aqueous ammonia solution.

270 MHz $^1$H NMR (CDCl$_3$): 1.17 (3H,s); 1.30–1.60 (8H,m); 1.90 (2H,m); 5.70 (1H, broad s); 5.90 (1H, broad s).

Infra Red (thin film); 3400, 3353, 2923, 1642, 1620, 1458 and 1398 cm$^{-1}$ (iii) 1-methylclohexylcarbonitrile from 1-methylcyclohexylcarboxamide and phosphorous pentoxide.

60 MHz $^1$H NMR (CDCl$_3$): 1.35 (3H,s); 1.2–2.0 (10H,m)

Infra Red (liquid film): 2933, 2859, 2231 and 1451 cm$^{-1}$

EXAMPLE 48

This Example illustrates an emulsifiable concentrate composition which is readily convertible by dilution with water into a liquid preparation suitable for spraying purposes. The concentrate has the following composition:

| | % Weight |
|---|---|
| Compound No 1 | 25.0 |
| SYNPERONIC NP13 (nonylphenol-ethyleneoxide condensate; Synperonic is a registered trade mark) | 2.5 |
| Calcium dodecylbenzenesulphonate | 2.5 |
| AROMASOL H (alkylbenzene solvent; Aromasol is a registered trade mark) | 70 |

EXAMPLE 49

This Example illustrates an emulsifiable concentrate composition which is readily convertible by dilution with water into a liquid preparation suitable for spraying purposes. The concentrate has the following composition:

|  | % Weight |
| --- | --- |
| Compound No 4 | 50.0 |
| SYNPERONIC NP13 (nonylphenol-ethyleneoxide condensate; Synperonic is a registered trade mark) | 6.0 |
| Calcium dodecylbenzenesulphonate | 4.0 |
| AROMASOL H (alkylbenzene solvent; Aromasol is a registered trade mark) | 40.0 |

EXAMPLE 50

This Example illustrates an emulsifiable concentrate composition which is readily convertible by dilution with water into a liquid preparation suitable for spraying purposes. The concentrate has the following composition:

|  | % Weight |
| --- | --- |
| Compound No 15 | 1.0 |
| SYNPERONIC OP10 (octylphenol-ethyleneoxide condensate; Synperonic is a registered trade mark) | 3.0 |
| Calcium dodecylbenzenesulphonate | 2.0 |
| AROMASOL H (alkylbenzene solvent; Aromasol is a registered trade mark) | 94.0 |

EXAMPLE 51

This Example illustrates a wettable powder composition which is readily convertible by dilution with water into a liquid preparation suitable for spraying purposes. The wettable powder has the following composition:

|  | % Weight |
| --- | --- |
| Compound No 16 | 25.0 |
| Silica | 25.0 |
| Sodium lignosulphonate | 5.0 |
| Sodium lauryl sulphate | 2.0 |
| Kaolinite | 43.0 |

EXAMPLE 52

This Example illustrates a wettable powder composition which is readily convertible by dilution with water into a liquid preparation suitable for spraying purposes. The wettable powder has the following composition:

|  | % Weight |
| --- | --- |
| Compound No 5 | 1.0 |
| Sodium lignosulphonate | 5.0 |
| Sodium lauryl sulphate | 2.0 |
| Kaolinite | 92.0 |

EXAMPLE 53

This Example illustrates wettable powder composition which is readily convertible by dilution with water into a liquid preparation suitable for spraying purposes. The wettable powder has the following composition:

|  | % Weight |
| --- | --- |
| Compound No 11 | 40.0 |
| Silica | 40.0 |
| Calcium lignosulphonate | 5.0 |
| Sodium lauryl sulphate | 2.0 |
| Kaolinite | 13.0 |

EXAMPLE 54

This Example illustrates a dusting powder which may be applied directly to plants or other surfaces and comprises 1% by weight of Compound 25 and 99% by weight of talc.

EXAMPLE 55

This Example illustrates a concentrated liquid formulation suitable for application by ultra low volume techniques after mixing with paraffinic diluents.

|  | % Weight |
| --- | --- |
| Compound No 164 | 90.0 |
| SOLVESSO 200 (inert diluent; Solvesso is a registered trade mark) | 10.0 |

EXAMPLE 56

This Example illustrates a concentrated liquid formulation suitable for application by ultra low volume techniques after mixing with paraffinic diluents.

|  | % Weight |
| --- | --- |
| Compound No 187 | 25.0 |
| SOLVESSO 200 (inert diluent; Solvesso is a registered trade mark) | 75.0 |

EXAMPLE 57

This Example illustrates a concentrated liquid formulation suitable for application by ultra low volume techniques after mixing with paraffinic diluents.

|  | % Weight |
| --- | --- |
| Compound No 92 | 10.0 |
| SOLVESSO 200 (inert diluent; Solvesso is a registered trade mark) | 90.0 |

EXAMPLE 58

This Example illustrates a capsule suspension concentrate which is readily convertible by dilution with water to form a preparation suitable for application as an aqueous spray.

|  | % Weight |
| --- | --- |
| Compound No 114 | 10.0 |
| Alkylbenzene solvent (e.g. AROMASOL H) | 5.0 |
| Toluene di-isocyanate | 3.0 |
| Ethylenediamine | 2.0 |
| Polyvinyl alcohol | 2.0 |
| Bentonite | 1.5 |
| Polysaccharide (e.g. KELTROL; Keltrol is a registered trade mark) | 0.1 |
| Water | 76.4 |

EXAMPLE 59

This Example illustrates a capsule suspension concentrate which is readily convertible by dilution with water to form a preparation suitable for application as an aqueous spray.

| | % Weight |
|---|---|
| Compound No 125 | 1.0 |
| Alkylbenzene solvent (e.g. AROMASOL H) | 10.0 |
| Toluene di-isocyanate | 3.0 |
| Ethylenediamine | 2.0 |
| Polyvinyl alcohol | 2.0 |
| Bentonite | 1.5 |
| Polysaccharide (e.g. KELTROL; Keltrol is a registered trade mark) | 0.1 |
| Water | 80.4 |

EXAMPLE 60

A ready for use granular formulation:

| | % Weight |
|---|---|
| Compound No 120 | 0.5 |
| SOLVESSO 200 | 0.2 |
| nonylphenol ethoxylate (eg Synperonic NP8) | 0.1 |
| Calcium carbonate granules (0.3–0.7 mm) | 99.2 |

EXAMPLE 61

An aqueous suspension concentrate:

| | % Weight |
|---|---|
| Compound No 179 | 5.0 |
| Kaolinite | 15.0 |
| Sodium lignosulphonate | 3.0 |
| nonylphenolethoxylate (eg Synperonic NP 8) | 1.5 |
| propylene glycol | 10.0 |
| Bentonite | 2.0 |
| Polysaccharide (eg Keltrol) | 0.1 |
| Bactericide (eg Proxel; Proxel is a registered Trade Mark) | 0.1 |
| Water | 63.3 |

EXAMPLE 62

A ready for use dust (D.P.) made from a concentrate

| | % Weight |
|---|---|
| Concentrate: | |
| Compound No 205 | 10 |
| Silica | 20 |
| Magnesium Carbonate | 70 |
| Dust Example containing 1% active ingredient: | |
| Above concentrate | 10 |
| Talc | 90 |

EXAMPLE 63

This Example illustrates the insecticidal properties of the Products of this invention.

The activity of the Product was determined using a variety of insect pests. The Product was used in the form of liquid preparations containing 500, 250 or 100 parts per million (ppm) by weight of the Product. The preparations were made by dissolving the Product in acetone and diluting the solutions with water containing 0.01% by weight of a wetting agent sold under the trade name "LISSAPOL" NX until the liquid preparations contained the required concentration of the Product. "LISSAPOL" is a Registered Trade Mark.

The test procedure adopted with regard to each pest was basically the same and comprised supporting a number of the pests on a medium which was usually a host plant or a foodstuff on which the pests feed, and treating either or both the pests and the medium with the preparations. The mortality of the pests was then assessed at periods usually varying from one to three days after the treatment.

In the case of the species Musca domestica (housefly), additional tests to determines the knockdown effect of the compounds were performed. Details are given in Table II.

The results of the tests are given in Table III for each of the Products, at the rate in parts per million given in the second column as a grading of mortality designated as A, B or C wherein A indicates 80–100% mortality or knockdown, B indicates 50–79% mortality or knockdown and C indicates less than 50% mortality or knockdown.

In Table III the pest organism used is designated by a letter code and the pests species, the support medium or food, and the type and duration of test is given in Table II.

TABLE II

| CODE LETTERS (Table IV) | TEST SPECIES | SUPPORT MEDIUM/FOOD | TYPE OF TEST | DURATION (days) |
|---|---|---|---|---|
| TUa | Tetranychus urticae (spider mites - adult) | French bean leaf | Contact | 3 |
| TUe | Tetranychus urticae (spider mites - ova) | French bean leaf | Contact | 6 |
| MP | Myzus persicae (aphids) | Chinese Cabbage leaf | Contact | 3 |
| NL | Nilaparvata lugens (brown plant hopper) | Rice plant | Contact | 3 |
| NC | Nephotettix cincticeps (green leaf hopper - nymphs) | Rice plant | Contact | 2 |
| HV | Heliothis virescens (tobacco budworm - larvae) | Cotton leaf | Residual | 2 |
| DB | Diabrotica balteata (rootworm larvae) | Filter paper/ maize seed | Residual | 2 |
| BG/R | Blattella germanica (cockroach nymphs) | Plastic pot | Residual | 3 |
| BG/C | Blattella germanica (cockroach nymphs) | Plastic pot | Contact | 2 |

TABLE II-continued

| CODE LETTERS (Table IV) | TEST SPECIES | SUPPORT MEDIUM/FOOD | TYPE OF TEST | DURATION (days) |
|---|---|---|---|---|
| MD | *Musca domestica* (houseflies - adults) | Cotton wool/ sugar | Contact | 3 |
| MD/KD | *Musca domestica* (houseflies - adults) | Cotton/wool sugar | Knockdown | 4 hours |
| SP | *Spodoptera exigua* (lesser army worm - larvae) | Cotton leaf | Residual | 2 |

"Contact" test indicates that both pests and medium were treated and "residual" indicates that the medium was treated before infestation with the pests.

TABLE III

| Compound Number | Rate (ppm) | TUa | TUe | MP | NL | NC | MD/KD | MD | BG/R | BG/C | HV | SP | DB |
|---|---|---|---|---|---|---|---|---|---|---|---|---|---|
| 1 | 500 | A | A | A | — | A | A | C | — | C | A | C | C |
| 2 | 500 | A | C | A | — | A | C | A | — | C | A | A | A |
| 3 | 500 | A | A | C | — | A | C | C | — | C | B | A | C |
| 4 | 500 | A | C | A | — | A* | A | A** | B | — | A* | A* | A* |
| 5 | 500 | A | C | A | — | B | B | C | — | C | B | A | C |
| 6 | 500 | A | — | C | — | C | C | C | — | C | C | C | B |
| 9 | 500 | A | A | A | — | A | A | A | — | B | A | A | B |
| 11 | 500 | A | A | A | — | A | A | A | — | C | A | A | A |
| 12 | 500 | A | A | A | — | A* | A | A** | A | — | A* | A* | A* |
| 14 | 500 | A | C | A | — | A | B | A | — | C | A | C | C |
| 15 | 500 | A | A | A | — | A* | A | A** | B | — | A* | A* | A* |
| 16 | 500 | C | A | A | — | — | A | A** | B | — | A* | A* | C* |
| 17 | 500 | B | C | C | — | C | C | C | C | — | C | C | A |
| 18 | 500 | A | C | A | — | A | A | C | — | C | A | A | A |
| 25 | 500 | A | A | A | — | A | A | C | — | C | A | A | B |
| 26 | 500 | A | A | B | — | A | A | A | — | C | C | A | A |
| 30 | 500 | A | C | A | — | A | A | A | — | C | A | A | A |
| 32 | 500 | A | B | A | — | A | A | A | — | C | A | A | A |
| 41 | 500 | A | C | A | — | A | A | A | — | A | A | A | C |
| 57 | 500 | A | C | A | — | A | A | A | — | C | A | A | C |
| 61 | 500 | A | C | A | — | A | A | A | — | C | C | A | C |
| 68 | 500 | A | C | A | — | A | C | C | — | C | A | B | C |
| 74 | 500 | A | C | B | — | A | C | B | — | C | A | A | C |
| 76 | 500 | A | C | A | — | A | A | B | — | B | A | A | C |
| 78 | 500 | A | B | A | — | A | A | C | — | B | A | A | A |
| 82 | 1000 | A | C | A | — | A | A | C | — | C | A | A | C |
| 87 | 500 | A | A | A | — | B* | A | A** | A | — | B* | A* | A* |
| 90 | 500 | A | C | A | — | A* | A | A** | A | — | A* | A* | A* |
| 91 | 500 | A | A | A | — | A | A | A | — | A | A | A | A |
| 92 | 500 | A | C | A | — | A* | A | A** | C | — | A* | A* | C* |
| 113 | 500 | C | C | B | C | — | A | A** | C | — | C* | C* | C* |
| 114 | 500 | A | A | A | — | A* | A | A | A | — | A* | A* | A* |
| 115 | 500 | A | A | A | C | — | C | A** | A | — | A* | A* | C* |
| 116 | 500 | A | A | A | A | — | A | A** | A | — | A* | A* | A* |
| 117 | 500 | A | A | A | A | — | A | A** | A | — | A* | A* | B* |
| 118 | 500 | B | C | A | C | — | — | A** | C | — | B* | B* | C* |
| 119 | 500 | A | C | A | — | A* | A | A** | A | — | C* | A* | A* |
| 120 | 500 | A | C | A | — | A | A | A | C | — | A | A | C |
| 121 | 500 | A | C | A | C | — | B | A** | C | — | A* | A* | A* |
| 122 | 500 | A | C | A | C | — | A | A** | C | — | A* | A* | B* |
| 123 | 500 | A | A | A | A | — | A | A** | B | — | A* | A* | C* |
| 125 | 500 | A | C | A | — | A* | B | B** | C | — | A* | A* | A* |
| 131 | 500 | A | A | A | — | A | A | C | — | C | C | A | A |
| 135 | 500 | A | A | A | — | A | A | A | — | C | C | A | A |
| 139 | 500 | A | C | A | — | A | A | A | — | A | A | A | C |
| 161 | 500 | A | A | A | — | A | A | A | — | B | C | A | B |
| 163 | 500 | A | C | C | — | C | C | C | — | C | C | B | C |
| 164 | 500 | A | C | B | — | C | A | C | — | C | B | A | C |
| 165 | 500 | C | C | C | — | B | C | C | — | C | C | C | C |
| 166 | 500 | A | A | A | — | B | C | C | — | C | C | A | A |
| 167 | 500 | A | A | A | — | — | C | C | — | C | A | A | A |
| 168 | 500 | A | A | A | — | A | C | C | — | C | B | B | C |
| 169 | 500 | A | A | A | — | A | A | A | — | C | C | A | C |
| 170 | 500 | A | C | C | — | B | B | C | — | C | C | A | C |
| 171 | 500 | A | C | C | — | C | C | C | — | C | C | C | C |
| 172 | 500 | A | C | B | — | C | C | C | — | C | C | C | C |
| 173 | 500 | A | C | A | — | A | C | C | — | C | A | A | C |
| 174 | 500 | A | C | A | — | B | C | C | — | C | C | C | C |
| 175 | 500 | A | C | C | — | C | C | C | — | C | C | C | C |
| 176 | 500 | A | C | A | — | A | A | A | — | C | A | A | C |
| 177 | 500 | A | C | A | — | A | A | C | — | C | C | A | C |
| 178 | 500 | A | C | A | — | A | C | C | — | C | C | C | C |
| 179 | 500 | A | C | A | — | A | C | C | — | C | C | C | C |
| 180 | 500 | A | C | A | — | A | A | A | — | C | A | A | C |
| 181 | 500 | A | C | A | — | A | A | A | — | C | A | A | A |
| 182 | 500 | A | C | B | — | A | C | C | — | C | C | C | C |

TABLE III-continued

| Compound Number | Rate (ppm) | TUa | TUe | MP | NL | NC | MD/KD | MD | BG/R | BG/C | HV | SP | DB |
|---|---|---|---|---|---|---|---|---|---|---|---|---|---|
| 183 | 500 | A | C | C | — | A | A | A | — | C | A | A | C |
| 185 | 500 | A | C | A | — | A | A | B | — | C | A | A | C |
| 186 | 500 | A | C | A | — | A | A | C | — | C | A | A | C |
| 187 | 500 | A | C | A | — | A | A | B | — | C | B | A | C |
| 188 | 500 | A | C | A | — | B | C | C | — | C | B | A | C |
| 189 | 500 | A | C | A | — | A | B | C | — | C | C | A | C |
| 190 | 500 | A | C | A | — | A | A | C | — | C | A | A | C |
| 192 | 500 | A | C | B | — | C | C | C | — | C | C | A | C |
| 193 | 500 | A | C | A | — | B | C | C | — | C | C | A | C |
| 194 | 500 | A | C | C | — | C | C | C | — | C | C | A | C |
| 195 | 500 | A | A | A | — | A | C | C | — | C | A | A | A |
| 196 | 500 | C | C | C | — | C | C | C | — | C | C | A | C |
| 197 | 500 | A | A | A | — | A | A | C | — | C | A | A | A |
| 198 | 500 | A | C | A | — | A | A | C | — | A | A | A | A |
| 199 | 500 | A | A | A | — | A | A | A | — | A | A | A | B |
| 200 | 500 | A | C | A | — | A | A | C | — | C | A | A | C |
| 201 | 500 | A | B | A | — | A | A | A | — | B | A | A | A |
| 202 | 500 | A | C | A | — | A | A | C | — | C | B | A | C |
| 203 | 500 | A | B | A | — | A | A | A | — | B | A | A | C |
| 204 | 500 | A | C | A | — | A | A | A | — | B | A | A | C |
| 205 | 500 | A | C | A | — | A | C | C | — | C | A | A | C |
| 206 | 500 | A | C | A | — | A | A | A | — | B | A | A | A |
| 207 | 500 | A | C | A | — | A | A | C | — | C | C | C | C |
| 208 | 500 | A | C | A | — | A | C | C | — | C | C | C | C |
| 209 | 500 | A | C | B | — | C | C | C | — | C | A | B | C |
| 210 | 500 | A | A | C | — | — | — | — | — | C | C | C | C |
| 211 | 500 | A | A | A | — | A | A | C | — | C | C | A | C |
| 212 | 500 | A | C | A | — | A | A | C | — | C | C | B | C |
| 213 | 500 | A | C | B | — | C | A | C | — | B | C | C | C |
| 214 | 500 | A | C | A | — | A* | A | B** | A | — | C* | A* | C* |
| 216 | 500 | A | C | C | — | B | C | C | — | C | C | B | C |
| 217 | 500 | A | C | A | — | A | A | A | — | C | A | A | C |
| 218 | 500 | A | C | A | — | A | C | C | — | C | C | C | C |
| 220 | 500 | A | C | A | — | A | A | A | — | C | C | B | B |

Note:
*Indicates test duration of 3 days
**Indicates test duration of 1 day

We claim:

1. A compound of formula (VI):

(VI)

wherein $R^1$ is selected from alkyl of 1 to 6 carbon atoms; alkenyl of 2 to 8 carbon atoms; alkynyl of 2 to 6 carbon atoms; haloalkyl of 1 to 4 carbon atoms; haloalkenyl of 2 to 8 carbon atoms; and cycloalkyl of 3 to 6 carbon atoms optionally substituted by one or more substituents selected from alkyl of 1 to 4 carbon atoms and halogen; R represents lower alkyl of from 1 to 6 carbon atoms, and $R^5$ represents alkoxy of from 1 to 6 carbon atoms, dialkylamino wherein each alkyl group is from 1 to 4 carbon atoms, piperidin-1-yl or pyrollidin-1-yl.

* * * * *